US009376677B2

(12) United States Patent
Mir

(10) Patent No.: US 9,376,677 B2
(45) Date of Patent: *Jun. 28, 2016

(54) ARRAYS AND METHODS OF USE

(71) Applicant: Singular Bio, Inc., San Francisco, CA (US)

(72) Inventor: Kalim Mir, Oxford (GB)

(73) Assignee: Singular Bio, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,946

(22) Filed: Jan. 14, 2016

(65) Prior Publication Data

US 2016/0122754 A1    May 5, 2016

Related U.S. Application Data

(63) Continuation of application No. 14/806,096, filed on Jul. 22, 2015, which is a continuation of application No. 14/616,224, filed on Feb. 6, 2015, which is a continuation of application No. 13/455,766, filed on Apr. 25, 2012, now Pat. No. 9,057,730, which is a continuation of application No. 10/664,000, filed on Sep. 16, 2003, now abandoned, which is a continuation of application No. PCT/GB02/01245, filed on Mar. 18, 2002.

(30) Foreign Application Priority Data

Mar. 16, 2001 (GB) .................................. 0106635.6
Aug. 2, 2001 (GB) .................................. 0118879.6

(51) Int. Cl.
| | |
|---|---|
| *C12Q 1/68* | (2006.01) |
| *C12P 19/34* | (2006.01) |
| *C12M 1/00* | (2006.01) |
| *C12M 1/34* | (2006.01) |
| *C12M 3/00* | (2006.01) |
| *C07H 21/02* | (2006.01) |
| *C07H 21/04* | (2006.01) |
| *C07H 21/00* | (2006.01) |
| *C12N 15/10* | (2006.01) |
| *G01N 33/58* | (2006.01) |

(52) U.S. Cl.
CPC .......... *C12N 15/1065* (2013.01); *C12Q 1/6837* (2013.01); *G01N 33/582* (2013.01)

(58) Field of Classification Search
USPC .......... 435/6.1, 6.11, 6.12, 91.1, 91.2, 283.1, 435/287.1, 287.2; 536/23.1, 24.3, 24.33, 536/25.3; 422/50, 68.1
See application file for complete search history.

(56) References Cited

U.S. PATENT DOCUMENTS

| | | | |
|---|---|---|---|
| 5,256,536 | A | 10/1993 | Miyada et al. |
| 5,547,839 | A | 8/1996 | Dower et al. |
| 6,028,189 | A | 2/2000 | Blanchard |
| 6,103,463 | A | 8/2000 | Chetverin et al. |
| 6,268,146 | B1 | 7/2001 | Shultz et al. |
| 6,346,379 | B1 | 2/2002 | Gelfand et al. |
| 6,495,320 | B1 | 12/2002 | Lockhart et al. |
| 6,706,473 | B1 | 3/2004 | Edman et al. |

FOREIGN PATENT DOCUMENTS

| | | |
|---|---|---|
| WO | 89/10977 A1 | 11/1989 |
| WO | 92/10092 A1 | 6/1992 |
| WO | 96/27025 A1 | 9/1996 |
| WO | 98/44152 A1 | 10/1998 |
| WO | 00/06770 A1 | 2/2000 |
| WO | 00/36152 A1 | 6/2000 |
| WO | 00/79008 A2 | 12/2000 |
| WO | 01/23610 A2 | 4/2001 |
| WO | 01/57248 A3 | 8/2001 |
| WO | 01/57249 A1 | 8/2001 |

OTHER PUBLICATIONS

Liu et al, "Molecular Beacons for DNA Biosensors with Micrometer to Submicrometer Dimensions," Analytical Biochemistry, 283: 56-63 (2000).
Goodwin et al., "Single-Molecule Detection in Liquids by Laser-Induced Fluorescence," Accounts of Chemical Research, 29: 607-613 (1996).
International Preliminary Examination Report issued in related International Patent Application No. PCT/GB02/01245 dated Oct. 24, 2003.
Osborne et al., "Single-Molecule Analysis of DNA Immobilized on Microspheres," Analytical Chemistry, 72: 3678-3681 (2000).
Shalon et al., "A DNA Microarray System for Analyzing Complex DNA Samples Using Two-color Fluorescent Probe-Hybridization," Genome Research, 6: 639-645 (1996).
Extended European Search Report issued in related European Patent Application No. 14172340.3 dated Oct. 14, 2014.

*Primary Examiner* — Frank Lu
(74) *Attorney, Agent, or Firm* — Morgan, Lewis & Bockius LLP

(57) ABSTRACT

Methods are provided for producing a molecular array comprising a plurality of molecules immobilized to a solid substrate at a density which allows individual immobilized molecules to be individually resolved, wherein each individual molecule in the array is spatially addressable and the identity of each molecule is known or determined prior to immobilization. The use of spatially addressable low density molecular arrays in single molecule detection and analysis techniques is also provided. Novel assays and methods are also provided.

30 Claims, 12 Drawing Sheets

*Encoded probing of single molecules*

*Complementary strand synthesis by ligation*

*Gap Fill Ligation*

Fret

Each element of the biosensor
array contains distinct single
molecule probe sequences
(Asterisks), e.g. to detect
different pathogens

```
                        SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Lambda A oligonucleotide

<400> SEQUENCE: 1
gggcggcgac ct                                                        12

<210> SEQ ID NO 2
<211> LENGTH: 12
<212> TYPE: DNA
<213> ORGANISM: Artificial Sequence
<220> FEATURE:
<223> OTHER INFORMATION: Lambda B oligonucleotide

<400> SEQUENCE: 2
aggtcgccgc cc                                                        12

<210> SEQ ID NO 3
<211> LENGTH: 22
<212> TYPE: DNA
<213> ORGANISM: Artificial Sequence
<220> FEATURE:
<223> OTHER INFORMATION: Anchored capture oligonucleotide
<220> FEATURE:
<221> NAME/KEY: misc_feature
<222> LOCATION: (22)..(22)
<223> OTHER INFORMATION: n is a, c, g, or t

<400> SEQUENCE: 3
tttttttttt tttttttttt vn                                             22
```

ARRAYS AND METHODS OF USE

A computer readable text file, entitled "SequenceListing.txt," created on or about Dec. 12, 2012 with a file size of about 2 kb contains the sequence listing for this application and is hereby incorporated by reference in its entirety.

FIELD OF THE INVENTION

The present invention relates to spatially addressable low density molecular arrays and analytical approaches based on single molecule detection techniques.

BACKGROUND TO THE INVENTION

Progress in the human genome project has seeded the need to (i) analyse the expression characteristics of genes and gene products and (ii) analyse the variations in genes and genomes. This has precipitated great interest in methods for large-scale, parallel studies. Interest in developing new methods for detecting variation has further been fuelled by the success of using DNA markers in finding genes for monogenic inherited disorders and recent proposals on large-scale association studies for dissecting complex traits. There is also a need for large-scale studies and high-throughput screening in the search for drugs in the pharmaceutical industry.

This interest in large scale studies may also in the future extend to other areas such as the semiconductor industry where the emergence of devices based on organic molecules such as poly(p-phenylene vinylidene), PPV, and the nascent fields of molecular electronics and nanotechnology seed the demand for new molecules with novel or desirable features and this in turn may see the need to turn to large scale searching.

In the biotechnology and pharmaceutical sector, large scale studies are preferably done either in homogeneous assays on a microtitre plate (96 well and 384 well plates are common and higher capacity plates are available) or in an array format. Spatially addressable arrays (where the sequence identity of a molecule is specified by the location of the element in which the molecule is contained, within the array of elements) of chemical or biochemical species have found wide use in genetics, biology, chemistry and materials science. Arrays can be formed in (i) a disperse solid phase such as beads and bundled hollow fibres/optical fibres, (ii) individual wells of microtitre plates/nanovials or (iii) on a homogeneous medium/surface on which individual elements can be spatially addressed. The latter types of arrays (iii) can be made on semi-permeable materials such as gels, gel pads, porous silicon, microchannel arrays (so called 3-D biochips) (Benoit et al; Anal. Chem 2001 73:2412-2420) and impermeable supports such as silicon wafers, glass, gold coated surfaces, ceramics and plastics. They can also be made within the walls of microfluidic channels (Gao et al; Nucleic Acids Res. 2001 29: 4744-4750). Furthermore the surface or sub-surface may comprise a functional layer such as an electrode.

All elements in arrays of type (i) and (iii) are contained within a single reaction volume, whilst each element of (ii) is contained in a separate reaction volume.

To date, methods have involved analysing the reactions of molecules in bulk. Although bulk or ensemble approaches have in the past proved useful, there are barriers to progress in a number of directions. The results generated are usually an average of millions of reactions where multiple events, multi-step events and variations from the average cannot be resolved and detection methods that are adapted for high frequency events are insensitive to rare events. The practical limitations associated with bulk analysis include the following:

1. The techniques used for the detection of events in bulk phase analysis are not sensitive enough to detect rare events which may be due to low sample amount or weak interaction with probes.
   a. Detecting the presence of rare transcripts in mRNA profiling. This problem is related to the limited dynamic range of bulk analysis which is in the order of $10^4$ whereas the different abundance levels of mRNAs in a cell are in the $10^5$ range. Hence to cater for the more common events, detection methods are not sensitive enough to detect rare events.
   b. In the amounts of samples that are usually available to perform genetic analysis there are not enough copies of each sequence in genomic DNA to be detected. Therefore the Polymerase Chain Reaction (PCR) is used to increase the amount of material from genomic DNA so that sufficient signal for detection can be obtained from the desired loci.
   c. Due to secondary structure around certain target loci very few hybridisation events go to completion. The few that do, need to be detected. These events may be too few to be detected by conventional bulk measurements.
   d. The number of analyte molecules in the sample is vanishingly small. For example, in pre-implantation analysis a single molecule must be analysed. In analysis of ancient DNA the amount of sample material available is often also very small.
2. A rare event in a background of common events at a particular locus is impossible to detect in the bulk phase due to it being masked by the more common events. There are a number of instances where this is important:
   a. Detecting loss of heterozygosity (LOH) in tumours comprising mixed cell populations and early events in tumorigenesis.
   b. Determining minimal residual disease in patients with cancer and early detection of relapse by detecting mutation within a wild type background.
   c. Prenatal diagnosis of genetic disorders directly from the small number of foetal cells in the maternal circulation (hence detection from mother's blood rather than from amniocentesis).
   d. Detection of specific alleles in pooled population samples.
3. It is difficult to resolve heterogeneous events. For example it is difficult to separate out the contribution (or the lack of) to signal from errors such as foldback, mis-priming or self-priming from genuine signals based on the interactions being measured.
4. Complex samples such as genomic DNA and mRNA populations pose difficulties.
   a. One problem is cross reactions of analyte species within the sample.
   b. On arrays, another is the high degree of erroneous interactions which in many cases are likely to be due to mismatch interactions driven by high effective concentrations of certain species. This is one reason for low signal to noise. A ratio as low as 1:12 has been used in published array studies for base calling (Cronin et al, Human Mutation 7:244-55, 1996).
   c. In some cases erroneous interactions can even be responsible for the majority of signal (Mir, K; D. Phil thesis, Oxford University, 1995).
   d. Detecting a true representative signal of a rare mRNA transcript within a mRNA population is difficult.
   e. PCR is used in genetic analysis to reduce the complexity of sample from genomic DNA, so that the desired loci become enriched.

5. The bulk nature of conventional methods does not allow access to specific characteristics (particularly, more than one feature) of individual molecules. One example in genetic analysis is the need to obtain genetic phase or haplotype information—the specific alleles associated with each chromosome. Bulk analysis cannot resolve haplotype from a heterozygotic sample. Current molecular biology techniques that are available, such as allele-specific or single molecule PCR are difficult to optimise and apply on a large scale.

6. Transient processes are difficult to resolve. This is needed when deciphering the molecular mechanisms of processes. Also transient molecular binding events (such as nucleation of a hybridisation event which is blocked from propagation due to secondary structure in the target) have fractional occupancy times which cannot be detected by conventional solid-phase binding assays.

When two samples are compared, small differences in concentration (less than twofold difference) are difficult to unequivocally discern.

Microarray gene expression analysis using unamplified cDNA target typically requires 106 cells or 100 micrograms of tissue. Neither expression analysis nor analysis of genetic variation can be performed directly on material obtained from a single cell which would be advantageous in a number of cases (e.g. analysis of mRNA from cells in early development or genomic DNA from sperm).

Further, it would be highly desirable if the amplification processes that are required before most biological or genetic analysis could be avoided.

PCR is used for the analysis of Variable Number of Tandem Repeats is central to Forensics and Paternity testing. Linkage studies have traditionally used Short Tandem repeats as markers analysis which is performed by PCR.

The need to avoid PCR is particularly acute in the large scale analysis of SNPs. The need to design primers and perform PCR on a large number of SNP sites presents a major drawback. The largest scales of analysis that are currently being implemented (e.g. using Orchid Bioscience and Sequenom systems) remain too expensive to allow meaningful association studies to be performed by all but a few large organizations such as the Pharmaceutical companies. Although, the number of SNPs needed for association studies has been actively debated, the highest estimates are being revised down due to recent reports that there are large blocks of linkage disequilibrium within the genome. Hence, the number of SNPS needed to represent the diversity in the genome could be 10 fold fewer than was expected. However, this needs to be taken with the caveat that there are some regions of the genome where the extent of linkage disequilibrium is far lower and a greater number of SNPs would be needed to represent the diversity in these areas. Even so, if each site had to be amplified individually the task would be enormous. In practice, PCR can be multiplexed. However, the extent to which this can be done is limited and increased errors, such as primer-dimer formation and mismatches as well as the increased viscosity of reaction, present barriers to success and limits multiplexing to around ten sites in most laboratories.

It is clear that the cost of performing SNP detection reactions on the scale required for high-throughput analysis of polymorphisms in a population is prohibitive if each reaction needs to be conducted separately, or if only a limited multiplexing possibility exists. A highly multiplexed, simple and cost-effective route to SNP analysis will be required if the potential of pharmacogenomics, pharmacogenetics as well as large-scale genetics is to be realised. DNA pooling is a solution for some aspects of genetic analysis but accurate allele frequencies must be obtained which is difficult especially for rare alleles.

Since it involves determining the association of a series of alleles along a single chromosome, the haplotype is thought to be far more informative than the analysis of individual SNP. An international effort is underway for making a comprehensive haplotype map of the human genome. Generally, haplotypes are determined is by long-range allele specific PCR. However, the construction of somatic cell hybrids prior to haplotype determination is an alternative method.

A method for haplotyping on single molecules in solution has been proposed in patent (WO 01/90418), however, in this method the molecules are not surface captured, positional information of the SNP is not obtained and each SNP must be coded with a different colour. For several years, plans for large scale SNP analysis have been laid around the common disease-common variant (CD/CV) (i.e. common SNP) hypothesis of complex diseases (Reich D E and Lander E S Trends Genet 17: 502-50 2001)). The SNP consortium has amassed more than a million putatively common SNPs. However practical use of this set is confounded by the fact that different SNPs may be common in different ethnic populations and many of the putative SNPs may not be truly polymorphic. Furthermore, the CD/CV hypothesis has recently come under challenge from assertions that rare alleles may contribute to the common diseases (Weiss K M, Clark A G, Trends Genet 2002 January; 18(1):19-24). If this were the case, although "new" rare alleles would be sufficiently in linkage disequilibrium with a common SNP for the association with the region that contains both to be successfully made, if the allele was "ancient" and rare then the common SNPs and haplotype maps would not represent the diversity. In this scenario alternative strategies are needed to find causative regions. Instead of genome-wide scan of common SNPs it may be that there will be a need for whole genome sequencing or re-sequencing of thousands of case and control samples to access all variants. The commercial sequencing of the human genome, which built on information from the public genome project, cost approximately 300 million dollars over a period of about one year. This cost and timescale is prohibitive as an alternative to SNP analysis for finding associations between DNA sequence and disease. Clearly, if sequencing is to replace current approaches to large scale genetic studies, radically different methods are needed.

It would be advantageous if sequencing runs could be on the scale of genomes or at least small genomes or whole genes. Even increasing read-lengths beyond 300-500 nt would be useful. Today, sequencing is almost exclusively done by the Sanger dideoxy method. A number of alternative sequencing methods have been suggested but none are in use today. These methods include:

1 Sequencing by synthesis
2 Direct analysis of the sequence of a single molecule
3 Sequencing by Hybridisation Re-sequencing by chip methods is an alternative to de-novo sequencing. The 21.7 million bases of non-repetitive sequence of chromosome 21 has recently been re-sequenced by chip methods by Patil et al (Science 294: 1719-1722, 2001). The haplotype structure was conserved in this study by making somatic cell hybrids prior to chip analysis. However, the cost of large scale re-sequencing by this method is still high and only 65% of the bases that were probed gave results of enough confidence for the base to be called.

SUMMARY OF THE INVENTION

The present invention overcomes the above-mentioned practical limitations associated with bulk analysis. This can be achieved by the precision, richness of information, speed and throughput that can be obtained by taking analysis to the level of single molecules. The present invention particularly addresses problems of large-scale and genome-wide analysis.

In recent years methods have been developed for detecting and analysing individual molecules on surfaces or in solution. For example, single molecule methods using optical laser-trapping have been developed to study the transcription of immobilised RNA polymerase molecules (Yin et al., 1995, Science 270: 1653-56). In addition, individual ATP turnover by single myosin molecules has been visualised using evanescent wave excitation (Funatsu et al., 1995, Nature 374: 555-59). Moreover, analysis has been performed on single molecules in unamplified genomic DNA (Castro A. and Williams J G K, 1997, Anal. Chem. 10 69:3915-3920).

To date single molecule analysis has only been conducted in simple examples but as mentioned above the challenge of modern genetics and other areas is to apply tests on a large scale. An important aspect of any single molecule detection technique for rapid analysis of large numbers of molecules is a system for sorting and tracking (or following) individual reactions on single molecules in parallel. Capturing and resolving single molecules on spatially addressable arrays of single molecules of known or encoded sequence can achieve this.

In present bulk methods, analysis is done by looking at the ensemble signal from all molecules in the assay. The spatial density of probe molecules or the assay signals that are obtained are at too high a density to resolve single molecules by the methods in general use (e.g. microarray scanners).

The approach of the present invention is set apart from traditional bulk array technologies inter alia by the type of information it aims to acquire. Furthermore it describes arrays in which the density of functional molecules is substantially lower than those of bulk arrays. The low density signals from these arrays may not be sufficiently-readable by instrumentation typically used for analysing the results of bulk arrays particularly due to high background. The manufacture of single molecule arrays of the invention requires special measures as described herein.

Accordingly, the present invention provides in a first embodiment a method for producing a molecular array which method comprises immobilising on a solid phase a plurality of molecules at a density which allows individual immobilised molecules to be individually resolved, wherein the identity of each individual molecule in the array is spatially addressable and the identity of each molecule is known or determined prior to immobilisation.

The present invention also provides a method for producing a molecular array which method comprises immobilising to a solid phase a plurality of defined molecules at a density which allows an individual immobilised molecule to be individually resolved by a method of choice, wherein each individual molecule in the array is spatially addressable.

In a second embodiment, the present invention provides a method for producing a molecular array which method comprises:
(i) providing a molecular array comprising a plurality of molecules immobilised to a solid phase at a density such that individual immobilised molecules are not capable of being individually resolved; and
(ii) reducing the density of functional immobilised molecules in the array such that the remaining individual functional immobilised molecules are capable of being individually resolved;
wherein the identity of each individual functional molecule in the resulting array is spatially addressable and the identity of each molecule is known or determined prior to the density reduction step.

The present invention also provides a method for producing a molecular array which method comprises:
(i) providing a molecular array comprising a plurality of defined spatially addressable molecules immobilised to a solid phase at a density such that individual immobilised molecules are not capable of being individually resolved by optical means or another method of choice; and
(ii) reducing the density of functional immobilised molecules in the array such that each remaining individual functional immobilised molecule is capable of being individually resolved.

Preferably the immobilised molecules are present within discrete spatially addressable elements. In one such embodiment, a plurality of molecular species are present within one or more of the discrete spatially addressable elements and each molecular species in an element can be distinguished from other molecular species in the element by means of a label. In another embodiment the plurality of molecules are not distinguishable by a label but comprise a degenerate set of sequences, for example representing members of a gene family, according to which they can be distinguished.

The present invention also provides a molecular array obtained by the above first and second embodiments of the invention.

The present invention further provides means to analyse the array of single molecules, wherein a physical, chemical or other property can be determined. For example, molecules which fluoresce at a certain tested wavelength can be directly sampled.

The present invention further provides a number of techniques for detecting interactions between sample molecules and the constituent molecules of molecular arrays.

Accordingly, the present invention provides the use of a molecular array in a method of identifying one or more array molecules which interact with a target, which molecular array comprises a plurality of molecules immobilised to a solid phase at a density which allows each individual immobilised molecule to be individually resolved, wherein the identity of each individual immobilised molecule is known due to its location within a spatially addressable array and the identity of each immobilised molecule is known or wherein the identity of each individual molecule is encoded and can be decoded, for example with reference to a look up table.

Typically said method comprises contacting the array with the sample and interrogating one or more individual immobilised molecules to determine whether a target molecule has bound.

Preferably the target molecule or the probe-target molecule complex is labelled.

Preferably interrogation is by an method for detecting electromagnetic radiation such as a method selected from far-field optical methods, near-field optical methods, epi-fluorescence spectroscopy, confocal microscopy, two-photon microscopy, and total internal reflection microscopy, where the target molecule or the probe-target molecule complex is labelled with an electromagnetic radiation emitter. Other methods of microscopy, such as atomic force microscopy (AFM) or other scanning probe microscopies (SPM) are also appropriate. Here it may not be necessary to label the target or probe-target molecule complex. Alternatively, labels that can be detected by SPM can be used.

In one embodiment, the immobilised molecules are of the same chemical class as the target molecules. In another embodiment, the immobilised molecules are of a different chemical class to the target molecules.

In a preferred aspect, target molecules are genomic DNA or cDNA or mRNA. Accordingly, the molecular array can be used, for example, in sequence analysis, gene expression analysis and in the detection of single nucleotide polymorphisms in a sample of nucleic acids.

Thus in one preferred embodiment the immobilised molecules of the array and the target molecules are nucleic acids and the contacting step takes place under conditions which allow hybridisation of the immobilised molecules to the target molecules.

The molecular array can also be used more generally in identifying compounds which interact with one or more molecules in the array. In this case the preferred targets are small molecules, RNAs, cDNAs, proteins or genomic DNA.

Particular applications of molecular arrays according to the invention, and of single molecule detection techniques in general, are set forth herein. Particularly preferred uses include the analysis of nucleic acid, such as in SNP typing, sequencing and the like, in biosensors and in genetic approaches such as association studies and in genomics and proteomics.

In a further aspect, the invention relates to a method for typing single nucleotide polymorphisms (SNPs) and mutations in nucleic acids, comprising the steps of:
a) providing a repertoire of probes complementary to one or more nucleic acids present in a sample, which nucleic acids may possess one or more polymorphisms, said repertoire being presented such that molecules may be individually resolved;
b) exposing the sample to the repertoire and allowing nucleic acids present in the sample to hybridise to the probes at a desired stringency, and optionally further processing;
c) detecting binding events or the result of processing.

The detection of binding events can be aided by eluting the unhybridised nucleic acids from the repertoire and detecting individual hybridised nucleic acid molecules.

Advantageously, the repertoire is presented as an array, which is preferably an array as described hereinbefore.

The present invention is particularly applicable to DNA pooling strategies in genetic analysis and detection of low frequency polymorphisms. DNA pooling strategies involve mixing multiple samples together and analysing them together to save costs and time.

The present invention is also applicable to detection of low frequency mutations in a wild type background.

The present invention can also be applied where the amount of sample material is low such as in biosensor or chemical sensor applications.

The invention is moreover applicable to haplotyping, in which a multiallelic probe set is used to analyse each sample molecule for two or more features simultaneously. For example, a first probe can be used to immobilise the sample nucleic acid to the solid phase, and optionally simultaneously to identify one polymorphism or mutation; and a second probe can be used to hybridise with the immobilised sample nucleic acid and detect a second polymorphism or mutation. Thus, the first probe (or biallelic probe set) is arrayed on the solid phase, and the second probe (or biallelic probe set) is provided in solution (or is also arrayed; see below). Further probes can be used as required. Thus, the method of the invention may comprise a further step of hybridising the sample nucleic acids with one or more further probes in solution.

The signals generated by the first and second probes can be differentiated, for example, by the use of differentiable signal molecules such as fluorophores emitting at different wavelengths, as described in more detail below. Moreover, the signals can be differentiable based on their location along the target molecule on the solid phase. To aid localisation of signal along the molecule, molecules can be stretched out by methods known in the art.

In a still further aspect, the invention relates to a method for determining the sequence of one or more target DNA molecules. Such a method is applicable, for example, in a method for fingerprinting a nucleic acid sample, as described below. Moreover the method can be applied to complete or partial sequence determination of a nucleic acid molecule.

Thus, the invention provides a method for determining the complete or partial sequence of a target nucleic acid, comprising the steps of:
a) providing a repertoire of probes complementary to one or more nucleic acids present in a sample, said first repertoire being presented such that molecules may be individually resolved;
b) hybridising a sample comprising a target nucleic acid to the probes;
c) hybridising one or more further probes of defined sequence to the target nucleic acid; and
d) detecting the binding of individual further probes to the target nucleic acid.

Advantageously, the further probes are labelled with labels which are differentiable, such as different fluorophores.

Advantageously, the repertoire is presented as an array, which is preferably an array as described hereinbefore.

In an advantageous embodiment, target nucleic acids are captured on the solid phase surface at multiple points, which allows the molecule to be arranged horizontally on the surface and optionally sites of multiple capture are in such locations that the target molecule is elongated. In a further embodiment the molecule is attached by a single point and physical measures are taken to horizontalise it. Hybridisation of further probes can then be determined according to position as well as according to differences in label.

In a further embodiment, the invention provides a method for determining the number of sequence repeats in a sample nucleic acid, comprising the steps of:
a) providing one or more probes complementary to one or more nucleic acids present in a sample, which nucleic acids may possess one or more sequence repeats, said probes being presented such that molecules may be individually resolved;
b) hybridising a sample of nucleic acid comprising the repeats
c) contacting the nucleic acids with labelled probes complementary to said sequence repeats, or a polymerase and nucleotides; and
d) determining the number of repeats present on each sample nucleic acid by individual assessment of the number of labels incorporated into each molecule, such as by measuring the brightness of the signal produced by the labels; wherein in a preferred embodiment signal is only processed from molecules to which a second solution oligonucleotide labelled with a different label is also incorporated.

The results can be analysed in terms of intensity ratios of the repeat probes labelled with first colour and the second probe labelled with a second colour.

Advantageously, the repertoire is presented as an array, which is preferably an array as described hereinbefore.

The invention moreover provides a method for analysing the expression of one or more genes in a sample, comprising the steps of:
a) providing a repertoire of probes complementary to one or more nucleic acids present in a sample, said repertoire being presented such that molecules may be individually resolved;

b) hybridising a sample comprising said nucleic acids to the probes;

c) determining the nature and quantity of individual nucleic acid species present in the sample by counting single molecules which are hybridised to the probes.

In some cases the individual molecule can be further probed by sequences that can differentiate alternative transcripts or different members of a gene family.

Advantageously, the repertoire is presented as an array, which is preferably an array as described hereinbefore.

Preferably, the probe repertoire comprises a plurality of probes of each given specificity, thus permitting capture of more than one of each species of nucleic acid molecule in the sample. This enables accurate quantification of expression levels by single molecule counting.

In another embodiment the target sample, containing a plurality of copies of each species is immobilized and spread out on a surface and a plurality of probe molecules are gridded on top of this first layer. Each gridded spot contains within its area at least one copy of each target species. After a wash step, the molecules that have bound are determined.

The present invention provides a method for determining the sequence of all or part of a target nucleic acid molecule which method comprises:

(i) immobilising the target molecule to a solid phase at two or more points such that the molecule is substantially horizontal with respect to the surface of the solid phase;

(ii) straightening the target molecule during or after immobilisation;

(iii) contacting the target molecule with a nucleic acid probe of known sequence; and (iv) determining the position within the target molecule to which the probe hybridises.

(v) repeating steps (i) to (iv) as necessary; and (vi) reconstructing the sequence of the target molecule.

Preferably the target molecule is contacted with a plurality of probes, more preferably each probe is encoded, for example labelled with a different detectable label or tag.

The target molecule can be contacted sequentially with each of the plurality of probes. In one embodiment each probe is removed or its label is removed or photobleached from the target molecule prior to contacting the target molecule with a different probe. Typically, the probes are removed by heating, modifying the salt concentration or pH, or by applying an appropriately biased electric field. Alternatively, another oligonucleotide complementary to the probe molecule and which forms a stronger hybrid than the target strand, can displace the target strand. In another embodiment neither the probe or its label are removed, but rather their position's of interaction along the molecule are recorded before another probe is added. After a certain number of probe additions, bound probes must be removed before binding more probes.

Alternatively the target molecule is contacted with all of the plurality of probes substantially simultaneously.

In one embodiment the target is substantially a double stranded molecule and is hybridised to an LNA or PNA probe by strand invasion.

In another embodiment the target double strand is combed (or fibre FISH fibres are made) on a surface and denatured before or after combing.

In another embodiment the target is substantially single stranded and is made accessible for subsequent hybridisation by stretching out/straightening, which can be achieved by capillary forces acting on the target in solution.

In one embodiment, where it is desired to determine the sequence of single-stranded molecules, the target nucleic acid molecule is a double-stranded molecule and is derived from such a single-stranded nucleic acid molecule of interest by synthesising a complementary strand to said single-stranded nucleic acid.

The present invention also provides a method for determining the sequence of all or part of a target single-stranded nucleic acid molecule which method comprises:

(i) immobilising the target molecule to a solid phase at one, two or more points such that the molecule is substantially horizontal with respect to the surface of the solid phase;

(ii) straightening the target molecule during or after immobilisation;

(iii) contacting the target molecule with a plurality of nucleic acid probes of known sequence, each probes being labelled with a different detectable label; and (iv) ligating bound probes to form a complementary strand.

Where the probes are not bound in a contiguous manner, it is preferred prior to step (iv), to fill any gaps between bound probes by polymerisation primed by said bound probes.

The present invention also provides a method for determining the sequence of all or part of a target single-stranded nucleic acid molecule which method comprises:

(i) contacting the target molecule with a plurality of nucleic acid probes of known sequence, each probes being labelled with a different detectable label;

(ii) ligating bound probes to form a complementary strand;

(iii) immobilising the target molecule to a solid phase at one or more points such that the molecule is substantially horizontal with respect to the surface of the solid phase; and (ii) straightening the target molecule during or after immobilisation.

Where the probes are not bound in a contiguous manner, it is preferred, prior to step to fill any gaps between bound probes by polymerisation primed by said bound probes. The position where each ligation probe is attached is recorded during or after the process.

Typically, in any of the above embodiments, the solid phase is a substantially flat solid substrate or a bead/particle or rod/bar. "Solid phase", as used herein, refers to any material which is isolatable from solutions and thus includes porous materials, gels and gel-covered materials.

The present invention also provides an array produced or obtainable by any of the above methods.

The invention relates to coupling the preparation of single molecule arrays and performing assays on single molecule arrays. Particularly when either or both of these are coupled to Detection/Imaging of single molecules in arrays and Assays based on counting single molecules or recording and making measurements of signals on single molecules.

The present invention also provides software and algorithmic approaches for processing of data from the above methods.

BRIEF DESCRIPTION OF THE FIGURES

FIG. 10A: array hybridisation and combing of lambda DNA spots with high probe concentration, 100× objective magnification; FIG. 10B: array hybridisation and combing of lambda DNA spots with low probe concentration, 0.100× objective magnification; FIG. 10C: array hybridisation and combing of lambda DNA spots, 100× objective magnification; FIG. 10D: array hybridisation and combing of lambda DNA spots, 10× objective magnification

DETAILED DESCRIPTION OF THE INVENTION

Figure 1:
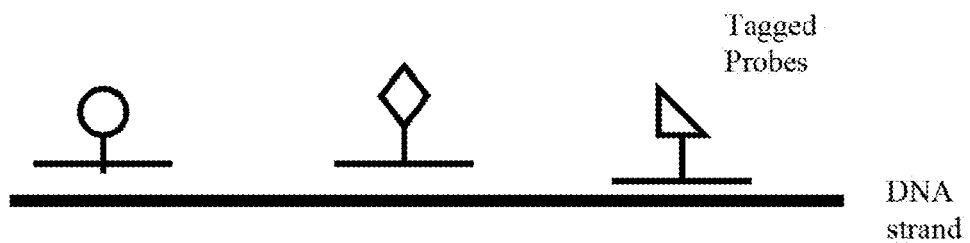
FIG. 1 illustrates encoded probing of single molecules.
Figure 2:
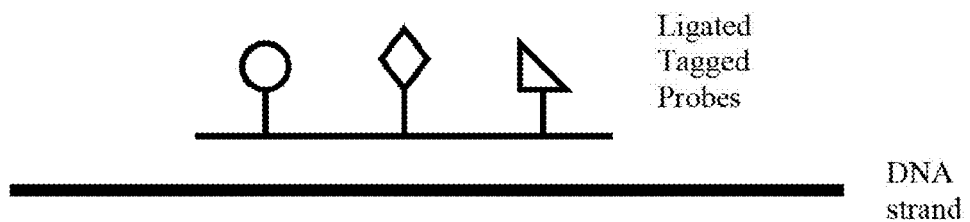
FIG. 2 illustrates complementary strand synthesis by ligation.
Figure 3:
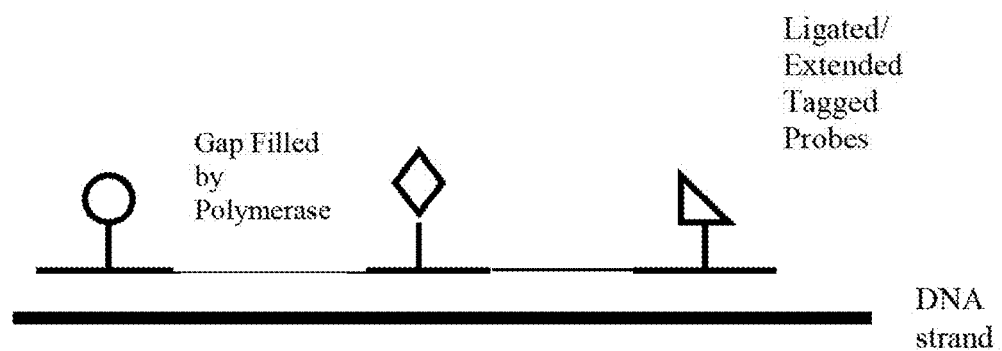
FIG. 3 illustrates gap fill ligation.
Figure 4:
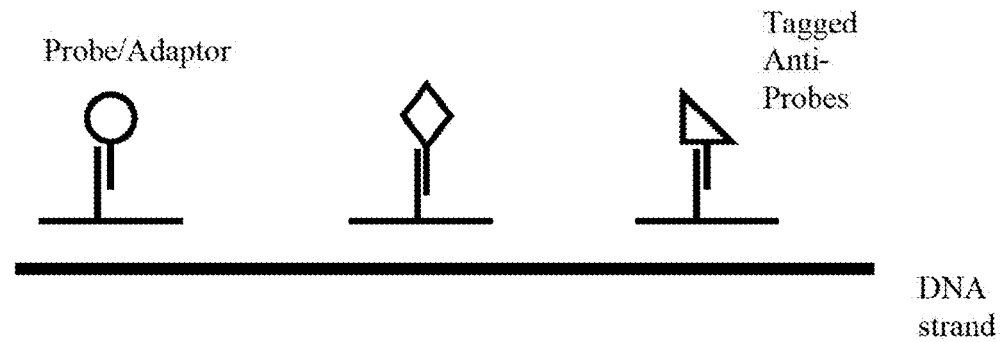
FIG. 4 illustrates the use of secondary anti-probe labels.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, $2^{nd}$ ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. —and the full version entitled Current Protocols in Molecular Biology, which are incorporated herein by reference) and chemical methods. See also Genomics, The Science and Technology Behind the Human Genome Project [1999]; Charles Cantor and Cassandra Smith (John Wiley and Sons) for genomics technology and methods including sequencing by hybridisation. DNA Microarray: A Practical Approach [1999] Ed: M. Schena, (Oxford University Press) and Nature Genetics Vol. 21 Chipping Supplement (1999) can be referred to for array methods.

The present invention possesses many advantages over conventional bulk analysis of molecular arrays. One of the key advantages is that, in accordance with the present invention, specific PCR amplification of target molecules can be dispensed with due to the sensitivity of single molecule analysis. Thus, there is no requirement to amplify target nucleic acids, which is a very cumbersome task when analysis is large scale or requires rapid turnaround and which can introduce errors due to non-linear amplification of target strands and the under-representation of rare molecular species often encountered with PCR.

Moreover, the methods of the invention can be multiplexed to a very high degree. Samples can comprise pooled genomes of target and control subject populations respectively, since accurate analysis of allele frequencies can be accurately determined by single molecule counting. Since more than a single site on each molecule can be probed, haplotype information is easily determined. There is also the possibility of obtaining haplotype frequencies. Such methods are particularly applicable in association studies, where SNP frequencies are correlated with diseases in a population. The expense of single SNP typing reactions can be prohibitive when each study requires the performance of millions of individual reactions; the present invention permits millions of individual reactions to be performed and analysed on a single array surface.

A. Methods of Manufacturing Low Density Arrays.

The present invention is in one aspect concerned with the production of molecular arrays wherein the individual molecules in the array are at a sufficiently low density such that the individual molecules can be individually resolved—i.e. when visualised using the method of choice, each molecule can be visualised separately from neighbouring molecules, regardless of the identity of those neighbouring molecules. The required density varies depending on the resolution of the visualisation method. As a guide, molecules are preferably separated by a distance of approximately at least 250, 500, 600, 700 or 800 nm in both dimensions when the arrays are intended for use in relatively low resolution optical detection systems (the diffraction limit for visible light is about 300 to 500 nm). If nearest neighbour single molecules are labelled with different fluors, or their functionalization (see below) can be temporally resolved, then it is possible to obtain higher resolution by deconvolution algorithms and/or image processing. Alternatively, where higher resolution detection systems are used, such as scanning near-field optical microscopy (SNOM), then separation distances down to approx. 50 nm can be used. As detection techniques improve, it may be possible to reduce further the minimum distance. The use of non-optical methods, such as AFM, allows the reduction of the feature-to-feature distance effectively to zero.

Since, for example, during many immobilisation procedures or density reduction procedures, the probability of all molecules being separated by at least the minimum distance required for resolution is low, it is acceptable for a proportion of molecules to be closer than that minimum distance. However, it is preferred that at least 50%, more preferably at least 75, 90 or 95% of the molecules are at the minimum separation distance required for individual resolution.

Furthermore, the actual density of molecules in the array can be higher than the maximum density allowed for individual resolution since only a proportion of those molecules will be detectable using the resolution method of choice. Thus where resolution, for example, involves the use of labels, then provided that individually labelled molecules can be resolved, the presence of higher densities of unlabeled molecules is immaterial.

Hence the individual molecules in the array are at densities normal to bulk analysis but the array is functionalised so that only a subset of molecules, substantially all of which can be individually resolved are analysed. This functionalization can be done before an assay is performed on the array. In other instances, the functionalisation is due to the assay. For example, the assay can be configured so that the amount of sample that is added is so low that interaction only occurs with a fraction of the molecules of the array. Since the label that is detected is specifically associated with the occurrence of these interactions, a low density of molecules is functionalised from a higher density array. Hence a normal density array is effectively an intermediate state before the active product is achieved in which single molecules can be resolved and analysed.

Molecules that can be immobilised in the array include nucleic acids such as DNA and analogues and derivatives thereof, such as PNA. Nucleic acids can be obtained from any source, for example genomic DNA or cDNA or synthesised using known techniques such as step-wise synthesis. Nucleic acids can be single or double stranded. DNA nanostructures or other supramolecular structures can also be immobilised. Other molecules include: compounds joined by amide linkages such as peptides, oligopeptides, polypeptides, proteins or complexes containing the same; defined chemical entities, such as organic molecules, conjugated polymers and carbohydrates or combinatorial libraries thereof In several embodiments, the chemical identity of the molecules must be known or encoded prior to manufacture of the array by the methods of the present invention. For example, the sequence of nucleic acids (or at least all or part of the sequence of the region that is used to bind sample molecules) and the composition and structure of other compounds should be known or encoded in such a way that the sequence of molecules of interest can be determined with reference to a look-up table. The term "spatially addressable", as used herein, therefore signifies that the location of a molecule specifies its identity (and in spatial combinatorial synthesis, the identity is a consequence of location).

Molecules can be labelled to enable interrogation using various methods. Suitable labels include: optically active dyes, such as fluorescent dyes; nanoparticles such as fluorospheres and quantum dots, rods or nanobars; and surface plasmon resonant particles (PRPs) or resonance light scattering particles (RLSs)—particles of silver or gold that scatter light (the size and shape of PRP/RLS particles determines the wavelength of scattered light). See Schultz et al., 2000, PNAS 97: 996-1001; Yguerabide, J. and Yguerabide E., 1998, Anal Biochem 262: 137-156.

In the resulting arrays, it is preferred that molecules are arranged in discrete elements. Generally, each element is adjacent to another or at least 1 µm apart and/or less than 10, 20, 50, 100 or 300 µm apart. The size of the array elements can vary. Because the sensitivity of detection is single molecular, a single array element may contain one or very few probe molecules. In this case the size of element may be at the sub-100 mn level. In other instances where it is necessary to maximise the number of molecules that are counted in a single array element, the microarray element may be in excess of 500 microns. The typical dimensions of a microarray element created by spotting are between 150 and 300 microns. Each element is spatially addressable so the identity of the molecules present in each element is known or can be determined on the basis of a prior coding. Thus if an element is interrogated to determine whether a given molecular event has taken place, the identity of the immobilised molecule is already known by virtue of its position in the array. In a preferred embodiment, only one molecule species is present within each element, in single or multiple copies. Where present in multiple copies, it is preferred that individual molecules are individually resolvable. In one embodiment, elements in the array can comprise multiple species that are individually resolvable. Typically, multiple species are differentially labelled such that they can be individually distinguished. By way of example, an element can comprise a number of different probes for detecting single nucleotide polymorphisms alleles, each probe having a different label such as a different fluorescent dye.

Molecular arrays produced by the methods of the invention preferably comprise at least 10 distinct molecular species, more preferably at least 50 or 100 different molecular species. For gene expression analysis applications, the number of array elements may be ultimately determined by the number of genes. For SNP analysis the number of elements may be determined by the number of SNPs required to adequately sample the diversity of the genome. For sequencing applications the number of elements may be determined by the size the genome is fragmented into, for example for fragments of 50,000 kb, 20,000 elements may be needed to represent all of the genome, and fewer elements would be required to represent the coding regions.

Two possible approaches for manufacturing low density arrays for use in the present invention are outlined below.

i. De Novo Fabrication

In one embodiment of the present invention, low density molecular arrays are produced by immobilising pluralities of molecules of known composition to a solid phase. Typically, the molecules are immobilised onto or in discrete regions of a solid substrate. The substrate can be porous to allow immobilisation within the substrate (e.g. Benoit et al., 2001, Anal. Chemistry 73: 2412-242) or substantially non-porous, in which case the molecules are typically immobilised on the surface of the substrate.

The solid substrate can be made of any material to which the molecules can be bound, either directly or indirectly. Examples of suitable solid substrates include flat glass, quartz, silicon wafers, mica, ceramics and organic polymers such as plastics, including polystyrene and polymethacrylate. The surface can be configured to act as an electrode or a thermally conductive substrate (which enhances the hybridisation or discrimination process). For example, micro and sub-micro electrodes can be formed on the surface of a suitable substrate using lithographic techniques. Smaller, nanoelectrodes can be made by electron beam writing/lithography. Electrodes can also be made using conducting polymers which can be pattern a substrate by ink jet printing devices by soft lithography or be applied homogenously by wet chemistry. $TnO_2$ coated glass substrated are available. Electrodes can be provided at a density such that each immobilised molecule has its own electrode or at a higher density such that groups of molecules or elements are connected to an individual electrode. Alternatively, one electrode may be provided as a layer below the surface of the array which forms a single electrode.

The solid substrate may optionally be interfaced with a permeation layer or a buffer layer. It is also possible to use semi-permeable membranes such as nitrocellulose or nylon membranes, which are widely available. The semi-permeable membranes can be mounted on a more robust solid surface such as glass. The surface layer may comprise a sol-gel. The surfaces may optionally be coated with a layer of metal, such as gold, platinum or other transition metal. A particular example of a suitable solid substrate is the commercially available SPR BIACore™ chip (Pharmacia Biosensors). Heaton et al., 2001 (PNAS 98:3701-3704) have applied an electrostatic field to an SPR surface and used the electric field to control hybridisation.

Preferably, the solid substrate is generally a material having a rigid or semi-rigid surface. In preferred embodiments, at least one surface of the substrate is substantially flat, although in some embodiments it may be desirable to physically separate discrete elements with, for example, raised regions or etched trenches. For example, the solid substrate may comprise nanovials-small cavities in a flat surface e.g. 10 µm in diameter and 10 µm deep. This is particularly useful for cleaving molecules from a surface and performing assays or other processes such as amplification in them. The solution phase reaction is more efficient than the solid phase reaction, whilst the results remains spatially addressable, which is advantageous.

It is also preferred that the solid substrate is suitable for the low density application of molecules such as nucleic acids in discrete areas. It is also advantageous to provide channels to allow for capillary action since in certain embodiments this may be used to achieve the desired straightening of individual nucleic acid molecules. Channels can be in a 2-D arrangement (e.g. Quake S, and Scherer, 200, Science 290: 1536-1540) or in a 3-D flow through arrangement (Benoit et al., 2001, Anal. Chemistry 73: 2412-2420) Channels provide a higher surface area hence a larger number of molecules can be immobilised. In the case of a 3-D flow channel array interrogation can be by confocal microscopy which images multiple slices of the channels in the direction of the z axis.

Furthermore the surface or sub-surface may comprise a functional layer such as a magnetic or a light emitting layer or light transducing layer.

In some instances array elements are raised atop electrodes/electrode arrays. Slides covered with transparent conducting layers such as indium tin oxide (ITO) can be used as substrate for microscopy, including Total Internal Reflection Microscopy (available from BioElectroSpec, PA, USA).

The solid substrate is conveniently divided up into sections. This can be achieved by techniques such as photoetching, or by the application of hydrophobic inks, for example Teflon-based inks (Cel-line, USA).

Discrete positions, in which each different molecules or groups of molecular species are located may have any convenient shape, e.g., circular, rectangular, elliptical, wedge-shaped, etc.

Attachment of the plurality of molecules to the substrate may be by covalent or non-covalent (such as electrostatic) means. The plurality of molecules can be attached to the substrate via a layer of intermediate molecules to which the plurality of molecules bind. For example, the plurality of molecules can be labelled with biotin and the substrate coated with avidin and/or streptavidin. A convenient feature of using biotinylated molecules is that the efficiency of coupling to the solid substrate can be determined easily. Since the plurality of molecules may bind only poorly to some solid substrates, it may be necessary to provide a chemical interface between the solid substrate (such as in the case of glass) and the plurality of molecules. Examples of suitable chemical interfaces include various silane linkers and polyethylene glycol spacer. Another example is the use of polylysine coated glass, the polylysine then being chemically modified if necessary using standard procedures to introduce an affinity ligand. Nucleic acids can be immobilised directly to a polylysine surface (electrostatically). The surface density of the surface charge is important to immobilise molecules in a manner that allows them to be well presented for assays and detection.

Other methods for attaching molecules to the surfaces of solid substrate by the use of coupling agents are known in the art, see for example WO98/49557. The molecules can also be attached to the surface by a cleavable linker.

In one embodiment, molecules are applied to the solid substrate by spotting (such as by the use of robotic microspotting techniques—Schena et al., 1995, Science 270: 467-470) or ink jet printing using for example robotic devices equipped with either ink jets (Canon patent) or piezo electric devices as in the known art.

For example pre-synthesized oligonucleotides dissolved 100 mM NaoH or 2-4×SSC or 50% DMSO, can be applied to glass slides coated with 3-Glycodioxypropyltrimethoxysilane or the ethoxy derivative and then at room temperature for 12-24 hours and then placed at 4 degrees. Advantageously the oligonucleotides can be amino-terminated, but unmodified oligos can also be spotted (These can then be placed at 110-20 degrees for 15 minutes-20 minutes prior to room temperature incubation).

Alternatively amino-terminated oligonucleotides can be spotted onto 3-Aminopropyltrimethoxysilane in 50% DMSO and then UV cross-linked at 300 millijoules. cDNAs or other unmodified DNA can be spotted onto the above slides or onto poly-L-lysine coated slides. 2-4×SSC or 1:1 DMSO:water can be used for spotting. Treatment with UV and succinic anhydride is optional. The slides should be washed, to wash off unbound probes before assays are performed.

Single molecule arrays can be created by spotting dilute solutions. The following are tested protocols for making single molecule arrays.

There are a number of factors that need to be taken into consideration for making single molecule arrays. The primary requirement is of course that the molecules are at such a surface density that single molecules can be individually resolved. General criteria for obtaining the highest quality of microarrays in general should apply here. Spots must be of the highest quality in terms of shape and internal morphology and non-specific background should be low. There must be an even distribution of the single molecules within the spot area and bunching of molecules or internal spot patterns such as the "doughnut" effect which is due to the spot drying process should be minimal. The shape and size of the spots should ideally be fairly similar. The arrangement of the spots should be in regular pattern and out of line spots (spots that have shifted out of register) which seem to occur when slides are kept at high humidity should be avoided.

The slide surface chemistry, spotting process and associated parameters determine the optimal concentration of oligonucleotides that must be provided in the microtitre plate well to obtain single molecule arrays. Therefore the concentration of oligonucleotides in a microtitre plate well needs to be determined empirically when each of the following is varied: the array spotting system (there are many manufacturers of equipment), types of spotting heads (i.e. ink jet, capillary, stealth pins, ring and pin), spotting parameters (e.g. the intensity with which the capillary hits the surface, how much volume is dispensed) slide chemistry, oligonucleotide chemistry and if the oligonucleotide contains any terminal modification and the type and concentration of spotting buffer and humidity during the spotting process.

There are a number of vendors who sell slides with different surface modifications and appropriate buffers, for example Corning (USA), Quantifoil (Jena, Germany), Surrmodics (USA) and Mosaic (Boston, USA).

Immobilisation may also be by the following means: Biotin-oligonucleotide complexed with Avidin, Strepatavidin or Neutravidin; SH-oligonucleotide covalently linked via a disulphide bond to a SH-surface; Amine-oligonucleotide covalently linked to an activated carboxylate or an aldehyde group; Phenylboronic acid (PBA)-oligonucleotide complexed with salicylhydroxamic acid (SHA); Acrydite-oligonucleotide reacted with thiol or silane surface or co-polymerized with acrylamide monomer to form polyacrylamide. Or by other methods known in the art. For some applications where it is preferable to have a charged surface, surface layers can be composed of a polyelectrolyte multilayer (PEM) structure (US2002025529).

Arrays can also be deposited by sealing a microtitre plate against a substrate surface and centrifuging with the sample side of the microtitre plate on top of the surface. This is followed by flipping over and centrifuging with the substrate on top. Single molecule arrays can be created by as short first centrifugation and long second centrifugation. Alternatively, dilute solutions can be deposited by centrifugation.

The required low density is typically achieved by using dilute solutions. One microliter of a $10^{-6}$ M solution spread over a 1 $cm^2$ area has been shown to give a mean intermolecular separation of 12.9 nm on the surface, a distance far too small to resolve with optical microscope. Each factor of 10 dilution increases the average intermolecular separation by a factor 3.16. Thus, a $10^{-9}$ M solution gives a mean intermolecular separation of about 400 nm and a $10^{-12}$ M gives a mean intermolecular separation of about 12.9 µm. With a mean separation of about 12.9 µm, if the molecules are focused to appear to be 0.5 µM in diameter and the average distance is 5 µM, then the chance of two molecules overlapping (i.e. centre to centre distance of 5 µM or less) is about 1% (based on M. Unger E. Kartalov, C. S Chiu, H. Lester and S. Quake, "Single Molecule Fluorescence Observed with Mercury Lamp Illumination", *Biotechniques* 27: 1008-1013 (1999)). Consequently, typical concentrations of dilute solutions used to spot or print the array, where far field optical methods are used for detection is in the order of at least $10^{-9}$ M, preferably least $10^{-10}$ M or $10^{-12}$ M. The concentration used is higher with the use of superresolution far field methods or SPM. It should also be borne in mind that only a fraction of molecules that are spotted onto a surface robustly attach to the surface (0.1% to 1% for example). Thus depending on various spotting and slide parameters, between 1-500 nM of oligonucleotide may be appropriate for spotting onto epoxysilane slides and enhanced aminosilane slides and aminosliane slides. Depending on the method of immobilisation, only a fraction of those molecules that are robustly attached are available for hybridisation or enzymatic assays. For example with the use of amino linked oligonucleotides and spotting onto a Aminopropyltriethoxysilane (APTES) coated slide surface about 20% of the oligonucleotides are available for mini-sequencing.

Before assays are carried out it may be necessary to pretreat the slides to block positions where non-specific binding might occur. Additionally, in for example, primer extension where labelled dNTPs or ddNTPs often stick non-specifically to the surface, it may be necessary to provide a negative charge on the surface, chemically or electronically to repel such molecules.

In a second embodiment, the surface is designed in such a way that sites of attachment (i.e. chemical linkers or surface moieties) are dilute or that sites are selectively protected or blocked. In this case, the, concentration of the sample used for ink jet printing or spotting is immaterial provided the attachment is specific to these sites. In the case of in situ synthesis of molecules, the lower number of available sites for initiating synthesis allows more efficient synthesis providing a higher chance of obtaining full-length products.

Polymers such as nucleic acids or polypeptides can also be synthesised in situ using photolithography and other masking techniques whereby molecules are synthesised in a step-wise manner with incorporation of monomers at particular positions being controlled by means of masking techniques and photolabile reactants. For example, U.S. Pat. No. 5,837,832 describes a method for producing DNA arrays immobilised to silicon substrates based on very large scale integration technology. In particular, U.S. Pat. No. 5,837,832 describes a strategy called "tiling" to synthesise specific sets of probes at spatially-defined locations on a substrate. U.S. Pat. No. 5,837,832 also provides references for earlier techniques that can also be used. Light directed synthesis can also be carried out by using a Digital Light Micromirror chip (Texas Instruments) as described (Singh-Gasson et al., (1999) Nature Biotechnology 17:974-978). Instead of using photo-deprotecting groups which are directly processed by light, conventional deprotecting groups such as dimethoxy trityl can be employed with light directed methods where for example a photoacid is generated in a spatially addressable way which selectively deprotects the DNA monomers (McGall et al PNAS 1996 93: 1355-13560; Gao et al J. Am. Chem Soc. 1998 120: 12698-12699). Electrochemical generation of acid is another means that is being developed (e.g. Combimatrix Corp.)

The size of array elements is typically from 0.1×0.1 microns and above as can be ink jet or spot printed onto a patterned surface or created by photolithography or physical masking. Array elements created by nanolithography such as scanning probe microscopy may be smaller.

Molecules can be attached to the solid phase at a single point of attachment, which can be at the end of the molecule or otherwise. Alternatively, molecules can be attached at two or more points of attachment. In the case of nucleic acids, it can be advantageous to use techniques that 'horizontalize' the immobilised molecule relative to the solid substrate. For example, fluid fixation of drops of DNA has been shown previously to elongate and fix DNA to a derivatised surface such as silane derivatised surfaces. This can promote accessibility of the immobilised molecules for target molecules. Spotting of sample by quills/pins/pens under fast evaporation conditions creates capillary forces as samples dry to elongate molecules. Means for straightening molecules by capillary action in channels have been described by Jong-in Hahm at the Cambridge Healthtech Institutes Fifth Annual meeting on Advances in Assays, Molecular Labels, Signalling and Detection, May 17-18th Washington D.C. Samples can be applied through an array of channels. The density of molecules stretched across a surface is typically constrained by the radius of gyration of the DNA molecule.

A method for making single molecule arrays of any substance may comprise the steps of:
(i) Make a series of microarray spots with a dilution series of molecules over a wide dilution range;
(ii) Analyse to see which spots give single molecule resolution using the desired detection method;
(iii) Optionally repeat (i) and (ii) with a more focused dilution series based on information from (ii); and
(iv) microarrays with the determined dilution.

Spatially Addressable Self-Assembly

Immobilised molecules can also serve to bind further molecules to complete manufacture of the array. For example, nucleic acids immobilised to the solid substrate can serve to capture further nucleic acids by hybridisation, or polypeptides. Similarly, polypeptides can be incubated with other compounds, such as other polypeptides. It may be desirable to permanently "fix" these interactions using, for example UV crosslinking and appropriate cross-linking reagents. Capture of secondary molecules can be achieved by binding to a single immobilised "capture" molecules or to two or more "capture" molecules. Where secondary molecules bind to two or more "capture" molecules, this can have the desirable effect of containing the secondary molecule horizontally.

The secondary molecules of the array can also be made horizontal and straightened out without a second capture probe, by methods such as molecular combing and fibre FISH. One detailed method is described in Examples. This is quite distinct to the arraying fragments of pre-sorted molecules of Junping Jing PNAS Vol. 95, Issue 14, 8046-8051, Jul. 7, 1998 (U.S. Pat. No. 6,221,592) because we have self-assembled the genomic molecules to spatially addressable sites and so it is a way of sorting the genome for highly parallel single molecule analysis. For Schwartz's arrayed spots to represent the whole genome, traditional cloning techniques would need to be used to isolate each individual genome fragment for spotting.

Where this is done, the elements of the array are preferably not immediately adjacent to one another and a gap should exist between each functional array element, because stretched out DNA fibers are expected to stretch out from the edges of the element (and would protrude into immediately adjacent elements). In these cases the separation of the array elements is dictated by the length of molecules that are immobilised. For example, for Lambda DNA the distance separating elements should be 15 to 30 microns at least.

This process can self assemble a secondary array, typically composed of target molecules, upon a spatially addressable array of capture probes. This is a way of sorting out a complex sample such as a genome or a mRNA population and presenting it for further analysis such as haplotyping or sequencing.

ii Density Reduction of High Density Arrays

In an alternative embodiment, the molecular array can be obtained by providing an array produced with molecules at normal (high) densities using a variety of methods known in the art, followed by reduction of surface coverage.

A reduction in actual or effective surface coverage can be achieved in a number of ways. Where molecules are attached to the substrate by a linker, the linker can be cleaved. Instead of taking the cleavage reaction to completion the reaction is partial, to the level required for achieving the desired density of surface coverage. In the case of molecules attached to glass by an epoxide and PEG linkage, such as oligonucleotides, partial removal of molecules can be achieved by heating in ammonia which is known to progressively destroy the lawn.

It is also possible to obtain a reduction in surface coverage by functional inactivation of molecules in situ, for example using enzymes or chemical agents. The amount of enzyme or agent used should be sufficient to achieve the desired reduction without inactivating all of the molecules. Although the end result of this process is often a substrate which has molecules per se at the same density as before the density reduction step, the density of functional molecules is reduced since many of the original molecules have been inactivated. For example, phosphorylation of the 5' ends of 3' attached oligonucleotides by polynucleotide kinase, which renders the oligonucleotides available for ligation assays is only 10% efficient.

An alternative method for obtaining a reduction in molecule density is to obtain an effective reduction in density by labelling or tagging only a proportion of the pre-existing immobilised molecules so that only the labelled/tagged molecules at the required density are available for interaction and/or analysis. This is particularly useful for analysing low target numbers on normal density arrays where the target introduces the label.

These density reduction steps can be applied conveniently to ready-made molecular arrays which are sold by various vendors e.g. Affymetrix, Corning, Agilent and Perkin Elmer. Alternatively, proprietary molecular arrays can be treated as required.

The present invention also provides an "array of arrays", wherein an array of molecular arrays (level 1) as described are configured into arrays (level 2) for the purpose of multiplex analysis. Multiplex analysis can be done by sealing each molecular array (level 1) in individual chambers, that makes a seal with the common substrate, so that a separate sample can be applied to each. Alternatively each molecular array (level 1) can be placed at the end of a pin (as commonly used in combinatorial chemistry) or a fibre and can be dipped into a multi well plate such as a 384 well microtitre plate. The fibre can be an optical fibre which can serve to channel the signal from each array to a detector. The molecular array (level 1) can be on a bead which self-assembles onto a hollow optical fibre as described by Walt and co-workers (Illumina Inc.): Karri et al Anal. Chem 1998 70: 1242-1248. Moreover, the array may be of arrays of randomly immobilised molecules of known and defined type, for example a complete oligonucleotide set of every 17mer or genomic DNA from a particular human sample.

An array of the invention may provide probes for different applications, such as SNP typing and STR analysis as needed for some applications such as typing polymorphisms on the Y Chromosome.

Biosensors

Low density molecular arrays or low density functionalised molecular array may be used in biosensors which may be used to monitor single molecule assays on a substrate surface, such as a chip. The array may comprise, for example, between 1 and 100 different immobilised molecules (e.g. probes), an excitation source and a detector such as a CCD, all within an integrated device. Sample processing may or may not be integrated into the device.

In one aspect, the biosensor would comprise a plurality of elements, each element containing distinct molecules, such as probe sequences. Each element may then be specific for the detection of, for example, different pathogenic organisms.

In a preferred embodiment the immobilised molecules would be in the form of molecular beacons and the substrate surface would be such that an evanescent wave can be created at the surface. This may be achieved by the forming a grating structure on the substrate surface or by making the array on an optical fibre (within which light is totally internally reflected) for example. The CCD detector may be placed below the array surface or above the array, separated from the surface by a short distance to allow space for the reaction volume.

Figure 5A:
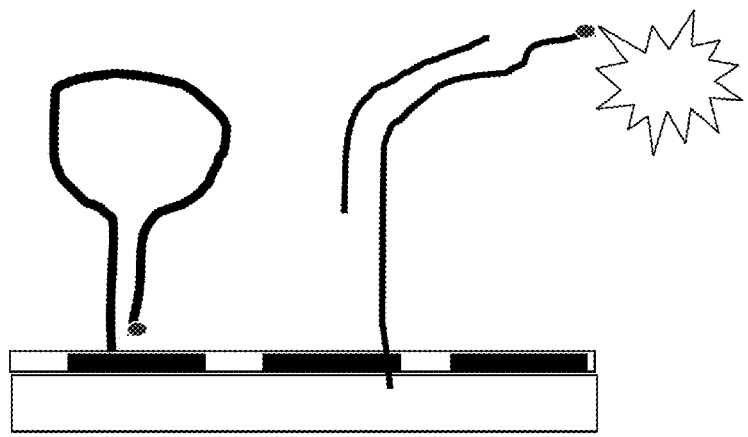
FIGS. 5A, 5B and 5C illustrate using an exemplary biosensor array according to the invention.
Figure 5B:
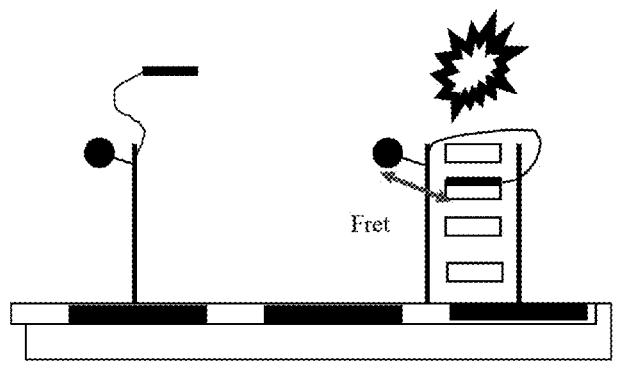
Figure 5C:
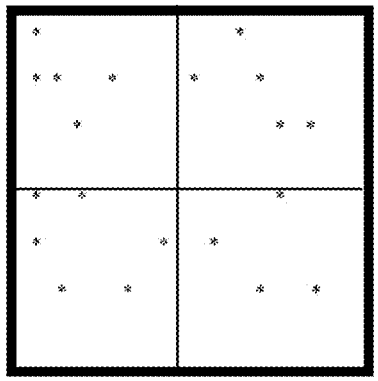
Figure 6A:
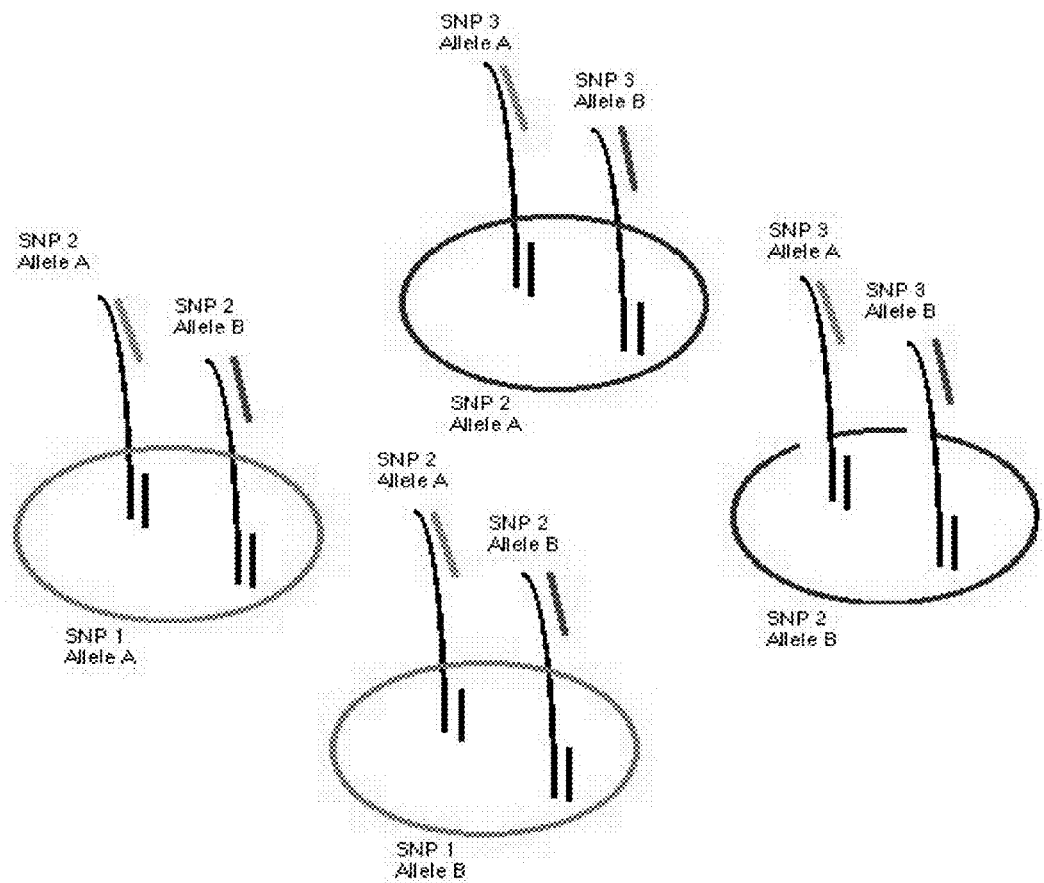
FIGS. 6A and 6B illustrate exemplary SNP detection.
Figure 6B:
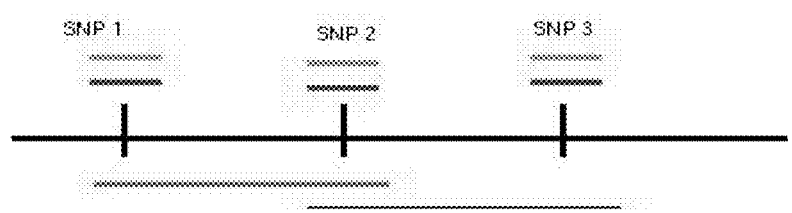

Examples of biosensor configurations are given in figures where: FIG. 5A is an integrated detection scheme based on Fluorescence Energy Resonance Transfer (FRET). The sample is applied between two plates, one with a CCD and the other with an LED with grating structure on its surface. FIG. 5B is an integrated detection system with a molecular beacon (Tyagi et al Nat. Biotechnol. 1998, 16:49-53) on an optical fibre.

Single molecules can be viewed on stripped fused silica optical fibres, essentially as described by Watterson et al. (Sensors and Actuators B 74: 27-36 (2001). Molecular Beacons can be seen in the same way (Liu et al. (2000) Analytical Biochemistry 283: 56-63). This is the basis of a biosensor device based on single molecule analysis in an evanescent field.

B. Interrogation/Detection Methods

Individual molecules in the array and their interaction with target molecules can be detected using a number of means. Detection can be based on measuring, for example physicochemical, electromagnetic, electrical, optoelectronic or electrochemical properties, or characteristics of the immobilised molecule and/or target molecule.

There are two factors that are pertinent to single molecule detection of molecules on a surface. The first is achieving sufficient spatial resolution to resolve individual molecules. The density of molecules is such that only one molecule is located in the diffraction limit spot of the microscope which is ca. 300 nm. Low signal intensities reduce the accuracy with which the spatial position of a single molecule can be determined. The second is to achieve specific detection of the desired single molecules as opposed to background signals.

Scanning probe microscopy (SPM) involves bringing a probe tip into intimate contact with molecules as the tip is scanned across a relatively flat surface to which the molecules are attached. Two well-known versions of this technique are scanning tunneling microscopy (STM) and atomic force microscopy (AFM; see Moeller et al., 2000, NAR 28: 20, e91)

in which the presence of the molecule manifests itself as a tunnel current or a deflection in the tip-height of the probe, respectively. AFM can be enhanced using carbon nanotubes attached to the probe tip (Wooley et al., 2000, Nature Biotechnology 18:760-763). An array of SPM probes which can acquire images simultaneously are being developed by many groups and can speed the image acquisition process. Gold or other material beads can be used to help scanning probe microscopy find molecules automatically.

Electron microscopy can also be used to interrogate arrays.

Optical methods based on sensitive detection of absorption or emission can be used. Typically optical excitation means are used to interrogate the array, such as light of various wavelengths, often produced by a laser source. A commonly used technique is laser-induced fluorescence. Although some molecules are sufficiently inherently luminescent for detection, generally molecules in the array (and/or target molecules) need to be labelled with a chromophore such as a dye or optically active particle (see above). If necessary, the signal from a single molecule assay can, for example, be amplified by labelling with dye loaded nanoparticles, or multi-labelled dendrimers or PRPs/SPRs. Raman spectroscopy is another means for achieving high sensitivity.

Plasmon resonant particles (PRPs) are metallic nanoparticles which scatter light elastically with remarkable efficiency because of a collective resonance of the conduction electrons in the metal (i.e. the surface plasmon resonance). PRPs can be formed that have scattering peak anywhere in the visible range of the spectrum. The magnitude, peak wavelength and spectral bandwidth of the plasmon resonance associated with a nanoparticle are dependent on a particle's size, shape and material composition, as well as local environment. These particles can be used to label a molecule of interest. SERS [Surface-enhanced Raman Scattering] on nanoparticles exploit raman vibrations on metallic nanoparticles of the single molecules themselves and can be used to amplify their spectroscopic signatures.

Further, many of these techniques can be applied to fluorescence resonance energy transfer (FRET) methods of detecting interactions where, for example, the molecules in the array are labelled with a fluorescent donor and the target molecules (or reporter oligonucleotides) are labelled with a fluorescent acceptor, a fluorescent signal being generated when the molecules are in close proximity. Moreover, structures such as molecular beacons where the FRET donor and acceptor (quencher) are attached to the same molecule can be used.

The use of dye molecules encounters the problems of photobleaching and blinking. Labelling with dye-loaded nanoparticles or surface plasmon resonance (SPR) particles reduces the problem. However a single dye molecule bleaches after a period of exposure to light. The photobleaching characteristics of a single dye molecule have been used to advantage in the single molecule field as a means for distinguishing signal from multiple molecules or other particles from the single molecule signal.

Spectroscopy techniques require the use of monochromatic laser light, the wavelength of which varies according to the application. However, microscopy imaging techniques can use broader spectrum electromagnetic sources.

Optical interrogation/detection techniques include near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques can also be used in a spectroscopic mode. The actual detection means include charge coupled device (CCD) cameras and intensified CCDs, photodiodes and photomultiplier tubes. These means and techniques are well-known in the art. However, a brief description of a number of these techniques is provided below.

Near-Field Scanning Microscopy (NSOM)

In NSOM, subdiffraction spatial resolutions in the order of 50-100 nm are achieved by bringing a sample to within 5-10 nm of a subwavelength-sized optical aperture. The optical signals are detected in the far field by using an objective lens either in the transmission or collection mode (see Barer, Cosslett, eds 1990, Advances in Optical and Electron Microscopy. Academic; Betzig, 1992, Science 257: 189-95). The benefits of NSOM are its improved spatial resolution and the ability to correlate spectroscopic information with topographic data. The molecules of the array need to either have an inherent optically detectable characteristic such as fluorescence, or be labelled with an optically active dye or particle, such as a fluorescent dye. It has been proposed that resolution can be taken down to just a few nanometers by scanning apertureless microscopy (Scanning Interferometric Apertureless Microscopy: Optical Imaging at 10 Angstrom Resolution" F. Zenhausem, Y. Martin, H. K. Wickramasinghe, Science 269, p. 1083; T. J. Yang, G. A. Lessard, and S. R. Quake, "*An Apertureless Near-Field Microscope for Fluorescence Imaging*", Applied Physics Letters 76: 378-380 (2000).

Alternatively excitation can be limited to the near field by a scanning probe or a narrow slit in near-field proximity to the sample. Acquisition can be in the far field (Tegenfeldt et al., 2001, Physical Review Letters 86: 1378-1381).

Far-Field Confocal Microscopy

In confocal microscopy, a laser beam is brought to its diffraction-limited focus inside a sample using an oil-immersion, high-numerical-aperture objective. The fluorescent signal emerging from a 50-100 μm region of the sample is measured by a photon counting system and displayed on a video system (for further background see Fawley J. B., ed 1995, Handbook of Biological Confocal Microscopy). Improvements to the photon-counting system have allowed single molecule fluorescence to be followed in real time (see Nie et al., 1994, Science 266: 1018-21). A further development of far-field confocal microscopy is two-photon (or multi-photon) fluorescence microscopy, which can allow excitation of molecules with different excitation wavelengths with single higher wavelength source (the molecule undertakes multiple lower energy excitations see for example, Mertz et al., 1995, Opt. Lett. 20: 2532-34). The excitation is also very spatially localised.

Wide-Field Epi-Illumination

The optical excitation system used in this method generally consists of a laser source, defocusing optics, a high performance dichroic beamsplitter, and an oil-immersion, low autofluorescence objective. Highly sensitive detection is achieved by this method using a cooled, back-thinned charge-coupled device (CCD) camera or an intensified CCD (ICCD). High-powered mercury lamps can also be used to provide more uniform illumination than is possible for existing laser sources. The use of epi-fluorescence to image single myosin molecules is described in Funatsu et al., 1995, Nature 374: 555-59.

Evanescent Wave Excitation

At the interface between glass and liquid/air, the optical electromagnetic field decays exponentially into the liquid phase (or air). Molecules in a thin layer of about 300 nm immediately next to this interface can be excited by the rapidly decaying optical field (known as an evanescent wave). A molecule intimate to the surface feels the field more than one that is close to 300 nm away. A description of the use of evanescent wave excitation to image single molecules is provided in Hirschfeld, 1976, Appl. Opt. 15: 2965-66 and Dickson et al., 1996, Science 274: 966-69. The imaging set-up for evanescent wave excitation typically includes a microscope configured such that total internal reflection occurs at the glass/sample interface (Axelrod D. Methods on Cell Biology 1989 30: 245-270). Alternatively a periodic optical microstructures or gratings can provide evanescent wave excitation at the optical near-field of the grating structures. This serves to increase array signals around 100 fold (surface planar waveguides have been developed by Zeptosens, Switzerland; similar technology has been developed by Wolfgag Budach et al., Novartis AG, Switzerland—poster at Cambridge Healthtech Institutes Fifth Annual meeting on "Advances in Assays, Molecular Labels, Signalling and Detection). Preferably an intensified CCD is used for detection.

Superresolution Far-Field Optical Methods

Superresolution far-field optical methods have been highlighted by Weiss, 2000 (PNAS 97: 8747-8749). One new approach is point-spread-function engineering by stimulated emission depletion (Klar et al 2000, PNAS 97: 8206-8210) which can improve far-field resolution by 10 fold. Distance measurement accuracy of better than 10 nm using far field microscopy, can be achieved by scanning a sample with nanometer size steps using a piezo-scanner (Lacoste et al PNAS 2000 97: 9461-9466). The resulting spots are localised accurately by fitting then to the known shape of the excitation point-spread function of the microscope. Similar measurement capabilities by circular scanning of the excitation beam are known. Shorter distances can typically be measured by molecular labelling strategies utilising FRET (Ha et al Chem. Phys. 1999 247: 107-118) or near field methods such as SPM. These distance measurement capabilities are useful for the sequencing applications proposed in this invention.

Microarray Scanners

The burgeoning microarray field has introduced a plethora of different scanners based on many of the above described optical methods. These include scanners based on scanning confocal laser, TIRF and white light for illumination and Photomultiplier tubes, avalanche photodiodes and CCDs for detection. However, commercial array scanners in their standard form are not sensitive enough for SMD and the analysis software is inappropriate.

Since the molecular arrays of the invention are spatially addressable, any immobilised molecule of interest/element of interest can be interrogated by moving the substrate comprising the array to the appropriate position (or moving the detection means). In this way as many or as few of the elements in the array can be read and the results processed. x-y stage translation mechanisms for moving the substrate to the correct position are available for use with microscope slide mounting systems (some have a resolution of 100 mm). Movement of the stage can be controlled automatically by computer if required. Ha et al (Appl. Phys. Lett. 70: 782-784 (1997)) have described a computer controlled optical system which automatically and rapidly locates and performs spectroscopic measurements on single molecules. A galvanometer mirror or a digital micromirror device (Texas Instruments, Houston) can be used to enable scanning of the image from a stationary light source. Signals can be processed from the CCD or other imaging device and stored digitally for subsequent data processing.

Multicolour Imaging

Signals of different wavelength can be obtained by multiple acquisitions or by simultaneous acquisition by splitting the signal, using RGB detectors or analysing the whole spectrum (Richard Levenson, Cambridge Healthtech Institutes, Fifth Annual meeting on Advances in Assays, Molecular Labels, Signalling and Detection, May 17-18th Washington D.C.). Several spectral lines can acquired by the use of a filter wheel or a monochromater. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

The Problem of Background Fluorescence

Microscopy and array scanning are not typically configured for single molecule detection. The fluorescence collection efficiency must be maximized and this can be achieved with high numerical aperture (NA) lenses and highly sensitive electro-optical detectors such as avalanche diodes that reach quantum yields of detection as high as 0.8 and CCDs that are intensified (e.g I-PentaMAX Gen III; Roper Scientific, Trenton, N.J. USA) or cooled (e.g. Model ST-71 (Santa Barbara Instruments Group, CA, USA). However, the problem is not so much the detection of fluorescence from the desired single molecule (single fluorophores can emit ~$10^8$ photons/sec) but the rejection of background fluorescence. This can be done in part by only interrogating a minimal volume as done in confocal, two-photon and TIRF microscopy. Traditional spectral filters (e.g. 570DF30 Omega Filters) can be applied to reduce the contribution from surrounding material (largely Rayleigh and Raman scattering of the excitation laser beam by the solvent and fluorescence from contaminants).

To reduce background fluorescence to levels which allow legitimate signal from single molecules to be detected a pulsed laser illumination source synchronized with a time gated low light level CCD can be used (Enderlein et al in: Microsystem technology: A powerful tool for biomolecular studies; Eds.: M. Köhler, T. Mejevaia, H. P. Saluz (Birkhäuser, Basel, 1999) 311-29)). This is based on the phenomenon that after a sufficiently short pulse of laser excitation the decay of the analyte fluorescence is usually much longer (1-10 ns) than the decay of the light scattering (~$10^2$ ps). Pulsing of a well chosen laser can reduce the background count rate so that individual photons from individual fluorophores can be detected. The laser power, beam size and repetition rate must be appropriately configured. A commercial array scanner and its software can be customized (Fairfield Enterprises, USA) so that robust single molecule sensitivity can be achieved. Alternatively, Time Correlated Single-Photon Counting (TCSPC) can be used to gather all the fluorescent emission after a pulsed exciton and then sort out the background emission from the target emission by their temporal profile. Suitable commercial instruments are available (e.g. LightStation, Atto-tec, Heidelberg, Germany).

In addition to these methods that combat fluorescence noise from within the sample volume, the instrument itself can contribute to background noise. Such thermoelectronic noise can be reduced for example by cooling of the detector. Coupling SPM measurements with optical measurements allows correlation of signals optically detected to the targeted structures rather than those due to other sources. Spatial or temporal correlation of signal from two (fluorescent) probes targeting the same molecule suggests the desired rather than extraneous signal (e.g. Castro and Williams, Anal Chem. 1997 69: 3915-3920). A FRET based detection scheme also facilitates rejection of background.

Low fluorescence immersion oils are preferably used, as are substrates that are ultra-clean and of low intrinsic fluorescence. Glass slides/coverslips are preferably of high quality and well cleaned (e.g. with detergents such as Alconex and Chromerge (VWR Scientific, USA) and high purity water). Preferably, a substrate such as fused quartz or pure white glass is used, which has a low intrinsic fluorescence. Single fluorophores can be distinguished from contaminating particles by several features: spectral dependence, concentration dependence, quantized emission and blinking. Particulate contaminants usually have broad spectrum fluorescence which is obtained in several filter sets whereas single fluorephores are only visible in specific filter sets.

The signal to noise ratio can also be improved by using labels with higher signal intensities such as fluospheres (Molecular Probes Inc.) or multilabelled dendrimers.

Oxygen scavengers can be placed into the medium to prevent photobleaching. Suitable oxygen scavanges include, for example, glycine DTT, mercaptoethanol, glycerol etc.

Label Free Detection.

A number of physical phenomena can be adapted for detection, that rely on the physical properties of the immobilised molecules alone or when complexed with captured targets or that modify the activity or properties of some other elements. For example, terahertz frequency allows the difference between double stranded and single stranded DNA can be detected; Brucherseifer et al., 2000, Applied Physics Letters 77: 4049-4051. Other means include interferometry, elliposometry, refraction, the modification of the signal from a light emitting diode integrated into the surface, native electronic, optical (e.g. absorbance), optoelectronic and electrochemical properties, a quartz crystal microbalance and various modes of AFM which can detect differences on the surface in a label free manner.

To interrogate each array element, the excitation beam can be scanned over the surface or the beam can remain stationary and the sample stage can be moved.

C. Processing of Raw Data and Means for Error Limitation

Digital Analysis of Signals

Discrete groups of assay classification (e.g. nucleotide base calling) can be defined by various measures. A set of unique parameters are chosen to define each of several discrete groups. The result of interrogation of each individual molecule can be assigned to one of the discrete groups. One group can be assigned to represent signals that do not fall within known patterns. For example there may be groups for real base additions, a, c, g, and t in extension assays.

One of the prime reasons that single molecule resolution techniques are set apart from bulk methods is that they allow access to the behaviour of individual molecules. The most basic information that can be obtained is the frequency of occurrence of hits to a particular group. In bulk analysis the signal is represented in analogue by an (arbitrary) intensity value (from which a concentration may be inferred) and this indicates the result of the assay in terms of, say, a base call or it may indicate the level of a particular molecule in the sample, by virtue of its calibrated interaction profile (or its relative level in one sample compared with another sample). In contrast, the single molecule approach enables direct counting and classification of individual events.

A general algorithm for single molecule counting, once the single molecules have been labelled by for example thresholding, is:

Loop through all pixels, $p(x,y)$ left to right, top to bottom
If $p(x,y)=0$, do nothing
If $p(x,y)=1$, add to counter The methods of this invention require basic image processing operations and counting, measuring and assignment operations to be performed on the raw images that are obtained. The invention includes the adaptation and application of general methods including software and algorithms, known in the art for digital signal processing, counting, measuring and making assignments from the raw data. This includes Bayesian, heuristic, machine learning and knowledge based methods.

Moreover, digital data processing facilitates error correction and temporal resolution of reactions at the array surface. Thus, time-resolved microscopy techniques can be used to differentiate between bona-fide reactions between probe and sample and "noise" due to aberrant interactions which take place over extended incubation times. The use of time-gated detection or time-correlated single-photon counting is particularly preferred in such an embodiment.

The invention accordingly provides a method for sorting signals obtained from single molecule analysis according to the confidence with which the signal may be treated. A high confidence in the signal leads to the signal being added to a PASS group and counted; signals in which confidence is low are added to a FAIL group and discarded, or used in error assessment and as a resource for assay design (for example the propensity of a particular primer sequence to give rise to errors in primer extension, can be used to inform primer design in future experiments.

Table 1 illustrates the processing of signals for error analysis by example, for SNP typing by primer extension. The object of the process represented by the flowchart is to eliminate errors from the acquired image. The input for the process is one of the four colours (representing each of four differentially labelled ddNTPs) from the acquired image (after beam splitting). This process is performed on each of the four split signals.

Signals that satisfy a number of criteria are put into a PASS table. This PASS table is the basis for base calling after counting the number of signals for each colour.

The FAIL table is made so that information about error rate can be gathered. The five different types of errors can be collected into separate compartments in the FAIL table so that the occurrence of the different types of error can be recorded. This information may aid experimental methods to reduce error, for example it can reveal which is the most common type of error. Alternatively, the failed signals can be discarded.

The five criteria that are used to assess errors are:

1. If intensity is less than p where p=a minimum threshold intensity. This is high pass filter to eliminate low fluorescence intensity artifacts
2. If intensity is less than q, where q=a maximum intensity threshold. This is a lowpass filter to eliminate high fluorescence intensity artefacts.
3. If time is less than x where x=early time point. This is to eliminate signals due to self-priming which can occur early.
4. If time is greater than z, where z=late timepoint. This is to eliminate signals due to mis-priming of nucleotides which the enzyme can incorporate over an extended period. For example this can be due to priming by template on template which is a two-step process, involving hybridisation of the first template to array and then hybridisation of the second template molecule to the first template molecule.
5. Nearest neighbour pixels are compared to eliminate those in which signal is carried over multiple adjacent pixels which is indicative of signals from, for example, non-specific adsorption of clumps or aggregates of ddNTPs.

The reaction is controlled by adjusting reaction components, for example salt concentration, ddNTP concentration, temperature or pH such that the incorporations occur within the time window analysed A subroutine can be included to check that the fluorescence shows single-step photobleaching characteristic, but ignoring short-scale fluctuations which are likely to be due to blinking.

If a single dye molecule, which photobleaches after a time, is associated with each ddNTP, then an additional sub-process/routine can be added which eliminates signals that after an initial burst re-occur in the same pixel after such a number of time points that the absence cannot be attributed to blinking. This is likely to be non-specific absorption at the same foci as a legitimate extension.

A sub-routine can be included to eliminate any fluorescence that occurs in multiple filters, above the level expected for the dye being analysed Fluorescence due to a single dye molecule can be distinguished from particulate contamination by analysing the concentration dependence of the signal. This can be done if each sequence is arrayed at two or more concentrations. Signals that remain at equal concentration across the array dilution are artefacts, real signals are those whose frequency changes in line with changes in array probe concentration.

If the array is composed of elements an additional process can be used to organise the data into groupings representing the array elements.

Figure 11:
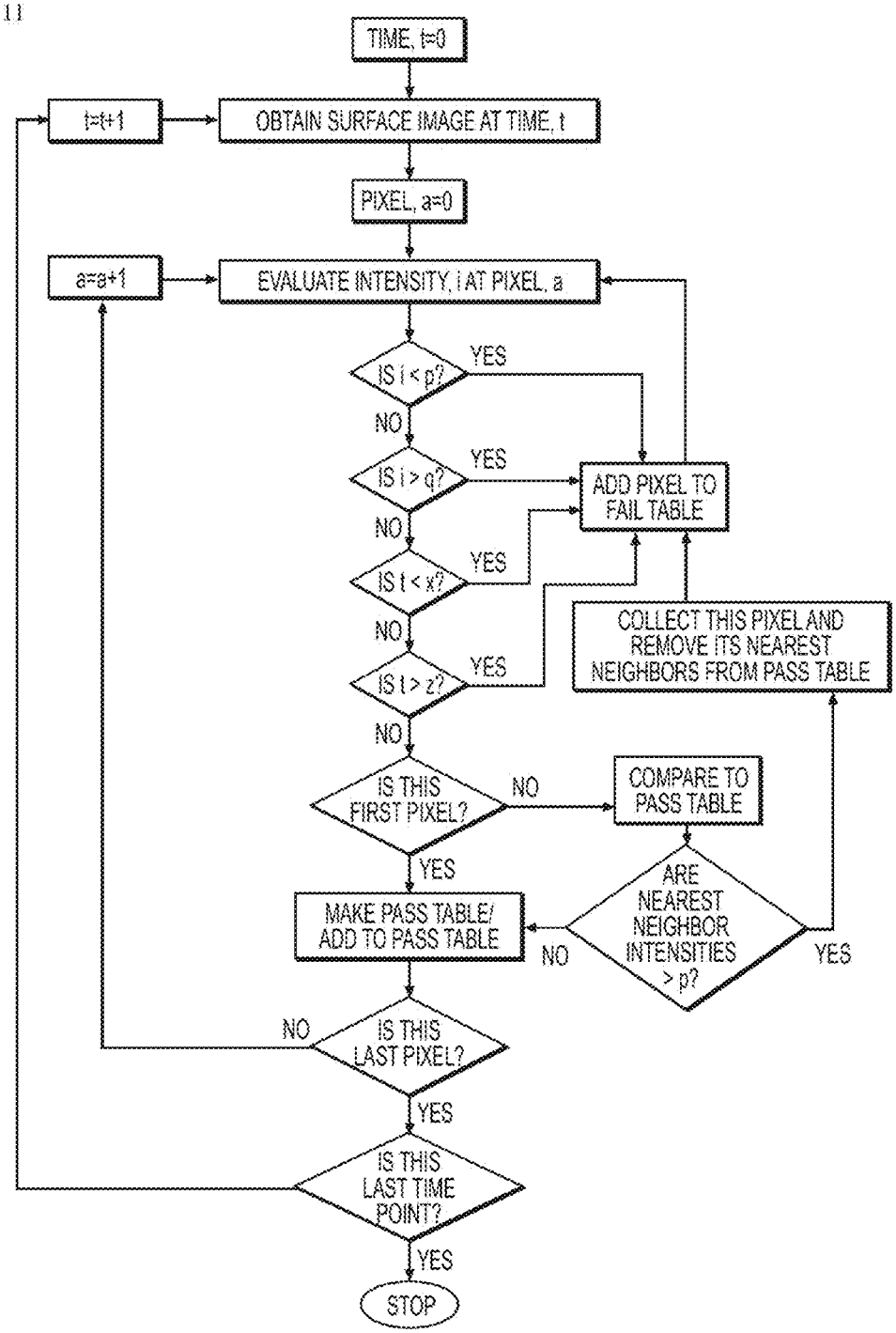
FIG. 11 shows an exemplary scheme describing a system configured such that a single pixel measures a single molecule event.

In the scheme described the system is configured such that a single pixel measures a single molecule event (statistically, in the large majority of cases). The system can be set up, for example, such that several pixels are configured to interrogate a single molecule (FIG. 11).

Thus, in a preferred embodiment, the invention relates to a method for typing single nucleotide polymorphisms (SNPs) and mutations in nucleic acids, comprising the steps of:
a) providing a repertoire of probes complementary to one or more nucleic acids present in a sample, which nucleic acids may possess one or more polymorphisms;
b) arraying said repertoire on to a solid surface such that each probe in the repertoire is resolvable individually;
c) exposing the sample to the repertoire and allowing nucleic acids present in the sample to hybridise/process with enzymes to the probes at a desired stringency such that hybridised/processed with enzymes nucleic acid/probe pairs are detectable;
d) imaging the array in order to detect individual target nucleic acid/probe pairs;
e) analysing the signal derived from step (d) and computing the confidence in each detection event to generate a PASS table of high-confidence results; and
f) displaying results from the PASS table to type polymorphisms present in the nucleic acid sample.

Preferably, the confidence in each detection event is computed in accordance with Table 1.

Advantageously, detection events are generated by labelling the sample nucleic acids and/or the probe molecules, and imaging said labels on the array using a suitable detector. Preferred labelling and detection techniques are described herein.

Methods for Reducing Errors

Single molecule analysis allows access to specific properties and characteristics of individual molecules and their interactions and reactions. Specific features of the behaviour of a particular molecular event on a single molecule may belie information about its origin. For enzymatic assays, for example, there may be a slower rate of mis-incorporations than correct incorporations. Another example is that there may be a different rate of incorporations for self-priming compared to priming in which the target forms the template. The rate characteristics of self-priming are likely to be faster than from priming of sample. This is because self-priming is a unimolecular reaction whereas priming of sample DNA is bimolecular. Therefore if time-resolved microscopy is performed, the time-dependence of priming can distinguish self-priming and mis-priming from correct sample priming. Alternatively, it might be expected that DNA priming from the perfectly matched sample has the capacity to incorporate a greater number of fluorescent dye NTPs in a multi-primer primer extension approach (Dubiley et al., Nucleic Acids Research 1999 27: el 9i-iv) than mis-priming and a self-priming and so gives a higher signal level or molecular brightness.

It can be difficult to differentiate between correct incorporation and mis-incorporation in the mini-sequencing (multi-base approach) because even though a wrong base may take longer to incorporate it may be associated with the primer for the same length of time as the correctly incorporated base. In order to address this problem, if the fluorescence intensity of a ddNTP is quenched to some degree when it is incorporated then the molecular brightness/fluorescence intensity can be used to distinguish between mis-incorporation, which takes longer to become fixed, and correct incorporation.

Different means for reduction of errors can be engineered into the system. For example, in genetic analysis, FRET probes can be integrated at the allelic site. The conformation of a perfect match allows the fluorescent energy to be quenched whereas the conformation of a mismatch does not. The FRET probes can be placed on a spacer, which can be configured to accentuate the distances of FRET probes between matched and mismatched base pair sets.

Mismatch errors can be eliminated in some cases by cleavage with enzymes such as Ribonuclease A. This enzyme cleaves mismatches in RNA:DNA heteroduplexes (Myers R M, Larin Z, Maniatis T. Science 1985 Dec. 13; 230(4731): 1242-6)

In primer extension, the enzyme, Apyrase, a nucleotide degrading enzyme, can be employed for accurate discrimination between matched and mismatched primer-template complexes. The apyrase-mediated allele-specific extension (AMASE) protocol allows incorporation of nucleotides when the reaction kinetics are fast (matched 3'-end primer) but degrades the nucleotides before extension when the reaction kinetics are slow (mismatched 3'-end primer) (Ahmadian et al Nucleic Acids Research, 2001, Vol. 29, No. 24 e121).

In addition to false positive errors discussed above, false negatives can be a major problem in hybridisation based assays. This is particularly the case when hybridisation is between a short probe and a long target, where the low stringency conditions required to form stable heteroduplex concomitantly promotes the formation of secondary structure in the target which masks binding sites. The effects of this problem can be reduced by fragmenting the target, incorporating analogue bases into target (eg incorporating into the target analogue bases that cannot pair with each other but can pair with natural DNA bases of the probe) or probe, manipulating buffers etc Enzymes can help reduce false negatives by trapping transient interactions and driving the hybridisation reaction forward (Southern, Mir and Shchepinov, 1999, Nature Genetics 21: s5-9). This effect can also be achieved by cross-linking psoralen labelled probes to their target molecules. However, it is likely that false negatives will remain to some level. As previously mentioned, because large-scale SNP analysis without the need for PCR is enabled the fact that some SNPs do not yield data is not a major concern. For smaller scale studies, effective probes may need to be pre-selected.

In cases where the amount of sample material is low, special measures must be taken to prevent sample molecules from sticking to the walls of the reaction vessel and other vessels used for handling the material. These vessels can be silanised to reduce sticking of sample material and/or can be treated in advance with blocking material such as Denhardt's reagent or tRNA.

Managing Haplotyping Errors

When performing haplotyping studies (see section D2) the position along the captured target molecule of the SNP sites that will be interrogated is known (unless there are duplications or deletions in between SNPs). In some cases it may be that all the probes have bound to their SNP sites. Zhong et al (PNAS 98: 3940-3945) used Rolling circle amplification (RCA) to visualize haplotypes on FISH fibers state that many of the fibers show the binding of oligonucleotide probes to three contiguous sites along the molecule. However very often every probe will not bind to its complementary sequence and there may be gaps in the string of sites along the molecule. However, as a population of molecules will be available for analysis, the correct information about the SNP allele at each of the sites can be reconstructed algorithmically from the information obtained from all the molecules of a particular species that have been captured on the spatially addressable single molecule array.

In one embodiment the image of the fibers and the bound probes will be acquired and then the information processed.
1. Capture image in and around each array element
2. Process information offline There are image processing packages that are specific for this kind of application.

In another embodiment machine vision will be used to find and track along single molecules with the option of processing information during the process ("on the fly").

The following lists show the steps that would form the basis of a computer program for removing erroneous strands from the analysis and passing on good information to the sequence reconstruction program.
1. Go to a particular microarray element
2. Download prior data about expected positional arrangement of SNPs along strands expected to be captured in that element
3. Recognise Fibres/strands (end markers may aid this)
4. Recognise markers (e.g end markers)
5. Visualise position of probes along molecule
6. Estimate distance separating probes (markers can aid this)
7. Evaluate if the distance separating consecutive probes agrees with expected
8. If probes are at the expected separations for a given fibre go to 10
9. If not then
a. If absence of probe binding, ignore fiber
b. If completely aberrant binding pattern, ignore fibre/add to fail table
c. If gaps in SNP sites, gather information that is present, go to 10
10. Determine identity of label at each position where binding occurs, go to 11
11. Add identity of label to reconstruction algorithm See Digital Image Processing, Rafael C. Gonzalez, Richard E. Woods, Pub: Addison-Wesley.

Reconstruction Algorithm

The reconstruction algorithm will overlap the data from the fibres and will evaluate if there are one (homozygote for the haplotype) or two (heterozygote for the haplotype) haplotypes present and what they are. In the case of pooled DNA there may be the possibility of more than two different haplotypes.

It may be that the wrong strand has been captured by the array probes. It will be simple to weed out such instances because it is unlikely that the haplotype probes will hybridise to such a molecule and if they do then it will be to aberrant positions along the molecule, which can be identified. The greater problem will be when a non-functional duplicate of the sequence (e.g pseudogene) becomes captured. This may indicate different alleles within the haplotype than the functional copy of the sequence. Although this kind of occurrence can be detected when it is rare, it will be more difficult when it competes effectively with the functional sequence. This kind of error can be managed, however, by the prior knowledge about the organisation of the genome and the occurrence of duplications within the genome. Regions of the genome that are known to be duplicated may be avoided or their contribution will be accounted for.

Precise physical distances can be computed. The use of markers other than the labels may aid this, for example marking the ends of the molecule or other sites, including SNP sites with markers that can be distinguishable from the 2-colour SNP tags used for the majority of SNPs.

In some cases, despite stringency control, the probe may have bound but it may be a mismatch interaction. However, because of its relative rarity in the population of single molecules that are analysed it can be ignored (or added to a list of alleles that give erroneous interactions, for future reference). In Pooled DNA or when the sample is from a heterogeneous sample of cell the assay may have to allow for a small degree of error of this kind. For example, the accuracy with which the frequency of a rare allele is obtained may be 1 in a 1000+/−1.

The error management approaches outlined here may also be relevant to fingerprinting and re-sequencing (see section D3) in some instances.

Alternative Methods for Detection and Decoding of Results

The molecules can be detected, as mentioned above, using a detectable label or otherwise, and correlating the position of the label on an array with information about the nature of the arrayed probe to which the label is bound. Further detection means may be envisaged, in which the label itself provides information about the probe which is bound without requiring positional information. For example, each probe sequence can be constructed to comprise unique fluorescent or other tags (or sets thereof), which are representative of the probe sequence. Such encoding can be done by stepwise co-synthesis of probe and tag by split and pool combinatorial chemistry. Ten steps generate every 10mer encoded oligonucleotide (around 1 million sequences). 16 steps generates every 16mer encoded oligonucleotides (around 4 billion sequences) which is expected to occur only once in the genome. Fluorescent tags that are used for encoding can be of different colours or different fluorescent lifetimes. Moreover, unique tags can be attached to individual single molecule probes and used to isolate molecules on anti-tag arrays. The anti tag arrays may be spatially addressable or encoded.

D. Assay Techniques and Uses

A further aspect of the present invention relates to assay techniques based on single molecule detection. These assays can be conducted using molecular arrays produced by the methods of the invention or by any other suitable means.

The spatial addressable array is a way of capturing and organizing molecules. The molecules can then be assayed in a plethora of ways, including using any assay method which is suitable for single molecule detection, such as those described in WO0060114; U.S. Pat. No. 6,210,896; Watt Webb, Research Abstract: New Optical Methods for Sequencing Individual Molecules of DNA, DOE Human Genome Program Contractor-Grantee Workshop III, on Feb. 5, 2001.

In general, the assay methods of the invention comprise contacting a molecular array with a sample and interrogating all or part of the array using the interrogation/detection methods described above. Alternatively, the molecular array is itself the sample and is subsequently interrogated directly or with other molecules or probes using the interrogation/detection methods described above.

Many assay methods rely on detecting binding between immobilised molecules in the array and target molecules in the sample. However other interactions that may be identified include, for example, interactions that may be transient but which result in a modification to the properties of an immobilised molecule in the array, such as charge transfer.

Once the sample has been incubated with the array for the desired period, the array can simply be interrogated (following an optional wash step). However, in certain embodiments, notably nucleic acid-based assays, the captured target molecules can be further processed or incubated with other reactants. For example, in the case of antibody-antigen reactions, a secondary antibody which carries a label can be incubated with the array containing antigen-primary antibody complexes.

Target molecules of interest in samples applied to the arrays can include nucleic acids such as DNA and analogues and derivatives thereof, such as PNA. Nucleic acids can be obtained from any source, for example genomic DNA or cDNA or synthesised using known techniques such as stepwise synthesis. Nucleic acids may be single or double stranded. Other molecules include: compounds joined by amide linkages such as peptides, oligopeptides, polypeptides, proteins or complexes containing the same; defined chemical entities, such as organic molecules; combinatorial libraries; conjugated polymers, lipids and carbohydrates.

Due to the high sensitivity of the approach specific amplification steps can be eliminated if desired. Hence, in the case of analysis of SNPs, extracted genomic DNA can be presented directly to the array (a few rounds of whole genome amplification may be desirable for some applications). In the case of gene expression analysis normal cDNA synthesis methods can be employed but the amount of starting material can be low. Genomic DNA is typically fragmented prior to use in the methods of the present invention. For example, the genomic DNA may be fragmented such that substantially all of the DNA molecules are 1 Mb, 100 kb, 50 kb, 10 kb and/or 1 kb or less in size. Fragmentation can be achieved using standard techniques such as passing the DNA through a narrow gauge syringe, sonication, alkali treatment, free radical treatment, enzymatic treatment (e.g. DNase1), or combinations thereof.

Target molecules may be presented as populations of molecules. More than one population can be applied to the array at the same time. In this case, the different populations are preferably differentially labelled (e.g. cDNA populations may be labelled with Cy5 or Cy3). In other cases such as analysis of pooled DNA, each population may or may not be differentially labelled.

A number of assay methods of the present invention are based on hybridisation of analyte to the single molecules of the array elements. The assay may stop at this point and the results of the hybridisation analysed.

However, the hybridisation events can also form the basis of further biochemical or chemical manipulations or hybridisation events to enable further probing or to enable detection (as in a sandwich assay). These further events include primer extension from the immobilised molecule/captured molecule complex; hybridisation of additional probes to the immobilised molecule/captured molecule complex and ligation of additional nucleic acid probes to the immobilised molecule/captured molecule complex.

For example, following specific capture (by hybridisation or hybridisation plus enzymatic or chemical attachment) of a single target strand by immobilised oligonucleotide(s), further analysis can be performed on the target molecule. This can be done on an end-immobilised target (or a copy thereof—see below). Alternatively, the immobilised oligonucleotide anchors the target strand which is then able to interact with a second (or higher number) of immobilised oligonucleotide(s), thereby causing the target strand to lay horizontally. Where the different immobilised oligonucleotides are different allelic probes for different loci, the target strand can be allelically defined at multiple loci.

The target strand can also be horizontalised and straightened, after being captured by an immobilised oligonucleotide by various physical methods known in the art. This can allow spatially addressable combing of target nucleic acids and makes them amenable to further analysis.

In one embodiment, following hybridisation the array oligonucleotide can be used as a primer to produce a permanent copy of the bound target molecule which is covalently fixed in place and is addressable.

In most single molecule assays the results are based on the analysis of a population of each of the target molecular species. For example, each array spot may capture a multitude of copies of a particular species. In some cases, however the result may be based on signals from one molecule only and not on the census of a multitude of molecules.

Single molecule counting of these assays allows even a rare polymorphism/mutation in a largely homogeneous population to be detected.

Some specific assay configurations and uses are described below.

Nucleic Acid Arrays and Accessing Genetic Information

To interrogate sequence, in most cases the target must be in single stranded form. The exception includes cases such as triplex formation, binding of proteins to duplex DNA (Taylor J R, Fang, M M and S. Nie, 2000, Anal. Chem. 72:1979-1986), or sequence recognition facilitated by RecA (see Seong et al., 2000, Anal. Chem. 72: 1288-1293) or by the use of PNA probes (Bukanov et al., 1998, PNAS 95: 5516-5520; Cherry et al., 1998, Biophysical Journal 1015-1023). Also, the detection of mismatches in annealed duplexes by MutS protein has been demonstrated (Sun, H B S and H Yokoto, 2000, Anal. Chem 72: 3138-3141). Long RNAs (e.g. mRNA) can form R-loops inside linear ds DNA and this can be the basis for mapping of genes on arrayed genomic DNA. Where a double stranded DNA target is arrayed, it may be necessary to provide suitable conditions to partially disrupt the native base-pairing in the duplex to enable hybridisation to probe to occur. This can be achieved by heating the surface/solution of the substrate, manipulating salt concentration/pH or applying an electric field to melt the duplex.

One preferred method for probing sequences is by probing double stranded DNA using strand invasion locked nucleic acid (LNA) or peptide nucleic acid (PNA) probes. This can be done under conditions where transient breathing nodes in the duplex structure can arise, such as at 50-65° C. in 0-100 mM monovalent cation.

Software tools for the prediction of LNA melting points are available in the art, for example at www.lna-tm.com. Tools for design of PNA probes (including PNA molecular beacons) are available at www.bostonprobes.com. Also see Kuhn et al., J Am Chem Soc. 2002 Feb. 13; 124(6):1097-103) for design of PNA probes.

Molecular Combing Methods

There are several methods that have been described to stretch out double stranded DNA so that it can be interrogated along its length. Methods include optical trapping, electrostatic trapping, molecular combing (Bensimon et al., Science 1994 265: 20962098), forces within an evaporating droplet/film (Yokota et al., Anal. Biochem 1998 264:158-164; Jing et al., PNAS 1998 95: 8046-8051), centrifugal force and moving the air-water interface by a jet of air (Li et al., Nucleic Acid Research (1998) 6: 4785-4786).

Molecular Combing which involves surface tension created by a moving air-water interface/mensicus and a modification to the basic technique has been used to stretch out several hundred haploid genomes on a glass surface (Michalet et al., Science. 1997 277: 1518-1523).

Relatively fewer methods have been described for single-stranded DNA. Woolley and Kelly (Nanoletters 2001 1: 345-348) achieve elongation of ssDNA by translating a droplet of DNA solution linearly across a mica surface coated with positive charge. The forces exerted on ssDNA are thought to be from a combination of fluid flow and surface tension at the travelling air-water interface. The forces within fluid flow can be sufficient to stretch out a single strand in a channel Capillary forces can be used to move solutions within channels.

These methods, in addition to stretching out DNA, overcome intermolecular secondary structures which are prevalent in ssDNA under conditions required for hybridisation. An alternative way of overcoming secondary structure formation of nucleic acids on a surface is by heating the surface of the substrate or applying an electric field to the surface.

The majority of the assays described below do not require the molecules to be linearised, as positional information along the molecules length is not required. In the cases where positional information is required, DNA needs to be linearised/horizontalised. The attachment to more than one surface immobilised probe facilitates the process. Double stranded targets can be immobilised to probes having sticky ends such as those created by restriction digestion.

In one embodiment, following capture by an immobilised oligonucleotide, a target strand is straightened. This can be done on a flat surface by molecular combing. In one embodiment the probes are placed on a narrow line on for example, the left most side of an array element and then the captured molecules are stretched out in rows form left side to the right side by a receding air-water interface.

Alternatively the captured target can be stretched out in a channel or capillary where the capture probes are attached to (one or more) walls of the vessel and the physical forces within the fluid cause the captured target to stretch out. Fluid flow facilitates mixing and makes hybridisation and other processes more efficient. Reactants can be recirculated within the channels during the reactions.

Single molecules can also be captured and stretched out in a gel. For example, a gel layer can be poured onto a glass slide. Capture probes or target molecules can be modified at the end with acrydite and co-polymerised with acrylamide monomers within a polyacrylamide gel. When an electric field is applied, as in gel electrophoresis, the molecule can be stretched out, whilst retaining attachment.

After hybridisation to capture probe it may be advantageous to immobilise the target independently to the surface. This can occur at suitable pH, for example pH 6.5 in 10 mM MES buffer onto bare glass or in 10 mM AMPSO buffer at pH 8.5 onto aminosilane slides. Alternatively, prior to interacting with the array, the target molecule may be pre-reacted with a moiety that will allow covalent attachment to the surface after suitable activation or after given a suitable length of time to react.

In fiber FISH (Fluorescent in situ Hybridization) probes are mapped onto denatured double stranded DNA which is stretched on a surface. Probes bound to DNA give the appearance of beads on a string. It has been suggested that the bead like appearance is due to the fact the conditions used in denaturing the DNA actually cause the DNA chain to snap.

Probing Linearised Molecules

Probing would be expected to be simplest on single stranded molecules. However, as mentioned it is also possible to probe by strand invasion by PNA or LNA oligonucleotides. One preferred method for probing sequences is by probing double stranded DNA using strand invasion locked nucleic acid (LNA) or peptide nucleic acid (PNA) probes under conditions where transient breathing nodes in the duplex structure can arise, such as at 50-65° C. in 0-100 mM monovalent cation. Alternatively, methods from Fiber FISH could be used in which the target strand is partially denatured in situ on the slide or before making Fibers. Depending on the method of detection the, probe may be labelled with dye molecules, polylabelled Dendriers or nanoparticles or microspheres. Probes would be preferentially labelled with large nanoparticles or microspheres to be able to be easily detected by epi-fluorescence microscopy, otherwise it may be difficult to see them above background.

Reprobing Linearised Molecules

In some embodiments of the invention, it may be necessary to remove one or more bound probes before binding of further probes. There are a number of ways that this can be done, including heat, alkali treating, electric field generation. For serial probing with a complete library it may be necessary to make the removal of bound probe as gentle as possible. One way would be to displace the target strand with a sequence that is complementary to the probe (For a possible mechanism see Yurke et al Nature 406: 605-608, 2000).

Alternatively, when using harsher conditions for removing probe it may be advantageous not to remove probe before each subsequent probe addition but only after several additions. For example all oligonucleotides of a particular Tm could be hybridised simultaneously and then removed. Then all oligonucleotides of another Tm would be added and removed and so on, noting positions of binding after each cycle. Where certain, first, oligonucleotides in one set does not hybridise to a single molecule due to overlap with a second oligonucleotide in the set that does hybridise, it is likely that by looking at the population of single molecules, there may be other single molecules in which the first oligonucleotide binds and the second one does not.

Another solution to the concern about the detrimental effects of the attrition caused by cycling of hybridisation and denaturation on the surface.

One problem is that often molecules that are stretched out on a surface undergo light induced breakage. Snapping of the strands of combed Lambda DNA labelled with YOYO can be seen with an epi-fluorescent microscope. Where this happens the length of the DNA contracts. Although this is not desirable, the long range position of oligonucleotides that bind can still be retained. Pulsed laser excitation would be able to overcome this DNA breakage because much lower laser power can be used. Also if the probes are labelled with multilabeled dendrimers or large nanoparticles or microspheres, the fact that the signal that is detected is from many dye molecules means that the illumination intensity can be minimized.

Another way to overcome having to do hundreds or thousands of annealing-denaturation cycles on one slide, is to make a multiple of slides in which the same genome sample is captured (for this it may be necessary to do whole genome amplification first). Then probing on a first slide would be with oligonucleotide sets 1, 2, 3 on a second slide with oligonucleotide sets 4, 5, 6, a third slide with oligonucleotide sets 7, 8, 9 and so on. Information from hybridisation to the same spatially addressable sites on each of these slides would be combined to provide the data that would be used to reconstruct the sequence. An array of array could be used in which each array is hybridised to different sets of probes. For example the arrays, and the captured strands may be on the surface of a flat bottomed microtitre plate and each well of the plate e.g. each one from a 96 well plate might take different probe sets.

Annealing and denaturation steps could be a cycled on a thermocycler or similar device adapted to enable addition and removal of probe molecules.

Various aspects are discussed below under individual headings but are typically broadly applicable to any detection technique where simultaneous interrogation of a single molecule at multiple sites is desired.

1. Resequencing and/or Typing of Single-Nucleotide Polymorphisms (SNPs) and Mutations a. Hybridisation The organisation of the array typically follow the known art as taught by Affymetrix e.g. Lipshutz et al., Nature Genetics 1999 21: s20-24; Hacia et al., Nature Genetics 21: s42-47)) for SNP resequencing or typing. In short, an SNP can be analysed with a block of array elements containing defined probes, in the simplest form, with probes to each known or possible allele. This can include substitutions and simple deletions or insertions. However, whereas the Affymetrix techniques require complex tiling paths to resolve errors, advanced versions of the single molecule approach can suffice with simpler arrays, as other means for distinguishing errors can be used. Transient interactions can also be recorded.

Typically the oligonucleotides are between about 17 and 25 nucleotides in length although longer or shorter probes can be used in some instances. The longer probes are particularly useful to overcome the effects of secondary structure. However the longer the length the less easy it is to discriminate a single base difference by hybridisation. The choice of conditions is important in achieving single base discrimination with longer probes. For example, Hughes et al (Nature Biotechnology 19: 342-347 2001) have shown that a one base difference in a 55mer can be discriminated. Analysis based on single molecule counting should help.

In a different implementation, a mix of probes complementary to all alleles is placed within a single array element. Each probe comprising a different allele is distinguishable from the other probes, e.g. each single molecule of a particular allele can have a specific dye associated with it. A single molecule assay system of the invention allows this space saving operation and is simple to do when pre-synthesised oligos are spotted on the array.

The probe can be appended with a sequences that promote its formation into a secondary structure that facilitate the discrimination of mismatch (e.g. a stem loop structure where the probe sequence is in the loop).

Similarly the probe sequence can be a molecular beacon making the assay free from the need for extrinsic labels.

The following are typical reaction conditions that can be used: 1M NaCl or 3-4.4 M TMACl (tetramethyl ammonium chloride) in Tris Buffer, target sample, 4 to 37° C. in a humid chamber for 30 mins to overnight.

It is recognised that hybridisation of rare species is discriminated against under conventional reaction conditions, whilst species that are rich in A-T base pairs are not able to hybridise as effectively as G-T rich sequences. Certain buffers are capable of equalising hybridisation of rare and A-T rich molecules, to achieve more representative outcomes in hybridisation reactions. The following components may be included in hybridisation buffers to improve hybridisation with positive effects on specificity and/or reduce the effects of base composition and/or reduce secondary structure and/or reduce non-specific interactions and/or facilitate enzyme reactions:

1M Tripropylamine acetate; N,N-dimethylheptylamine; 1-Methyl piperidine; LiTCA; DTB; C-TAB; Betaine; Guanidinium isothyacyanate; Formamide; Tetramethy ammonium chloride (TMACl); Tetra ethyl Ammonium Chloride (TEAC1); Sarkosyl; SDS (Sodium dodecyl sulphate); Dendhardt's reagent; Poly ethylene Glycol; Urea; Trehalose; Cot DNA; tRNA; Poly d(A) N—N-dimethylisopropylamine acetate.

Buffers containing N—N-dimethylisopropylamine acetate are very good for specificity and base composition. Related compounds with similar structure and arrangement of charge and/or hydrophobic groups can also be used. Refer to WO9813527.

Probes are chosen, where possible, to have minimal potential for secondary structure (unless it is part of the design) and cross hybridisation with non-targeted sequences.

Where the target molecules are genomic DNA and specific PCRs are not used to enrich the SNP regions of choice, measures need to be taken to reduce complexity. The complexity is reduced by fragmenting the target and pre-hybridising it to $C_0t$=1 DNA. Other methods are described by Cantor and Smith (Genomics, The Science and Technology Behind the Human Genome Project 1999; John Wiley and Sons]. It may also be useful to perform whole genome amplification prior to analysis.

The probes are preferentially morpholino, locked nucleic acids (LNA) or peptide nucleic acids (PNA).

Molecules and their products can be immobilized and manipulated on a charged surface such as an electrode. Applying an appropriate bias to the electrode can speed up hybridization and aid in overcoming secondary structure when the bulk solution is at high stringency. Switching polarity aids in preferentially eliminating mismatches b. Stacking Hybridisation Adding either sequence specific probes or a complete set of probes in solution that coaxially stack onto the immobilised probe, templated by the target, can increase the stability and specificity of the hybridisation. There is a stability factor associated with stacking and this is abrogated if there is a mismatch present between the immobilised probe and the solution probe. Therefore mismatch events can be distinguished by use of appropriate temperatures and sequence.

The probe can be appended with sequences that configure it to form a secondary structure such that it provides a coaxial stacking interface onto which the end of a target is juxtaposed. This may be a favourable approach when the target is fragmented.

It is advantageous to use LNA probes as these may provide better stacking features due to their pre-configured "locked" structure.

The following are typical reaction conditions that can be used: 1M NaCl in Tris Buffer; 1 to 10 nM (or higher concentration) stacking oligonucleotide; target sample; 4-37° C. 30 min to overnight.

c. Primer Extension

This is a means for improving specificity at the free end of the immobilised probe and for trapping transient interactions. There are two ways that this can be applied. The first is the multiprimer approach, where as described for hybridisation arrays, there are separate array elements containing single molecules for each allele:

The second is the multi-base approach in which a single array contains a single species of primer whose last base is upstream of the polymorphic site. The different alleles are distinguished by incorporation of different bases each of which is differentially labelled. This approach is also known as mini-sequencing.

The following reaction mix and conditions can be used: 5× polymerase buffer, 200 mM Tris-HCL pH 7.5, 100 mM $MgCl_2$, 250 mM NaCl, 2.5 mM DTT; ddNTPs or dNTPs (multibase); dNTPs (multiprimer), Sequenase V.2 (0.5 Mil) in polymerase dilution buffer, target sample, 37° C. degrees 1 hr.

It can be advantageous to label the primer/capture probe to lend more confidence to an extension signal, if it co-localises with labelled capture probe.

Advantageously, a concentration of $10^{-7}$M dNTP, eg dCTP, is used. Preferably no cold dNTP corresponding to the labelled dNTP is added. Advantageously, an exo-polymerase, preferably thermosequenase (Amersham) or Taquenase (promega), is used.

The target can be capture immobilised and synthesis primed using an upstream primer. Multiple primers can prime synthesis at several points along the captured target. The target may or may not be horizontalised.

d. Ligation Assay

Ligation (chemical or enzymatic) is another means for improving specificity and for trapping transient interactions. Here the target strand is captured by the immobilised oligonucleotide and then a second oligonucleotide is ligated to the first, in a target dependent manner. There are two ways that this can be applied. In the first type of assay, the "second" oligonucleotides that are provided in solution are complementary in the region of the known polymorphisms under investigation. One oligo of either the array oligos or the "second" solution oligonucleotide overlaps the SNP site and the other ends one base upstream of it.

In the second type of assay, the second oligonucleotides in solution comprise the complete set, every oligonucleotide sequence of a given length. This allows analysis of every position in the target. It may be preferable to use all sequences of a given length where one or more nucleotides are LNA.

A typical ligation reaction is as follows: 5× ligation buffer, 100 mM Tris-HCL pH 8.3, 0.5% Triton X-100, 50 mM MgCl, 250 mM KCl, 5 mM NAD+, 50 mM DTT, 5 mM EDTA, solution oligonucleotide 5-10 pmol. *Thermus thermophilus* DNA ligase (Tth DNA ligase) 1 U/ul, target sample, between 37° C. and 65° C. 1 hr.

Alternatively, stacking hybridisation can be performed first in high salt: 1M NaCl, 3-4.4M TMAC1, 5-10 pmol solution oligonucleotide, target sample.

After washing of excess reagents from the array under conditions that retain the solution oligonucleotide, the above reaction mix minus solution oligonucleotide and target sample is added to the reaction mix.

Combining the Power of Different Assay Methods

The power of primer extension and ligation can be combined in a technique called gap ligation (the processivity and discriminatory power of two enzymes are combined). Here a first and a second oligonucleotide are designed that hybridise in close proximity to the target but with a gap of preferably a single base. The last base of one of the oligonucleotides ends one base upstream or downstream of the polymorphic site. In cases where it ends downstream, the first level of discrimination is through hybridisation. Another level of discrimination occurs through primer extension which extends the first oligonucleotide by one base. The extended first oligonucleotide now abuts the second oligonucleotide. The final level of discrimination occurs where the extended first oligonucleotide is ligated to the second oligonucleotide.

Alternatively the ligation and primer extension reactions described in c. and d. above can be performed simultaneously, with some molecules of the array giving results due to ligation and others giving results due to primer extension, within the same array element. This can increase confidence in the base call, being made independently by two assay/enzyme systems. The products of ligation may be differently labelled than the products of primer extension.

The primer or ligation oligonucleotides may be designed on purpose to have mismatch base at a site other than the base that serves to interrogate the polymorphic site. This serves to reduce error as duplex with two mismatch bases is considerably less stable than, a duplex with only one mismatch.

It may be desirable to use probes that are fully or partially composed of LNA (which have improved binding characteristics and are compatible with enzymes) in the above described enzymatic assays.

The invention provides a method for SNP typing which enables the potential of genomic SNP analysis to be realised in an acceptable time-frame and at affordable cost. The ability to type SNPs through single-molecule recognition intrinsically reduces errors due to inaccuracy and PCR-induced bias which are inherent in mass-analysis techniques. Moreover, if errors occur which left a percentage of SNPs untyped, assuming errors are random with regard to position of SNP in the genome, the fact that the remaining SNPs are typed without the need to perform individual (or multiplexed) PCR still confers an advantage. It allows large-scale association studies to be performed in a time- and cost-effective way. Thus, all available SNPs may be tested in parallel and data from those in which there is confidence selected for further analysis.

There is a concern that duplicated regions of the genome may lead to errors, where the results of an assay may be biased by DNA from a duplicated region. The direct assay of the genome by single molecule detection is no more susceptible to this problem than assays utilising PCR since in most instances PCR amplifies a small segment surrounding the SNP site (this is necessary to achieve multiplex PCR). However, with the availability of the sequence of the genome, this is less of a problem as in some cases it may be possible to select non-duplicated regions of the genome for analysis. In other cases, the sources of bias is known and so can be accounted for.

If signal is obtained from probes or labels representing only one allele then the sample is likely to be homozygous. If it is from both, in substantially a 1:1 ratio then the sample is likely to be heterozygous. As the assays are based on single molecule counting, highly accurate allele frequencies can be determined when DNA pooling strategies are used. In these cases, the ratio of molecules might be 1:100. Similarly, a rare mutant allele in a background of the wild-type allele might be found to have ratio of molecules as 1:1000.

Tagging Mismatches

As an alternative means for selecting SNPs or mutations is to detect the sites of mismatches when a heterozygous sample DNA (one or both of which contain 2'-amine substitute nucleotides) is denatured and re-annealed to give heteroduplexes can be tagged by 2' amine acylation. Preferably, an unknown sample DNA can be hybridised to modified tester DNAs of known sequence. This is made possible by the fact that acylation occurs preferably at flexible positions in DNA and less preferably in double stranded constrained regions (John D and K Weeks, Chem. Biol. 2000, 7: 405-410). This method can be used to place bulky tags onto sites of mismatch on DNA that has been horizontalised. Detection of these sites may then be, for example, by AFM. When this is applied genome-wide the genome can be sorted by array probes or the identity of fragments obtained by use of encoded probes.

Homogeneous Assays

Low background fluorescence and the elimination of the need for post-assay processing to remove unreacted fluorescent labels can be achieved by two approaches. The first is the use of Molecular Beacons (Tyagi et al Nat. Biotechnol. 1998, 16:49-53) and other molecular structures comprising dye-dye interactions in which fluorescence is only emitted in the target bound state and is quenched when the structure is unbound by the target. In practice a fraction of the molecular beacons fluoresce and so an image may need to be taken before adding targets to the array to make a record of false positives.

The second is the analysis of fluorescence polarization of a dye labelled molecule (Chen et al Genome Res. 1998, 9: 492-98). For example, in a mini-sequencing assay, free and incorporated dye labels exhibit different rotary behaviour. When the dye is linked to a small molecule such as a ddNTP, it is able to rotate rapidly, but when the dye is linked to a larger molecule, as it is if added to the primer by incorporation of the ddNTP, rotation is constrained. A stationary molecule transmits back into a fixed plane, but rotation depolarises the emitted light to various degrees. An optimal set of four dye terminators are available where different emissions can be discriminated. These approaches can be configured within single molecule detection regimes. Other homogeneous assays are described by Mir and Southern (Ann Rev. Genomics and Human Genetics 2000, 1: 329-60). The principles inherent in pyrosequencing (Ronaghi M et al Science, 1998, 363-365) may also be applicable to single molecule assays.

2. Haplotyping

Capture of singly resolvable DNA molecules is the basis for haplotype determination in the target by various means. This can be done either by analysing signals from the single foci containing the single DNA molecule or by linearising the DNA and analysing the spatial arrangement of signal along the length of the DNA.

Two or more polymorphic sites on the same DNA strand can be analysed. This may involve hybridisation of oligonucleotides to the different sites but each labelled with different fluorophores. As described, the enzymatic approaches can equally be applied to these additional sites on the captured single molecule.

Figure 7A:
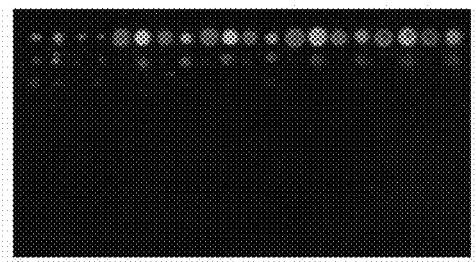
FIG. 7A illustrates an exemplary Image of Microarray scan under normal settings. The array carries a dilution series over 12 orders of magnitude concentration from (top to bottom) and a range of oligonucleotide attachment methods from (left to right) for alternative cy3 and cy5 labelled oligonucleotides.
Figure 7C:
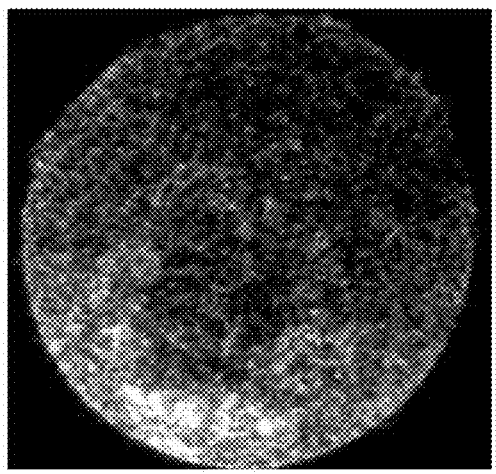
FIG. 7C illustrates an exemplary microarray spot from the same array but analysed by Total Internal Reflection Microscopy (TIRF) so that single molecules can be detected (red arrows point to fluorescence from a single molecule).

In one embodiment, each probe in a biallelic probe set may be differentially labelled and these labels are distinct from the labels associated with probes for the second site. The assay readout may be by simultaneous readout, by splitting of the emission by wavelength obtained from the same foci or from a focal region defined by the 2-D radius of projection of a DNA target molecule immobilised at one end. This radius is defined by the distance between the site of immobilized probe and the second probe. If the probes from the first biallelic set are removed or their fluors photobleached then a second acquisition can be made with the second biallelic set which in this case do not need labels that are distinct from labels for the first biallelic set. In another embodiment haplotyping can be performed on single molecules captured on allele-specific microarrays. Haplotype information can be obtained for nearest neighbour SNPs by for example, determining the first SNP by spatially addressable allele specific probes (see FIG. 7A). The labelling is due to the allelic probes (which are provided in solution) for the second SNP. Depending on which foci colour is detected within a SNP 1 allele specific spot determines the allele for the second SNP. So spatial position of microarray spot determines the allele for the first SNP and then colour of foci within the microarray spot determines the allele for the second SNP. If the captured molecule is long enough and the array probes are far enough apart then further SNP allele specific probe, each labelled with a different colour can be resolved by co-localization of signal to the same foci.

Figure 7B:
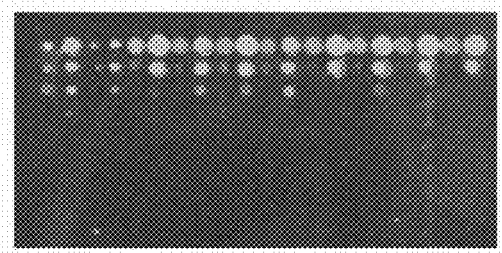
FIG. 7B illustrates the same array but with decreased gamma setting.
Figure 7D:
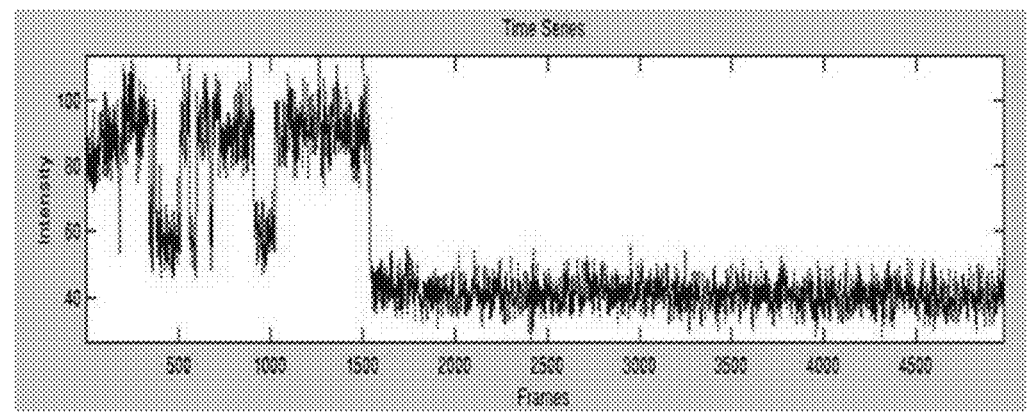
FIG. 7D shows an exemplary plot of intensity versus time for a single molecule signal, showing blinking and one step photobleaching.
Figure 8:
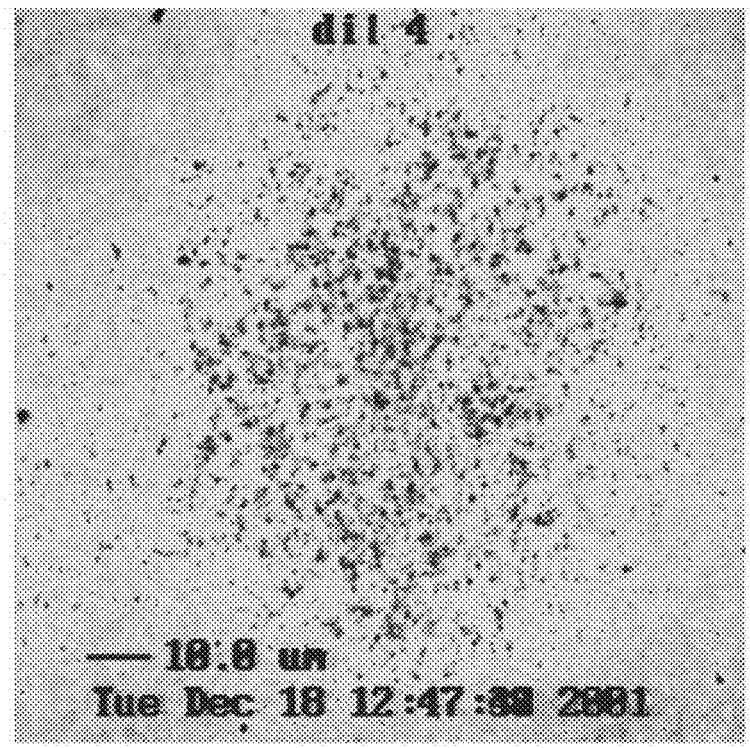
FIG. 8 shows the counting of single molecules by TIRF

More extensive haplotypes, for three or more SNPs can be reconstructing from analysis of overlapping nearest neighbour SNP haplotypes (see FIG. 7B) or by further probing with differently labeled probes on the same molecule.

Samples molecules may be pre-processed to bring distal sites into closer vicinity. For example this can be done by appropriate modular design of PCR or ligation probes. For example, the modular ligation probe has a 5' sequence that ligates to one site and the 3' portion has a sequence that ligates at a distal site on the target. Use of such modular probes juxtaposes two distal elements of interest and cuts out the intervening region that is not of interest.

In the case where the target has been horizontalised, the labels associated with the first locus need not be distinct from labels associated with subsequent loci; the position specifies the identity.

The probes for all alleles to be analysed will be added once the target molecule has been straightened. Alternatively, the probes can be reacted with the sample DNA before array capture.

Currently efforts are underway to establish the haplotype structure of the genome. With this information available it would be possible to use much fewer SNP probes to represent the haplotype diversity. For example rather than using 30 probes to assess a haplotype on array captured/combed DNA, only 4 probes may suffice.

An alternative approach would be to use a haplotype tag (Johnson et al Nat Genet 2001 October; 29(2):233) to capture a particular haplotype. This tag would form one of the spatially addressable probe elements on the array.

A limitation of DNA pooling methods for genotyping is that because individual genotypes are not analysed, the estimation of haplotypes is complicated. However, in the methods described in the present invention, DNA pooling strategies can be used to obtain Haplotype frequencies.

3. Fingerprinting

A captured target strand can be further characterised and uniquely identified by further probing by hybridisation or other means. The particular oligonucleotides that associate with the target strand provide information about the sequence of the target. This can be done by multiple acquisitions with similarly labelled probes (e.g. after photobleaching or removal of the first set) or simultaneously with differentially labelled probes. A set of oligonucleotides, which are differentially labelled can be specifically used for simultaneous fingerprinting.

Again, individual molecules may be simultaneously multiply probed as described for haplotyping.

4. Nucleic Acid Sequencing

Capture of singly resolvable DNA molecules is the basis for complete or partial sequence determination of the target by various means. This can be done either by analysing signals from single foci containing the single DNA molecule or by linearising the DNA and analysing the spatial arrangement of signal along the length of the DNA.

Sequencing by Synthesis

The array can be designed in such a way that each spot captures a consecutive fragment of DNA from the genome. For example probes can be 100 bases apart in the genome (or the part of the genome of interest). The intervening sequence can then be determined by sequencing by synthesis (for example, see WO9844152 and references cited therein). The probes can also be part of a n-mer set (see below). The underlying theory of procedures according to the invention is that, contrary to natural primer mediated template directed complementary DNA synthesis, only one base can be added at one time (further additions being prevented by, for example, a blocking group similar to having protecting groups in automated chemical DNA synthesis) and the base added to each single molecule is detected and recorded after base addition. The blocking group is then removed allowing the next base to be added. As well as base by base, the procedure can also be performed dinucleotide by dinucleotide or oligomer by oligomer (of any convenient length).

Sequencing of Linearised DNA

The signal that is detected may be an intrinsic property of the DNA. For example, a system based on a scanning near field optical probe can be used to measure the native absorbance of the bases. Alternatively a label can be artificially introduced. Analogue bases that are naturally fluorescent such as 2-aminopurine can be incorporated into the strands and the fluorescence can be measured. Other fluorescent groups can be incorporated directly or one of the bases can be tagged with groups such as biotin, which can itself be detected by a fluorescent label (phycoerethryn). Such incorporation being dependent on the chemical group, it can be done in vivo by uptake of bases by incorporation into replicating DNA by cells. Alternatively it can be done by incorporation during in vitro synthesis. Sequencing is based on recording the distance between bases of each type and the relative order of bases of different types. Covalently attached markers or bound markers would aid in determining the relative order of bases. Several means for doing this have been described (see WO 01/13088; WO 98/35012; WO 00/09757; US 20010014850; U.S. Pat. No. 6,210,896; US Genomics). Again in addition to measuring label on individual bases, dinucleotides or oligomers (of any convenient length) can be labelled with a tag that would uniquely identify the dinucleotide or oligomer and its position of occurrence relative to other bases can thus be recorded. The draft sequence of the human genome, or other genomic map, may be utilised in reconstruction of the sequence.

The captured DNA can be sequenced by determining interactions by Watson-Crick base pairing, serially to a complete set of sequences, e.g. every 6-mer.

The DNA can be immobilised, e.g. by acrydite modification (Kenney M, Ray S, Boles T C. Mutation typing using electrophoresis and gel-immobilized Acrydite probes. Biotechniques. 1998 September; 25(3):516-21) at one end in a gel while the DNA is straightened out by the application of a voltage across the gel. The gel environment and the single point of attachment would make the DNA robust to iterative probing and melting.

Similarly, DNA attached at one end in a channel but dangling in a flowstream can be put through iterative probe-denature cycles in which in each cycle a different probe is applied; the stretching out in the flowstream would enable the positions of each probe to be determined.

For example, a mixture of two or more probes can be placed within the array element. The plating densities are such that individual probe molecules are sufficiently spaced to capture a single molecule at defined points. Alternatively, two or more probes can be placed at defined array elements to stretch out DNA between array elements by hybridisation to these probes. The horizontal molecule can then be characterised by, for example, using fluorescent probes or tagged probes (as described below). Each array element addresses an individual fragment from the genome. This can form the basis of resequencing the genome using SPM or a high resolution optical method. If the array has one million sites, then it is typically necessary to fragment human genomic DNA into 3000 by lengths to cover the entire genome. For a 50,000 element array 60 kb fragments cover the entire human genome. The method for sequencing and sequence reconstruction is given in the section below.

The target DNA may be substantially a double stranded molecule and probing may be by strand invasion with PNA or LNA. Hybridisation at around 50° C. is sufficient to create single stranded nodes within the duplex which seeds strand invasion. A salt concentration between 0 and 1 M Na is typically appropriate for PNA. A salt concentration between 50 mM and 1 M Na is typically appropriate for LNA.

The target may be substantially single stranded but is made accessible to hybridisation by stretching out on a surface. This may be achieved by passing the molecules through a channel that makes a seal with the substrate and passing a solution of the molecules through by capillary action.

The disadvantage of probing double stranded DNA is that there is ambiguity about which of the two strands the probe has hybridised to. A way to overcome this is to probe simultaneously with a pair of complementary probes. There is no such problem with ssDNA or when a ssDNA is made double stranded with incorporation of tagged probes.

Determination of all positions on a single molecule, by contiguous ligations of tagged probes provides the sequence.

It is possible to synthesize four DNA strands each having one of the four bases fluorescently labelled, each of a different colour, in separate tubes. All four are mixed together and captured by array probes, which preferably are localised along a line. This line of array probes can be created by nanolithography, e.g. by dip pen lithography of gold on a mica surface. Thiolated oligonucleotides can self assemble on to the gold surface to form Self-Assembled Monolayers (SAMs). The relative distances of each of the four bases can be determined by their relative positions. When each strand contains two of the four bases then the reconstruction of sequence will be simpler (there are 6 different combinations).

There are a number of ways that sequence information can be cross validated between the method described herein. The following are two examples:

It is possible to synthesize strands carrying internally labelled bases, immobilise the strands by spatial capture on an array and then perform further sequence determination by serial probing with a complete library of oligonucleotides e.g. timers. The sequence will be determined by cross-validation between the two methods (incorporation and probing).

Once molecules are stretched out, optical mapping can be performed to identify individual molecules and to provide landmarks onto which the sequence can be constructed by the hybridisation of oligonucleotides. This can be done by performing restriction digestions in situ. This can be done before or after labelling the molecule. This will facilitate the sequence reconstruction.

The advantage of the proposed method is that the spatially addressable capture enables different sections of the genome to be sequenced separately and it will be known where on the long range map the each sequence run assembles. The methods proposed by US Genomics do not provide this and there are possibilities for incorrect positioning of sequences on a long range map. If the genome draft is solely used for this long range reconstruction then information of large scale duplications, amplifications, deletions, translocations etc may be lost. Also it would take longer to complete the sequencing and lengthy sample preparation procedures would be required in advance of the sequencing run. In the method of this invention the sample preparation before array hybridisation takes from only a few hours to as little as one hour. Moreover, the method of the present invention provides haplotype information over a region, if all the sequencing is performed on a single molecule over that region. The haplotype can be mined from the data even if the sequence reconstruction is due to compiling data from a multitude of the single molecules that are immobilised to the same spatial address on the array.

A sequencing workflow including sequencing by hybridisation can have the following steps:
(i) Perform sequencing by hybridisation on single molecules;
(ii) Attempt Reconstruction;
(iii) Find areas of low confidence or low coverage;
(iv) Compare to draft genome sequence or other available sequence information if available;
(v) Based on (iii) and (iv) probe again with a subset of oligonucleotide which may be longer or of a different chemistry;
(vi) Attempt reconstruction;
(vii) Iterate until desired confidence in sequence is achieved or display regions of low confidence or gaps.

Where far-field methods are used for detection, the task of the algorithm is to assemble sequence despite only knowing position of an oligonucleotide to within about 750 base pairs (250 microns). This can be improved by image processing and deconvolution (Michalet X, Lacoste T D, Weiss S. Ultra-high-resolution colocalization of spectrally separable point-like fluorescent probes. Methods. 2001 September; 25(487-102). In this case the reconstruction algorithm will be similar to a sequencing by hybridisation algorithm of the type developed by Pevzner using graph theory (Belyi I, Pevzner P A. Software for DNA sequencing by hybridization. Comput Appl Biosci. 1997 April; 13(2):205-10). The sequence within a 250 micron focal point can be re-constructed by this method. The list of possible reconstructed sequences obtained by the Pevzner type methods for one focal point is overlapped with list of possible sequences form an overlapping focal point and so on to reconstruct the long range sequence of the spatially addressably combed sample DNA molecules.

Where near-field methods are used or the resolution from far field methods is enhanced by processing, then the long range reconstruction can be done from the outset. In this case an algorithm of the type developed by Adelman, for Position sensitive sequencing would be useful.

Methods for computing the sequence may be based on methods developed for Sequencing by Hybridisation (Belyi I, Pevzner P A. Software for DNA sequencing by hybridization. Comput Appl Biosci. 1997 April; 13(2):205-10; Southern et al., 1992 Genomics 13:1008-17). See WO9713868.

In order to eliminate errors in sequencing, it is necessary to take account of information from the population of single molecules and then compute solutions, assigning likelihood values to each solution.

As an alternative to performing the sequencing on planar surfaces, each single molecule can be wrapped around an encoded bead and a population of beads carrying the whole genome is placed in the wells of a microtitre plate. Each well of a microtitre plate has different probe sets applied to it in annealing denaturation steps. In this scenario the genome is preferably fragmented into small pieced e.g 100s of base pairs and the reconstruction of the sequence does not have at its disposal information about the position where probes bind. The beads can be viewed in the wells by confocal or two-photon microscopy or removed and applied to a flow cytometer.

5. STR Analysis

The array oligonucleotide can probe the sequence flanking a repetitive element. This captures a sequence containing a repetitive element. It is then used to seed ligation of probes complementary to the repetitive sequence, along the target strand or to act as primer to polymerise a complementary strand to the repetitive elements. Then the number of repeat units are determined by quantitating the level of signal from fluorescently labelled oligonucleotides or fluorescent nucleotides. Only completely extended oligos which incorporate an oligo (preferably by stacking hybridisation or ligation) complementary to the other flanking sequence labelled with a different fluorophore, are typically counted. It may be helpful to obtain ratios between fluorescence intensity from the extended region and the labelled flanking sequence Ligation conditions described above (see 1c) can be used; a reaction temperature of 46-65° C. with a thermostable ligase is preferable. Polymerisation conditions described above can be employed.

A method to determine repeat lengths based on providing probes complementary in length to the different target repeat lengths as described (Case Green et al, p 61-67 DNA Microarrays A Practical Approach Ed: M. Schenal 999 Oxford University Press) can also be implemented at the singe molecule level.

6. Expression Analysis

Conventional microarray expression analysis is performed using either synthetic oligonucleotide probes (e.g 40-75 nt) or longer cDNA or PCR product probes (typically 0.6 kb or more) immobilised to a solid substrate. These types of arrays can be made according to the present invention at low surface coverage (as described in section A). After hybridisation, the level of gene expression can be determined by single molecule counting using the methods of the invention. This gives increased sensitivity and allows events due to noise to be distinguished from real events. Also, as the basic unit of counting is the single molecule, even a rare transcript can be detected. One implementation of expression analysis involves comparison of two mRNA populations by simultaneous analysis on the same chip by two-colour labelling. This can also be done at the single molecule level by counting each colour separately by for example beam splitting. Capture of a target cDNA or mRNA can allow further analysis by oligonucleotide probing. For example this can be used to distinguish alternatively spliced transcripts.

Microarray theory suggests that accurate gene expression ratios at equilibrium can be obtained when the sample material is in limiting amounts.

A permanently addressable copy of an mRNA population can be made by primer extension of molecules separated on single molecule arrays. Primers can be designed based on the available genome sequence or gene fragment sequences. Alternatively, unknown sequences can be sampled using a binary probe comprising a fixed element that can anchor all mRNA and a variable element that can address/sort the repertoire of mRNA species in a population. The fixed element may be complementary to sequence motifs that are common to all mRNA such as the Poly A sequence or the Polyadenylation signal AAUAAA or preferably to a common clamp sequence that is ligated to all mRNA or cDNA at 5' or 3' ends. The copy can be used as the basis for further analysis such as sequencing.

7. Comparative Genomic Hybridisation (CGH).

Gridded genomic DNA or genomic DNA immobilized by spatially addressable capture probes (or complementary copies) is probed by genomic DNA from a different source to detect regions of differential deletions and amplifications between the two samples. The immobilized sample containing multiple copies of each species may be a reference set and genomic DNA from two different sources may be differentially labeled and compared by hybridization to the reference.

8. Detection of Target Binding to a Repertoire of Oligonucleotides

A target can be hybridised to a repertoire of ligands. Single molecule analysis is advantageous; for example it reveals binding characteristics of conformational isomers and overcome the steric hindrance associated with binding of targets to arrays in which molecules are tightly packed. Hybridisation is conducted under conditions close to those that occur in the intended use of any selected ligand.

For antisense oligonucleotide binding to RNA, hybridisation occurs at 0.05 to 1 M NaCl or KCl with MgCl2 concentrations between 0 and 10 mM in for example Tris Buffer. One picomole or less of target is sufficient. (Refer to EP-A-742837: Methods for discovering ligands).

9. Protein—Nucleic Acid Interactions

Interactions between biological molecules, such as proteins, and nucleic acids can be analysed in a number of ways. Double stranded DNA polynucleotides (by foldback of designed sequences) can be immobilised to a surface in which individual molecules are resolvable to form a molecular array. Immobilised DNA is then contacted with candidate proteins/polypeptides and any binding determined by the methods described above. Alternatively RNA or duplex DNA can be horizontalised and optionally straightened by any of the methods referred to herein. The sites of protein binding may then be identified within a particular RNA or DNA using the methods described herein. Candidate biological molecules typically include transcription factors, regulatory proteins and other molecules or ions such as calcium or iron. When binding to RNA is analysed meaningful secondary structure is typically retained.

The binding of labeled transcription factors or other regulatory proteins to genomic DNA immobilized and linearised by the methods referred to herein may be used to identify active coding regions or the sites of genes in the genome. This is an experimental alternative to the bioinformatic approaches that are typically used to find coding regions in the genome. Similarly, methylated regions of the genome can be identified and marked by using antibodies specific for 5-methylcytosine. Differential methylation may be an important means for epigenetic control of the genome, the study of which is becoming increasingly important. Information from tag sequence probes is can be combined with information about methylated regions and coding regions.

An alternative means for determining the methylation status of DNA are by force or chemical force analysis using AFM. For example a silicon nitride AFM tip interacts differently with methyl cytosine in DNA, which is more hydrophobic than non-methylated DNA.

12. Optical Mapping

Optical mapping, in which the restriction digestions are done directly on DNA linearised on a surface can be done in an ordered genome-wide manner by spatially addressably capturing genomic fragments by arrayed probes. The restriction digestions can then be performed. The restriction digestions would be a way of getting Restriction Fragment length Polymorphism (RFLP) information.

Other applications include RNA structure analysis and assays that involve hybridisation of DNA sequence tags to anti-tag arrays.

Where immobilisation is within a channel or sheath, instead of horizontalisation, the molecule may be made parallel to the channel length.

n-Mer Arrays and Assays n-mer arrays (every possible sequence of a given length) can be used for sequencing by hybridisation. n-mer arrays can also be used to sort a complex sample. This is particularly advantageous where they are linked to an anchor sequence, for example polyadenylation signal sequence or Poly A tail, or a sequence complementary to a clamp/adaptor sequence that has been ligated to target molecules. Each element of the spatially addressable array will contain a common anchor sequence and a unique member of the n-mer set. These probes can be used in hybridisation, primer extension, ligation assays etc. In particular they can be used for priming sequencing by synthesis reactions, where for example the sequence has been fragmented and fragments-have been ligated to a clamp. The advantage of the n-mer is that a certain amount of sequence information is already obtained from the target just by hybridisation of the n-mer before a sequencing by synthesis reaction has been performed. A stem loop probe in which one strand of stem forms a sticky end onto which the target clamp hybridises and optionally ligates may be a favourable configuration.

Other Types of Assays

The present invention is not limited to methods of analysing nucleic acids and interactions between nucleic acids. For example, in one aspect of the invention, the molecules are proteins. Antibodies may be used to bind protein. Other probes can further interrogate protein. For example, further epitopes may be accessed by antibodies or an active site by a small molecule drug.

Low density molecular arrays may also be used in methods of high-throughput screening for compounds that interact with a given molecule of interest. In this case, the plurality of molecules represent candidate compounds (of known identity). The molecule of interest is contacted with the array and the array interrogated to determine where the molecule binds. Since the array is spatially addressable, the identity of each immobilised molecule identified as binding the molecule of interest can be readily determined. The molecule of interest may, for example, be a polypeptide and the plurality of immobilised molecules may be a combinatorial library of small molecule organic compounds.

Many of the above assays involve detecting interactions between molecules in the array and target molecules in samples applied to the array. However, other assays include determining the properties/characteristics of the arrayed plurality of molecules (even though their identity is already known), for example determining the laser induced fluorescence characteristics of individual molecules. An advantage over bulk analysis is that transient processes and functional isomers are detected.

Thus in summary, the assays of the invention and the low density molecular arrays of the invention may be used in a variety of applications including genetic analysis, such as SNP detection, haplotyping, STR analysis, sequencing and gene expression studies; identifying compounds/sequences present in a sample (including environmental sampling, pathogen detection, genetically modified foodstuffs and toxicology); and high throughput screening for compounds with properties of interest. High throughput genetic analysis is useful in medical diagnosis as well as for research purposes.

Advantages of the single molecule array approach can be summarised as follows:
1. Can resolve complex samples.
2. Can separate correct signals from erroneous signals
3. Sensitivity of detection down to a single molecule in the analyte.
4. Sensitivity of detection of a single variant molecule within a pool of common (e.g. wild-type) molecules.
5. Eliminates need for sample amplification.
6. Allows individual molecules in target sample to be sorted to discrete array elements and to ask specific questions of said target molecules e.g. analyse multiple polymorphic sites (i.e. haplotyping).
7. Can perform time-resolved microscopy of single molecular events within array elements and hence detect transient interactions or temporal characteristics of single molecule processes.
8. Due to single molecule counting can get very precise measurements of particular events e.g. Allele frequencies or mRNA concentration ratios.

The various features and embodiments, referred to in individual sections above apply, as appropriate, to other sections, mutatis mutandis. Consequently features specified in one section may be combined with features specified in other sections, as appropriate.

The invention is further described, for the purpose of illustration, in the following examples.

EXAMPLES

Example 1

Cleaning Substrates

The following procedures are preferably performed in a clean room. The surface of a pure white glass plate/slide (Knittel Glazer, Germany) (which may be polished for flatness) or spectrosil slides is thoroughly cleaned by, for example, sonication in a surfactant solution (2% Micro-90) for 25 minutes, washing in de-ionised water, rinsing thoroughly with milliQ water and immersing in 6:4:1 milliQ $H_2O$:30% $NH_4OH$:30% $H_2O_2$ or in a $H_2SO_4/CrO_3$ cleaning solution for 1.5 hr. After cleaning the plate is rinsed and stored in a dust free environment e.g. under milliQ water. The top layer of Mica Substrates is cleaved by covering with scotch tape and rapidly pulling off of the layer.

Example 2

Microscopy

1) TIRF
There are two configurations that can be used with TIRF, the objective method and the Prism method.

The objective method is supported by Olympus Microscopes and application notes are found at the following web site: olympusmicro.com/primer/techniques/fluorescence/tir-Volympusaptirfhtml The Prism method below is described in Osborne et al J. Phys. Chem. B, 105 (15), 3120-3126, 2001.

The instrument consists of an inverted optical microscope (Nikon TE200, Japan), two color laser excitation sources, and an Intensified Charge Coupled Device (ICCD) camera (Pentamax, Princeton Instruments, NJ). A mode-locked frequency-doubled Nd:YAG laser (76 MHz Antares 76-s, Coherent) is split into two beams to provide up to 100 mW of 532-nm laser light and a pump dye laser (700 series, Coherent) with output powers in excess of 200 mW at 630 nm (DCM, Lambda Physik). The sample chamber is inverted over a ×100 oil immersion objective lens and a 60 fused silica dispersion prism optically coupled to the back of the slide through a thin film of glycerol. Laser light is focused with a 20-cm focal length lens at the prism such that at the glass/sample interface it subtends an angle of approximately 68° to the normal of the slide and undergoes total internal reflection (TIR). The critical angle for a glass/water interface is 66°. The footprint of the TIR has a 1/e2 diameter of about 300 m. Fluorescence produced by excitation of the sample with the surface-specific evanescent wave is collected by the objective, passed through a dichroic beam splitter (560DRLP, Omega Optics), and filtered before imaging onto the ICCD camera. Images were recorded by using synchronized 532 nm excitation with detection at 580 nm (580DF30, Omega) for TAMRA labeled substrates and 630 nm excitation with detection at 670 nm (670DF40, Omega) for Cy5 labeled probes. Exposure times are set between 250 and 500 ms with the ICCD gain at maximum (1 kV). The laser powers at the prism are adjusted to 40 mW at both laser wavelengths.

2) Confocal Microscopy with Pulsed Laser and Time Resolved Detection

This set up is available as the Lightstation from Atto_tec (Heidelberg)

3) AFM

Images can be obtained by using a Multimode IIia with a nanoscope IV controller and Si cantilever tips (Veeco, Santa Barbara, Calif.). This is placed on an active isolation system (MOD1-M, Halcyonics, Gottingen, Germany). Typical imaging parameters are 60-90 Hz resonant frequency, 0.5-1V oscillation amplitude, 0.3-0.7V setpoint voltage, 1.5-2 Hz scan rate.

4) SNOM

The BioLyser SNOM (Triple-0 Potsdam, Germany) can be used for near field optical imaging.

The following CCD set ups can be used I-PentaMAX Gen III; Roper Scientific, Trenton, N.J. USA) or cooled (e.g. Model ST-71 (Santa Barbara Instruments Group, CA, USA); ISIT camera composed of a SIT camera (Hamamatsu), an image intensifier and (VS-1845, Video Scope International, USA) and stored on S-VHS videotape. Video taped images are processed with a digital image processor (Argus-30, Hamamatsu photonics). Gain setting are adjusted depending on camera and brightness of signal.

The movement form one field of view to another can be done by attaching the substrate on a High Precision TST series X-Y translation stage (Newport)

The following oxygen scavenging solution can be used to minimise photobleaching when single molecule analysis is done in solution: Catalase (0.2 mg/ml), Glucose oxidase (0.1 mg/ml), DTT (20 mM), BSA (0.5 mg/ml), Glucose 3 mg/ml. This can be added to the buffer solution that is being used in the experiment.

Example 3

General Scheme for Determining Optimal Spotting Concentration for Making Single Molecule Arrays Where the array is made by spotting, spots of oligonucleotides of different sequence or identity are placed at different spatial locations on a surface.

The first step in the procedure for making a single molecule microarray is to do a dilution series of fluorescent oligonucleotides. This has been done with 13 mers and 25 mers but any appropriate length of oligonucleotide can be chosen. These oligonucleotides may be aminated and preferably Cy3 labeled at the 5' end.

Although this is exemplified for oligonucleotides, this procedure is also appropriate to proteins and chemical spotting.

A 10 uM solution of the oligonucleotide is placed in a first well of the microtitre plate. For a 10 fold dilution, 1 ul is transferred into the next well of the microtitre plate and so on over several orders of magnitude. Twelve orders of magnitude were tested. A 1:1 volume of 2× spotting buffer that is being tested is added to each well. This gives 5 uM concentration in the first well, 500 nM in the second well and so on. The array is then spotted using a microarrayer (Amersham Generation III).

The Dilution series is then analysed by TIRF microscopy, AFM or by another relevant microscopy system. The morphology of spot is looked at and the distribution of molecules within the spot determined. The spot range with the desired number of resolvable single molecules is chosen. Optionally, a further more focused dilution series is created around the dilution of interest. For example, two 50% dilutions in the range 500 nM to 50 nM can be done.

In a first experiment, a dilution series over 12 orders of magnitude was spotted with 4 buffers to establish the range of dilutions necessary. Subsequently, more focused dilutions series are used. It was found that between 250 nM to 67.5 nM gave resolvable single molecules within an identifiable spot. (If there are too few molecules then it is difficult to know exactly where the spot is but this will not be a problem when spot position and morphology is known to be regular and movement of translation stage or CCD is automated and is not manual). Some spots give a faint ring around the perimeter which can help identify spots.

To achieve a single molecule array, a dilution series of modified and unmodified oligonucleotides was tested a) in several different spotting buffers; b) on three different slide chemistries; c) on slides from several different manufacturers; d) using two different humidities and e) using several different post-spotting protocols. Due to the effects of photobleaching, the amount of pre-exposure to light also influences the number of single-dye labeled single molecules that can be counted.

Slides

It was found that the intrinsic fluorescence from slides from different suppliers varied. We found the slides most appropriate for our low fluorescence needs (determined by TIRF microscopy) to be the commercial slides from Asper Biotech (Tartu, Estonia) coated and cleaned on slides supplied by Knittel Glaser (Germany). These slides not only have a uniform surface coating of silanes but also have very low intrinsic fluorescence. Regular glass slides are float glass and contain some levels of intrinsic fluorescence but specialty pure white glass is more suitable. —Spectrosil fused silica slides (TSL group, Tyne and Wear, UK) are also appropriate but are more expensive. Cover glass which is made of borosilicate glass is also of low fluorescence but some spotters cannot spot onto these.

Slide Chemistry

Three different slide chemistries, Epoxysilane, Aminosilane and enhanced aminosilane (3-Aminopropyltrimethoxysilane+1, 4-Phenylenediisothiocyanate) have been tested. Single molecule arrays can be obtained with all three chemistries.

Oligonucleotide Chemistry

Unmodified DNA oligonucleotides and oligonucleotides that were aminated at the 5' or 3' end were tested. There appears to be no significant difference in morphology or attachment whether the oligos are terminally modified or not. However, only the terminally modified oligos have been tested in hybridization or other assays. Several different sequences of varying lengths that probe TNF alpha promoter have been tested.

Buffers

In total 11 different buffers have been tested. From the study it has emerged that the best general buffer on the epoxysilane slides supplied by Asper Biotech is 50% DMSO and 50% Water. This buffer gives far superior spot morphology than any other buffer that was tested. Spotting humidity affects the morphology. Spotting was tested at 42-43% and 53-55% humidity with both conditions giving useable arrays. However, there is a slight doughnut effect at 43% humidity compared to the almost perfect homogeneity at 55% humidity. QMT2 (Quantifoil, Jena Germany) buffer also give reasonable spots on Asper's Epoxysilane slides.

After spotting the epoxysilane slide is, optionally, placed at 97 degrees C. for 15 minutes before storage at room temperature for 12-24 hours. This is followed by storage at 4 degrees C. overnight or, preferably, longer. The slides are washed before use. Two methods of washing work well. The first is washing 3× in milliQ water at room temperature. The second is washing on the Amersham Slide Processor (ASP). The following wash protocol was used:

| ASP WASH PROTOCOL | |
|---|---|
| HEAT | To 25 degrees |
| MIX | Wash 1, (1XSSC/0.2% SDS) 5 or 10 minutes |
| PRIME | Prime with wash 2(0.1XSSC/0.2% SDS) |
| FLUSH | Wash 2 |
| MIX | Wash 2 30 seconds or 1 minute |
| FLUSH | Wash 3 (Wash (0.1XSSC) |
| MIX | Wash 3 30 seconds or 1 minute |
| PRIME | Prime with was 4 (0.1XSSC) |
| FLUSH | Wash 4 (0.1XSSC) |
| Prime | Prime with Isopropanol |
| Flush | Flush with Isopropanol |
| Flush | Flush with air |
| Airpump | Dry Slide |
| Heat | Turn off Heat |

The best buffers on the enhanced aminosilane (3-Aminopropyltrimethoxysilane+1,4-Phenylenecliisothiocyanate) slides from Asper Biotech are 50% 1.5M Betaine/50% 3×SSC and 10% QMT1 spotting buffer (Quantifoil, Jena). In addition, some of the other buffers from Quantifoil (Jena, Germany) performed reasonably well; different concentrations of these buffers may give better morphology. Detailed internal morphology seen with epi was not good. DMSO buffer (Amersham) gave intense "sunspots", i.e. a dot of intense fluorescence, within the spots; it is conceivable that single molecules can be counted in the rest of the spot, ignoring the sunspot. Spotting was tested at 43% and 55% humidity with both conditions giving useable arrays.

For the enhanced aminosilane slides, post-processing involves optional 2 hours at 37 degrees in a humid chamber. Under these conditions, more molecules stick but there is a possibility that spots can come out of line or merge. To avoid this, the spots are arrayed far enough apart to prevent merger. This is followed by overnight (or longer) at 4 degrees C. The slides are then dipped in 1% Ammonia solution for 2-3 minutes. The slides are then washed 3× in water and then put at 4 degrees C. overnight. There is some degree of bleeding of dye from the spots after hybridization. This may be addressed by more stringent or longer washing.

If the buffers in the microtitre wells dry out, they can be resuspended again in water. However, the betaine buffer did not perform well when this was done.

50% DMSO is the best buffer for aminosilane slides. After spotting these slides are immediately crosslinked with 300 mJoules on a Stratagene Crosslinker. The arrays are washed in hot water with shaking twice for two minutes and are then dipped five times in 95% ethanol and immediately dried with forced air. Substantially more aminated oligonucleotides stick to the surface with this slide chemistry than with other slide chemistries, even when the slides are not fresh. Therefore less oligonucleotide needs to be spotted to get a particular surface density.

Spotting Pins

Capillary pins from Amersham Biotech optimized for Sodium Thiocyanate buffer or pins optimized for DMSO buffer were used in different spotting runs. Both types of pins enabled single molecule arrays to be constructed. Other preferred spotting methods are the Affymetrix ring and pin system and ink jet printing. Quills can also be used.

Example 4

An Array Made by In Situ Parallel Synthesis

The glass substrate can be cleaned (and all reagents used in the following steps should be of high purity) and then modified to allow oligonucleotide synthesis. For epoxy derivatisation the following steps are taken:

Prepare a mixture of 3-Glycidoxypropyl trimethoxysilane (98%) (Aldrich), di-isopropylethylamine, and xylene (17.8: 1:69, by volume) in a glass cylinder. Place the glass substrate in the mixture so that it is completely immersed and incubate at 80 degrees C. for 9 hours. Remove the glass substrates from the mixture and allow them to cool to room temperature and wash with ethanol and ether by squirting liquid from a wash bottle. For adding a spacer: Incubate the glass substrates in hexaethylene glycol (neat) containing a catalytic amount of sulphuric acid (approx. 25 ul per liter) at 80 degrees C. for 10 hours with stirring. Remove the glass substrates, allow them to cool to room temperature and wash with ethanol and ether. Air Dry the plates and store at −20 degrees C.

The array of oligonucleotides complementary to for example, yeast tRNAPhe is created by coupling nucleotide residues in the order in which they occur in the complement of the target sequence using a reaction cell pressed against the surface of a pure white glass plate/slide (Knittel Glazer, Germany) which is modified (see above).

The fluidics from an ABI 394 DNS synthesizer is coupled into the reaction cell through inlet and outlet ports (instead of coupling to cpg columns). The DNA synthesizer is programmed with the following cycle (for a diamond-shaped reaction chamber with 30 mm diagonal and 0.73 mm depth):

TABLE 1

Program for ABI394 DNA/RNA synthesizer to deliver reagents for one coupling cycle.

| Step number | Function Number | Function Name | Step time (s) |
|---|---|---|---|
| 1 | 106 | begin | |
| 2 | 103 | wait | 999 |
| 3 | 64 | 18 to waste | 5 |
| 4 | 42 | 18 to column | 25 |
| 5 | 2 | reverse flush | 8 |
| 6 | 1 | block flush | 5 |
| 7 | 101 | phos prep | 3 |
| 8 | 111 | block vent | 2 |
| 9 | 58 | tet to waste | 1.7 |
| 10 | 34 | tet to column | 1 |
| 11 | 33 | B + tet to column | 3 |
| 12 | 34 | tet to colum | 1 |
| 13 | 33 | B + tet to column | 3 |
| 14 | 34 | tet to column | 1 |
| 15 | 33 | B + tet to column | 3 |
| 16 | 34 | tet to column | 1 |
| 17 | 103 | wait | 75 (or optionally 140s) |
| 18 | 64 | 18 to waste | 5 |
| 19 | 2 | reverse flush | 10 |
| 20 | 1 | block flush | 5 |
| 21 | 42 | 18 to column | 15 |
| 22 | 2 | reverse flush | 10 |
| 23 | 63 | 15 to waste | 5 |
| 24 | 41 | 15 to column | 15 |
| 25 | 64 | 18 to waste | 5 |
| 26 | 1 | block flush | 5 |
| 27 | 103 | wait | 20 |
| 28 | 2 | reverse flush | 10 |
| 29 | 1 | block flush | 5 |
| 30 | 64 | 18 to waste | 5 |
| 31 | 42 | 18 to column | 15 |
| 32 | 2 | reverse flush | 9 |
| 33 | 42 | 18 to column | 15 |
| 34 | 2 | reverse flush | 9 |
| 35 | 42 | 18 to column | 15 |
| 36 | 2 | reverse flush | 9 |
| 37 | 42 | 18 to column | 15 |
| 38 | 2 | reverse flush | 9 |
| 39 | 1 | block flush | 3 |
| 40 | 62 | 14 to waste | 5 |
| 41 | 40 | 14 to column | 30 |
| 42 | 103 | wait | 20 |
| 43 | 1 | block flush | 5 |
| 44 | 64 | 18 to waste | 5 |
| 45 | 42 | 18 to column | 25 |
| 46 | 2 | reverse flush | 9 |
| 47 | 1 | block flush | 3 |
| 48 | 107 | end | |

An interrupt is set at step 1 of the next base to allow the operator (or automated x-y stage) to move the substrate one increment and restart the program. A long wait step at the beginning of the program is optional and is introduced if the operator does not wish to use the interrupt step. The operator is also advised to consult the user's manual for the DNA synthesizer. The operator is also advised to ensure there are enough reagents in the reagent bottles to last the run and to check the run of fluids through the base lines (e.g. the G line may need to be continuously flushed with acetonitrile for several minutes to ensure clear flow through).

The movement can be done by attaching the substrate on a High Precision TST series X-Y translation stage (Newport) and the sealing of the reaction cell is controlled in the X axis with a stepometric stage (Newport) attached with a load cell. These devices can be controlled by software created in Labview (National Instruments) on a IBM compatible personal computer.

After each base coupling, the synthesis is interrupted the plate is moved along by a fixed increment. The array can be made using "reverse synthons", i.e. 5' phosphoramidites, protected at the 3' hydroxyl, leaving 5'-ends of the ON tethered to the glass. The first base is then added at the right-most position. The diameter of the reaction cell is 30 mm and the offset at each step to the left is 2.5 mm. The result is that after 12 steps, an oligonucleotide complementary to bases 1-12 of the tRNA$^{phe}$ has been synthesised in a patch 25 mm wide, 11×2.5=27.5 mm from the right of the plate, where the 12 footprints of the reaction cell all overlapped. At this point, the footprint of the reaction cell passes on and adds the 13$^{th}$ base, so that the next patch contains the 12-mer corresponding to bases 2-13. The process continues until, in this example all 76 bases of the tRNA$^{phe}$ are represented along the centre of the plate. Depending on the shape of the reaction cell (see Southern et al), in addition, the following oligomers are also present on the array: all 11-mers are in the cells flanking the 12-mers, the next row of cells contains 10-mers and so on to the edge rows which contained the 76 mononucleotides complementary to the sequence of the tRNA$^{phe}$. For finactionalisation the protecting groups on the exocyclic amines of the bases must be removed by Ammonia treatment. In addition this process strips oligonucleotides from the surface of the array and a long enough incubation reduces the density of probes to the level that single molecules can be individually resolved. To reduce the high density array to single molecule arrays, place the glass substrate, array side up, into a chamber that can be very tightly sealed. Add 30% high Ammonia into the chamber to cover the slides. Tightly seal the chamber and place in a water bath at 65 degrees C. for 24 hours or at 55 degrees C. for 4 days. The temperature and incubation period can be adjusted depending on the density of molecules that is required (which would be defined by method for detection e.g far field or near-field). Cool before opening chamber. The array can be rinsed with nailliQ water and is ready for use in hybridisation or ligation experiments (after enzymatic phosphorylation) if standard amidites are used. If as in this example, reverse synthons are used then the array can be used for hybridisation, ligation or primer extension.

As an alternative to the destructive ammonia method, the first base coupling in the array can be mixed with monomer amidite containing a blocking group such as the base-labile protecting group 9-fluorenylmethoxycarbonyl (Fmoc) in 1:1000 ratio (it is preferable to first optimise this step by coupling patches on the same surface with different ratios of mixtures to determine optimal molecule separation for each kind of single molecule detection experiment). As this base is not labile to acid which is used to remove the dimethoxytrityl protecting group in the standard chemistry, it will not get removed and therefore will not allow any further chain extension. If the Fmoc amidite is in excess it will limit the number of chains that can be synthesized. If desired the Fmoc group can be deprotected at the end of chain synthesis and functionalised with, for example, a group carrying a negative charge. This will help repel any non specific binding of nucleic acids and their monomers.

Alternatively, an in situ DNA synthesizer, such as the one produced by Genium (Febit, Mannheim, Germany) may be used. DNA synthesis on this machine can be specified to make single molecule arrays. Alternatively, once the arrays are made the channels can be flushed with destructive ammonia treatment.

Example 5

Making Double Stranded Arrays

Any of the primary arrays of this invention that are single stranded can be made double stranded, for example to assay the binding site of transcription factors.

This can be done by making a pool of all sequences of target length and hybridising to the array to make double stranded molecules, using e.g. 3.5M TMACL at room temperature for 17mers.

Alternatively, a common sequence may be included on the array oligonucleotide onto which a primer binds and initiates synthesis of a complementary strand.

Example 6

Hybridisation to Single Molecule Arrays

A simple array containing the biallelic probe set for two sequences of TNF alpha promoter were tested. The array probes were designed with the polymorphic base at the centre of a 13mer sequence. One of two oligonucleotides with Cy3 label at the 5' end (or TAMRA label), complementary to one of the two biallelic probes was hybridised to the single molecule array. The array contained a dilution series of the biallelic probe set. It was found that there was more signal from the perfect match than the mismatch. Spots down the dilution series were analysed, and single molecule counting was done in the spots found to give even and resolvable distribution of single molecule signals. Resolution of molecules at higher dilutions is possible by optimising the set up and by software for deconvolution. BSA, carrier DNA, tRNA, NTPs could be added in the hybridisation mix or a pre-hybridisation done to block non-specific binding.

Hybridisation Cycle for Hybridisation of Oligonucleotides to 13 Mer Oligos on Array.

The Automated Slide Processor from Amersham Pharmacia was used for hybridisation:

| ASP HYBRIDISATION PROTOCOL | |
|---|---|
| PRIME | PRIME WITH WASH 1 |
| WAIT | inject probe |
| HEAT | To 25 degrees |
| MIX | Hybridisation mixing for 12 hrs or 2 hours |
| FLUSH | Wash 1 (1x SSC/0.2% SDS) |
| HEAT | To 30 degrees C. |
| MIX | Wash 1 5 minutes |
| PRIME | Prime with wash 2(0.1XSSC/0.2% SDS) |
| FLUSH | Wash 2 |
| MIX | Wash 2 30 seconds |
| FLUSH | Wash 3 (Wash (0.1XSSC) |
| MIX | Wash 3 30 seconds |
| PRIME | Prime with was 4 (0.1XSSC) |
| FLUSH | Wash 4 (0.1XSSC) |
| Prime | Prime with Isopropanol |
| Flush | Flush with Isopropanol |
| Flush | Flush with air |
| Airpump | Dry Slide |
| Heat | Turn off Heat |

Alternatively, a manual hybridization set up as known in the art can be used. Briefly, a droplet of hybridization mix is sandwiched between the array substrate and a coverslip. The hybridization performed in a humid chamber (with optional edges sealed with rubber cement). The coverslip is slid off in wash buffer and washes are done preferably with some shaking.

On enhanced aminosliane slides, QMT buffer 1, 1.5M Betaine 3×SSC gave the best results. A faint ring was seen around the spots in 1.5M Betaine 3×SSC. Concentrations between 250 nM and 67.5 nM were appropriate for single molecule counting on relatively fresh slides. These slides should be stored at −70 degrees C. At room temperature the ability to retain probe after spotting wanes badly over a 2 month period.

Example 7

Array Capture and Combing of Long DNA

Lambda Model System

Linear Lambda DNA has complementary 12 base overhangs at each end which can anneal to circularise the DNA. The following oligonucleotides complementary to each end overhang are used in the following examples:

Lambda A: 5' GGG CGG CGA CCT 3'
Lambda B: 5' AGG TCG CCG CCC 3'.

A microarray of probes capture a target and the target can become stretched out on a surface. Capture probes for lambda DNA sequence Lambda A and Lambda B, complementary to each of sticky ends of linear lambda were spotted in microarrays. Spots containing completely unmatched sequences was included in the microarray. One set of A and B oligonucleotides were modified with amine and two further A and B oligonucleotides were modified with biotin. Amersham UV Crosslinking reagent (containing DMSO) was spotted with an equal volume of oligonucleotide dissolved in milliQ $H_2O$ was used to spot these probes onto an aminosilane modified slide (Asper, Estonia). After spotting, the slides were crosslinked at 3000 mJoules followed by two washes in hot water followed immediately by drying by blowing with forced air from a pressurised Airduster canister. The oligos were spotted at 5 uM and 500 nM concentrations (using spot diameter setting 255 microns, spots per dip: 72, 55% humidity on the Amersham Pharmacia Generation III spotter). Lambda DNA (20 ul; 40 ug/ml was incubated with 3 ul YOYO (neat) (Molecular Probes, Oregon). The Solution was then brought up to 1 milliliter in 4×SSC 0.2% Sarkosyl. 250 ul of this was added to the Amersham Slide Processor (ASP) machine for a 12 hour hybridization protocol (see ASP protocol B). The cycle included a series of stringency washes, isopropanol flow and air drying. The slide was analysed by epi-fluorescence microscope by pipetting 30 ul Fluoromount G under a coverslip and viewing on an upright epi-fluorescence microscope (Olympus BX51) fitted with a Sensys CCD camera and MetaMorph imaging software (Universal Imaging Corporation). 10× Objective was used for wide field viewing and 60× and 100×1.3 NA oil immersion lenses were used to view microarray spots, with fibres clearly visible.

FIGS. 10A-10D show results. Better images of DNA fibres were obtained after removing coverslip in PBS/Tween, staining with YOYO, washing with PBS/Tween and adding Fluoromount G. FIGS. 10A-10D show spatially addressable combed Lambda DNA spots. Lambda DNA becomes immobilised and combed to spots containing sequence A and not to non-matched sequences.

Molecules other than Lambda can be combed in this way by for example, generating sticky ends with the infrequent base cutter Not1 (produces average 65 KB which is close Lambda DNA).

Single Stranded DNA can be captured with LNA probes and combed as described here. An alternative to combing by the ASP is manual flushing with wash reagents and isopropanol or methanol, with the slide in a vertical position. This can be done in a fibre-FISH Sequenza coverplate apparatus (Shandon, USA).

Combing and Probing DNA

Dephosphorylate Lambda DNA (500 ug/ul) with calf alkaline phosphatase (this step minimizes concatemerization and circularization of Lambda DNA). Ligate Biotinylated Lambda A sequence to one end of lambda. Hybridise lambda to array using ASP Protocol B. Optionally treat slide with BSA. Add 40 nM, Red, Neutravidin coated Fluospheres (Molecular Probes, Oregon) in 4×SSC/Sarkosyl and BSA (%). Wash in PBS/Tween followed by PBS wash. Visualize DNA captured and combed on microarray spot containing sequence Lambda B, with fluorescent Fluosphere particle attached to Lambda.

Beads can be reacted with 1 mg/ml BSA solution to avoid absorption of the beads onto the glass surface.

Example 8

Probing of Horizontalisation of DNA

Figure 9A:
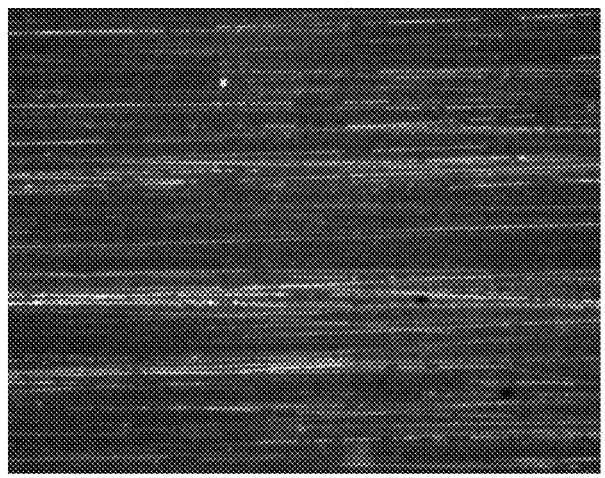
FIG. 9A shows concatemerised lambda phage stretched out on a microscope slide (FOV approx. 250 microns).
Figure 9B:
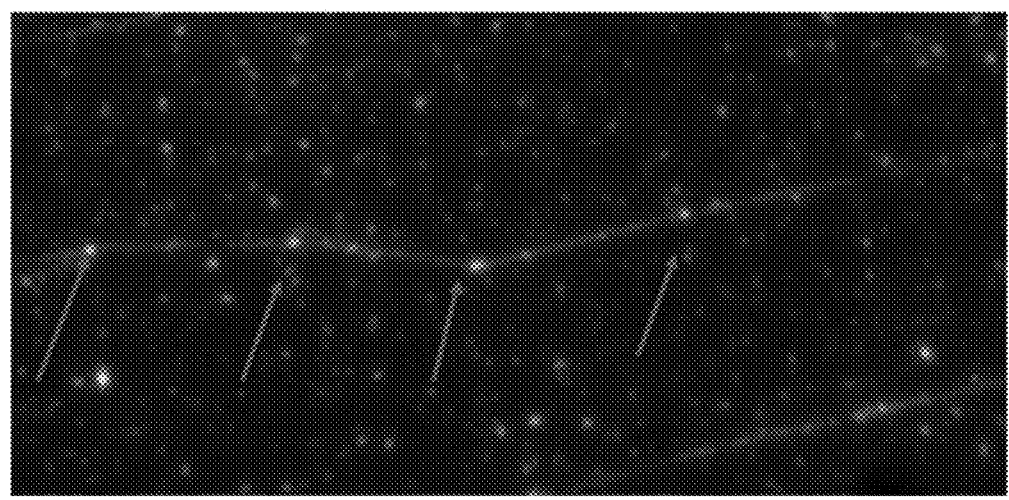
FIG. 9B shows sequence repetitively probed on lambda concatemer (arrow).

Fluorescent nanoparticle labeled oligonucleotides have been used to probe Lambda DNA stretch out on a surface (FIGS. 9A and 9B).

Make probes by reacting biotinylated oligonucleotides with strepatvaidin coated nanoparticles: Add 400 picomoles (4 ul) of each of oligonucleotide sequences Lambda A and Lambda B to 0.5 ul 20 nM Streptavidin modified Yellow/Green Fluosphere Nanoparticle (Molecular Probes). Incubate at 37 degrees for 30 minutes in the dark. Keep at 4 degrees C. Concatemerize Lambda DNA by mixing 2 ul Lambda DNA (500 ug/ml) with 1 ul Thermal T4 RNA ligase (Epicentre), 8 ul Ligase Buffer (supplied with enzyme). Incubate at 65 degrees C. for 30 minutes. Then add 8 ul of oligonucleotide-Fluosphere mix to the Ligation reaction. Incubate for a further 30 minutes at 65 degrees C. Incubate with YOYO for at least 20 minutes. Comb the DNA onto an untreated glass slide or dilute and incubate on a aminosilane coated slide. Dry slide and mount with Fluoromount G.

Combing can be done by a number of different methods including the following:

Method A: Place coverslip on top of microscope slide. Pipette 30 ul of sample solution on side of coverslip for uptake by capillary action. Leave 24 hours by which time solution should be dry and coverslip can be shaken off. If the coverslip does not come off easily, the slide can be soaked in PBS/0.01% Tween20 in which coverslip will float off. The slide will is washed in PBS and air dried.

Method B: Add a 30 ul drop at one end of the slide at the center. Use a forced air canister (Air Duster, Sapona) at an approximately 45 degree angle from the slide surface to gently blow the droplet from one side of the center of the slide to the other. It is then blown off the slide. This method immobilizes approximately 10× less combed DNA than Method A. 10 fold more combed Lambda DNA is retained on aminosilane coated slides compared to an uncoated slide.

Figure 10A:
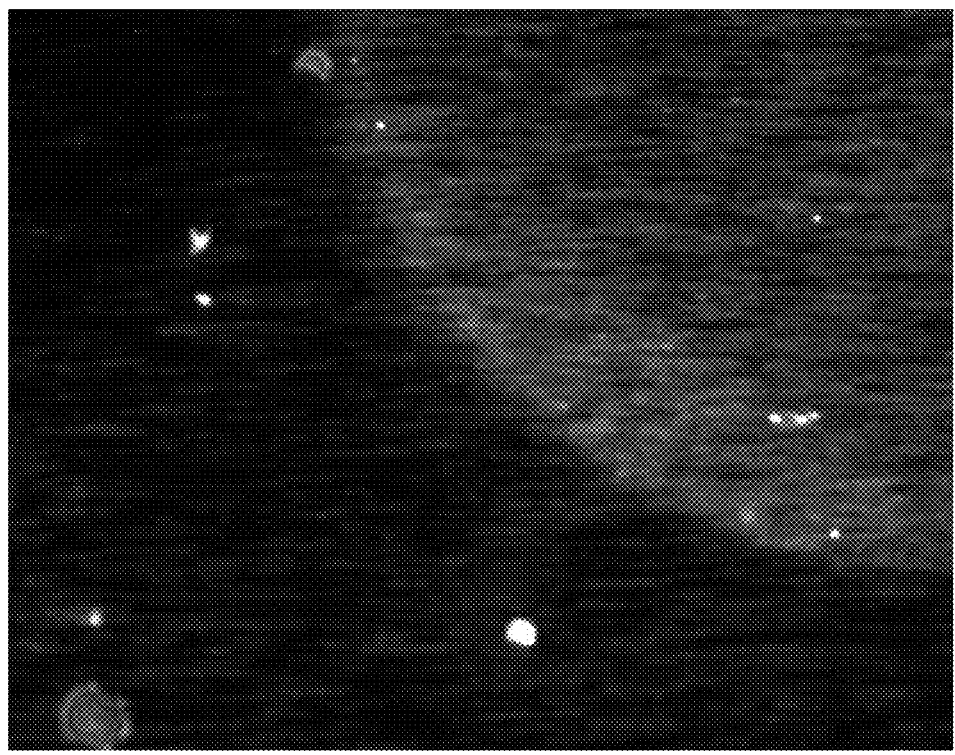
FIGS. 10A-10D show spatially addressable combed Lambda DNA spots.
Figure 10B:
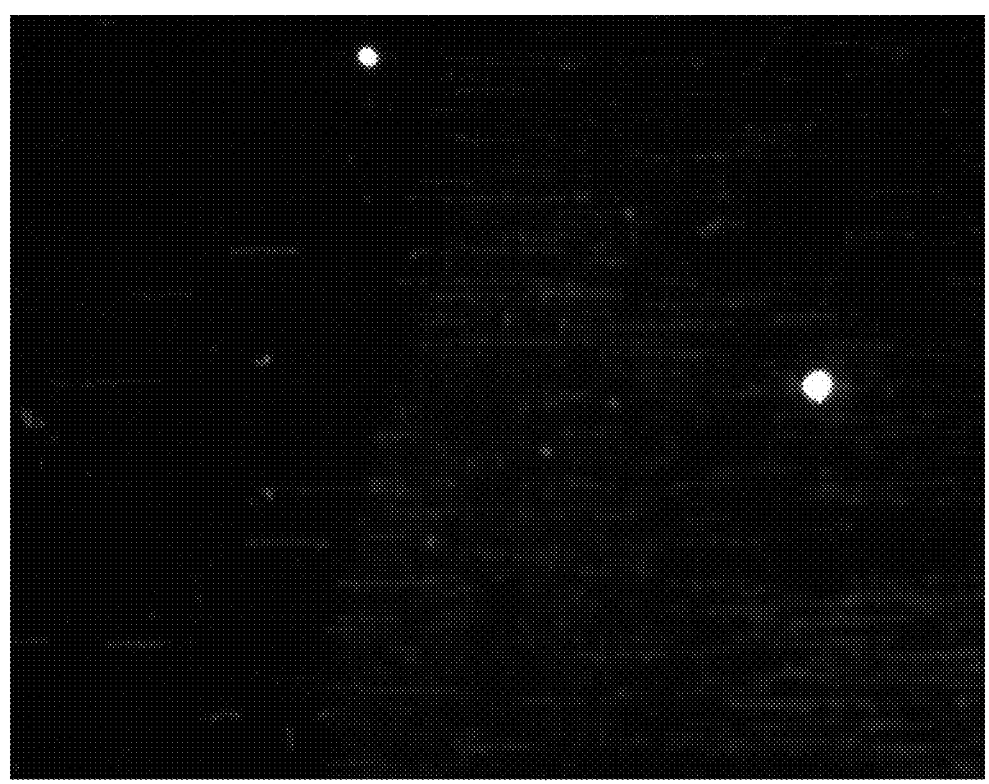
Figure 10C:
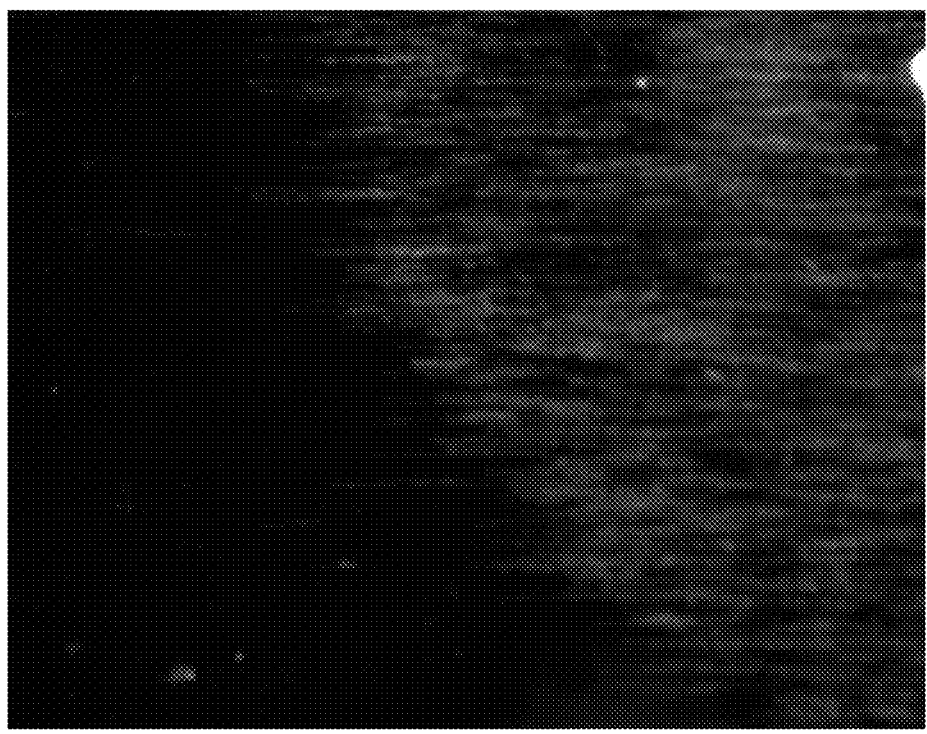
Figure 10D:
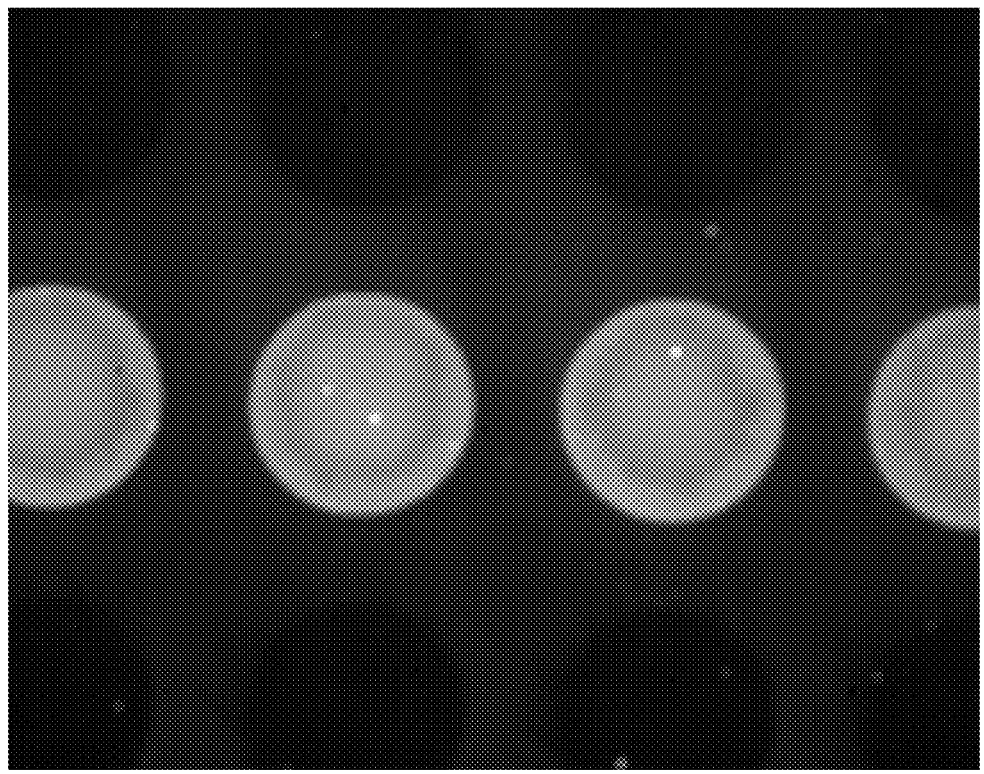

Upon visualization on an epi-fluorescence microscopy a recurring sequence on the lambda concatamers is labelled by Fluosphere complex (see FIG. 10B).

Lambda Molecules probed in this way can also be spatially addressably captured and combed essentially as described above.

Example 9

Making Single Stranded DNA/RNA, Hybridising to Primary Array to Make Secondary Array, Probing Secondary Array One method for probing when secondary array is made with single stranded DNA is as follows:

Single strand are made e.g. by Asymmetric (long Range) PCR, magnetic bead methods, selective protection of one strand form exonuclease degradation or by in vitro RNA transcription.

Hybridise single stranded DNA to array

Single stranded DNA may be hybridised at two points within or between microarray elements to enable stretching out (the linker holding one or both of the two array probes should be capable of rotating)

Alternatively single stranded DNA can be hybridised to the array, in 3-6×SSC buffer at room temperature for 25 mers which may be facilitated by enzymatic reactions such as ligation or by a coaxially stacking oligo or staking of several contiguous oligos. Sites that are known to remain accessible to probing under low stringency conditions are chosen for probing (these can be selected on oligonucleotide arrays; see Milner et al, Nat Biotechnol. 1997 June; 15(6):537-41.).

After hybridisation of single strand the strand needs to be covalently attached at site of capture and then washed stringently to remove secondary structure The captured single stranded target can then be stretched out as described by Woolley and Kelly (Nanoletters 2001 1: 345-348) by moving a droplet of fluid across a positively charged surface.

Need to control density of positive charge on the surface by coating with 1 ppm poly-L-lysine. The appropriate concentrations of other surface coatings e.g. Aminosilane need to be determined empirically Need to maintain the ssDNA at low ionic strength. Use 10 mM Tris, 1, M EDTA pH8 (TE buffer)

Move to move droplet of fluid across the surface at a velocity of Approx. 0.5 mm/s (within range 0.2-1 mm/s) This can be done by fixing the slide/mica onto a TST series translation stage (Newport), placing a droplet of fluid onto this, and translating the fluid with respect to the surface by dipping a stationary glass pipette onto the droplet. The glass pipette attracts the droplet by capillary action and the droplet remains stationary as the slide/mica is moved.

After solution evaporates, rinse the mica with water and dry with compressed air Or by Michalet et als Dynamic molecular combing procedure as described above or by the ASP procedure described above.

Optionally the single stranded DNA can be coated with single strand binding protein (Amersham)

Single stranded DNA can be labelled by Acridine dyes.

Stretched out single stranded molecule can be probed with single stranded DNA by hybridisation at 5 degrees C. below the Tm of the oligonucleotide probe. It is preferable to use LNA oligonucleotides at low salt concentration, 50 mM NaCl or PNA at 0 or 5 mM NaCl.

Example 10

Ligation Assay on Single Molecule Array

Target preparation is essentially as for SNP typing/resequencing section and target analysis
Mix:
5× ligation buffer*
Solution oligonucleotide 5-10 pmol, labelled with fluorescent dye on 3' end and phosphorylated on 5' end *Thermus thermophilus* DNA ligase (Tth DNA ligase) 1 U/ul,
Target Sample
Add to centre of array
Add coverslip over the top of array area and seal edges with rubber cement Place at 65° C. for 1 hr.
*5× ligation buffer is composed of 100 mM Tris-HCL pH 8.3, 0.5% Triton X-100, 50 mM MgCl, 250 mM KCl, 5 mM NAD+, 50 mM DTT, 5 mM EDTA In this example different sequences that define the allele of a SNP are placed in adjacent spots in the microarray, by the spotting methods described. The last base of these sequences overlap the variant base in the target. The oligonucleotide on the array are spotted with 5' amination. The 3' end is free for ligation with the 5' phosphorylated solution oligonucleotide. Alternatively the array oligonucleotide can be 3' aminated and 5' phosphorylated. The solution oligonucleotide can be phosphorylated and labelled on the 5' end. The solution oligonucleotide is preferably a mixture of every 9mer (Oswel, Southampton, UK).

Example 11

SNP/Mutation Typing and Resequencing by Mini-Sequencing on Arrays

The sample anneals to arrayed primers which promote DNA polymerase extension reactions using four fluorescently labelled dideoxynucleotides. In these examples both strands of the target can be analysed simultaneously. But in other cases it may be chosen to use single stranded products (e.g. by asymmetric PCR, RNA transcription, selective degradation of one strand or biotinylation of target strand and removal of non-biotinylated other strand by for example, magnetic beads methods known in the art.

From Amplicons

Produce amplicons by methods known in the art (<1000 bp) covering the desired region, ethanol precipitate and bring up in 12.5 ul water. Optimally the amplicons should be 100 bases or less. If they are longer than 200 base pairs then the following fragmentation protocol must be used. Fragment the amplicons as follows: To the 12.5 ul add 1.5 ul of Buffer (500 mM Tris¬HCl. pH (0.0; 200 mM (NH4)2SO4). Add 0.5 U (1 U/ul) of Shrimp Alkaline Phosphatase (Amersham). Add 0.5 ul of thermolabile Uracil N-Glycosylase (Epicentre). Incubate at 37 for one hour and then place at 95 degrees for ten minutes. Check fragmentation on a gel (successful if no intact PCR is detected).

From Genomic DNA

Genomic DNA can be extracted and purified

Digest DNA with restriction enzyme or random fragmentation (e.g. DNAs1 treatment)

Restriction Digest:
DNA X ul for 1 ug
Reaction 3 10× Buffer 5ul
EcoR1 2 ul (20 units)
Water Y ul to a final volume of 50 ul
Incubate 37 degrees for 16 hours
Stop reaction by 72 degrees C. for 10 minutes
Purify digested DNA using a commercial purification kit (Zymo Research's DNA clean and Concentrator) as per supplied protocol Cot 1 DNA can be used at this stage to remove repetitive DNA and/or can be added to array hybridisation/reactions for in situ suppression of hybridisation of probes to repetitive DNA by blocking the repetitive DNA by hybridisation to the Cot-1 DNA.

Ex situ depletion of repetitive sequence:
Cot-1 DNA (Gibco BRL) is labelled with biotin using Biotin Chem-Link kit (Boehringer Mannheim) as per manufacturers protocol and purified with Sephadex G50 Columns (Amersham Pharmacia) as per manufacturers protocol.

A 700 ng amount of source DNA is hybridised with 35 ug (50 fold excess) of biotin-labelled Cot-1 DNA.

Streptavidin magnetic particles (Boehringer Mannheim) are prepared according to manufacturers instructions, 4.4 mg to a final 125 ul volume The Streptavidin-magnetic particles are applied to the target DNA-biotin-labelled Cot1 DNA (100 ul). After incubation f the Magnetic bead captured Cot-1 fraction was separated to the side of the tube with a magnet, and the supernatant containing the target DNA pipetted to a fresh tube. The magnetic separation is repeated, and then the target DNA supernatant is purified using a QIAex II kit (Qiagen).

In situ Blocking of Cot-1 fraction

Add 25-125 ug (or 100 fold excess to target DNA) of Cot-1 DNA directly to hybridisation/reaction mix Apply directly to the array or The DNA can be randomly amplified by random primers using reagents for Spectral Genomics (SG) (Houston, Tex.) Human Bac array and BioPrime labelling kit form Gibco/13RL.

Add SG Sterile Water (orange vial) to xul (at least 100 ng not more than 1 ug) of digested DNA to bring volume to 25 ul. Add 2.5× random primer/reaction buffer (Gibco). Mix the samples well and boil for 5 minutes and place the samples on ice for 5 minutes On ice add 2.5 ul of SG labelling Buffer (yellow vial) to each sample Optionally add 1.5 ul Cy5-dCTP or Cy3-cCTP to the samples (In some sequencing embodiments, a mixture of for example Cy5-dCTP and Cy3-dATP may be added to intrinsically label the DNA strand with two labels; the 5 other combinations of dNTPs may also be required in separate reactions)

Add 1 ul Klenow Fragment (Gibco) to the sample and mix well by tapping and recollecting by centrifugation Incubate the sample at 37 degrees from 2.5 hours (enough for one or two array hybridisations/reactions) to overnight (produces sufficient material for several array hybridisations). The probe will range in size between 100 and 500 bp. For sequencing applications it may be desirable to have longer sequences and for this the concentration of the random primer can be diluted (the concentration of random primer to use to get a particular random primer product must be determined empirically).

Stop the reaction by adding 0.5 ul 0.5M EDTA pH 8 and incubating at 72 for 10 minutes. Place samples on ice until use or freeze at −20 degrees C.

If necessary the random prime labelled DNA can again be depleted for any sequences from the Cot-1 fraction by magnetic separation with Cot-1 DNA.

Alternatively or in addition Cot-1 DNA can be added to the hybridisation/reaction mix Fragmentation Methods Fragmentation of the genome to the desired size can be done by DNAse 1 treatment. This needs to be optimised for a particular enzyme.

Fragmentation by sonication can also be optimised to give long fragments of a desired length Mini-Sequencing Wash enhanced aminosilane slides with milliQ water before using and dry (e.g place on 58 C heating plate). Denature the sample DNA for 6 minutes at 95 degrees. Centrifuge and put on ice. Add 5ul of dye terminators (e.g Texas Red-ddATP, Cy3-ddCTP, Fluorescein-ddGTP, Cy5-ddUTP, all 50 uM) and diluted Thermosequenase (4 U/ul), mix and pipette onto slide covering region carrying the array. Immediately cover with a piece of Parafilm to cover the array area if the array has been printed on a coverslip or place Parafilm or coverslip over array if it has been printed on a slide. Lifter coverslips (Erie Scientific) are preferably used. Incubate slide 25 minutes at 58 C. Remove Parafilm/coverslip, wash slide 2 minutes in 95 degree milliQ water, 3 minutes in 0.3% Alcanox solution and 2 minutes in 95 degree milliQ water.

Excitation Wavelengths 4 lasers 488 nm (FITC)

543 nm (Cy3)

594 nm (Texas Red)

633 nm (Cy5)

Emission Wavelengths 8 position filter wheel with narrow band pass filters 530 nm (1-41TC)

570 nm (Cy3)

630 nm (Texas Red)

670 nm (Cy5)

A droplet of slowfade Light antifade reagent (Molecular probes) is added to minimize photobleaching and cover with a coverslip.

If non-specific sticking of for example labelled nucleotides (seen by for example signals outside the regions carrying the microarray spots, then prehybridisation of the array can be done (e.g. in a 25 ml volume in a 50 ml falcon tube) with a buffer containing 1% BSA, 0.1% SDS (and or Sarksyl) and optionally Cot1 DNA, poly(A) DNA, tRNA.

Errors are eliminated by methods of this invention, for example by an algorithm or by enzymatic methods such as the use of Apyrase. For the latter, 8 mU of Apyrase (Sigma) is added to the reaction mix on the array.

The array for this experiment can be made as in Example X above (with reduction of synthesis cell dimension and step size) or by spotting 5' aminated oligonucleotides onto enhanced arainosilane slides in DMSO:Water at an appropriate dilution (e.g. 50-500 nM range).

Example 12

Haplotyping by Hybridisation of Multiple Differentially Labelled Probe Sets

The array can define the first SNP

Subsequent SNPs can be analysed by further probing along the molecule with different colour sets labelling each subsequent SNP site If this is done for a multiplicity of SNPs over a long range, then the signals from each may not appear as a point source. To read SNPS along a single molecule in this case, either measures must be taken to ensure probes are far enough a part to define a radius over which signals assigned to a single molecule or preferably:

The target molecule is collapsed to a point source by incubating with 5 ug/ml Avidin in 2S SSC, 1% BSA, 0.1% Tween 20 for 30 minutes at 37 degrees C.

Example 13

Haplotyping by Viewing Position of Blank Probe Set Along the Genome

Target DNA is labelled before or after capture and horizontalisation by probing with one of the several methods described in this patent. The design of the assay is as follows:

Make Biallelic probe set for each SNP, each probe in the set of two labelled with a different label e.g. Fluorosphere wavelength in the green or in the red Make sequence specific Biallelic probe sets for each of the SNPs to be analysed, using the same two colours in the majority of probes of overlapping segments and computes the sequencing from the hybridisation data from each area, matching to the draft genome sequence where available assigning probabilistic scores. The data is presented with a colour chart indicating regions of high certainty and regions of lower certainty. The regions of high certainty can be used in genetic studies.

Example 14

Single Molecule Sequencing by Hybridisation

There are several schemes with which single molecule sequencing by hybridisation can be achieved. The following gives a number of strategies. Experimental steps that are common are described under separate headings. Other methods are elsewhere in the description of methods.

Sequencing Strategy Example A

Sequencing of spatially addressably captured genomic DNA is done by iterative probing with 6 mer oligonucleotides. There are 4096 unique 6 mers complementary pairs. Each oligonucleotide is added one after the other. The position(s) of binding of each oligonucleotide is recorded before addition of the next oligonucleotide. The target is preferentially in a linearised single stranded form.

Sequencing Strategy Example B

Sequencing of spatially addressably captured genomic DNA is done by iterative probing with sets of 6 mer oligonucleotides. There are 4096 unique 6 mers, these are split into groups of 8 containing 512 oligonucleotide each. Each probe is labelled via a C12 linker arm to a dendrimer (Shchepinov et al Nucleic Acids Res. 1999 Aug. 1; 27(15):3035-41) which carries many copies of this probe sequence (this construct is made on an Expedite 8909 synthesizer or an ABI 394 DNA synthesizer or custom made by Oswel). The 512 probe constructs of each set are hybridised simultaneously to the secondary genomic array. Following this the position of binding of the probes and the identity of the probes is detected by hybridisation of a library of microspheres, within which each microsphere is coated with a complementary sequence to one of the probe sequences (e.g. by first coating microsphere with streptavidin (Luminex) and then binding biotinylated oligonucleotides to this as described above or binding aminated oligonucleotides by carbodiimide coupling; see also Bioconjugate techniques, Greg T. Hermanson Academic Press). The arms of the dendrimer form multiple interactions with the multitude of oligonucleotide copies that coat the microsphere in <400 mM Monovalent salt, Na at 40 degrees C. or above. The microsphere in one of a coded set, ratiometrically dyed with a two or more dyes (100-1000 different coded beads are available (Lumonics). The spectral properties of these beads that now decorate the DNA in the secondary array and their position of binding are recorded. The probes are then denatured which releases the whole complex. The array can then be probed with the 8 other probe sets in a stepwise manner. The probe concentrations are configured such that only some of the sites on the DNA are occupied, but analysis of the multitude of copies of each genomic fragment within a microarray spot enables information about all the sites that are occupied to be worked out. The information obtained from the experiment is fed into the sequence reconstruction algorithm. Optionally the 8 sets can be further split and hybridisation is done on multiple copies of the array. In this way far fewer coding beads need be used.

Sequencing Strategy Example C

Sequencing of spatially addressably captured genomic DNA is done by iterative probing simultaneously with sets of non overlapping or minimally-overlapping sequences added together and substantially overlapping sequences are added separately. Non-overlapping and minimally overlapping sets of sequences from this set of 4096 are determined algorithmically. Each set is added one after the other. The position(s) of binding of oligonucleotides in each set is recorded before addition of the next oligonucleotide. The target is preferentially in stretched single stranded form.

The information that is passed onto the algorithm for sequence reconstruction is the identity of the sequences in the non overlapping set, that they do not overlap, the positions of binding of probes from the set. This is preferably done with a high resolution method such as AFM and the probe molecules need not be labelled. In another embodiment each probe is labelled for example, with a streptavidin molecule separated by a linker. The draft sequence of the genome is used to reconstruct the sequence.

Sequencing Strategy D

The 4096 oligonucleotides are grouped into sets, in this example in sets of sixteen each containing 256 oligonucleotides (oligonucleotides in each set are chosen by algorithm to minimally overlap in sequence). Each set is used in a series of hybridisation to a separate copy of the secondary array. After simultaneous hybridisation of the 265 oligonucleotides in the set and recording of the position of their binding they are denatured. Next one of the oligonucleotides from the set is omitted and the resulting set of 255 oligonucleotides is hybridised back to the array. The absence of signals from positions where there was previously signal tells us the identity of the oligonucleotide that bound in that position before as being the oligonucleotide that is omitted in the present run. This is iterated with a different oligonucleotide from the set and so on, 256 times so that information is obtained from sets in which one of the 256 is omitted each time. The oligonucleotides are bound in saturating concentrations. The information that is obtained is passed onto the algorithm for sequence reconstruction.

Sequencing Strategy Example E

Sequencing of spatially addressably captured genomic DNA is done by iterative probing with complementary pairs of 6 mer oligonucleotides, both oligonucleotides labelled with the same label. There are 4096 unique 6 mer complementary pairs. Each pool is added to a separate secondary array (capture probes to which the genomic sample array has been spatially addressably captured and combed). After each probing step the 6 mers are be denatured and then a different complementary pair is added.

The target is preferentially double stranded in this example and not denatured in situ. However denaturation in situ is an alternative.

Each of one the 256 BainsProbes in each pool will be hybridised to a secondary array. To reduce time and the affects of attrition on the secondary array, multiple BainsProbes are annealed at one time. In this example two will be labelled at one time and preferentially, these will be differentially labelled, for example each of the 2 could be labelled with Cy3 or Cy5 dyes or a red fluorescent or green fluorescent Fluorosphere (a more complex coding could be devised or alternatively there would be no labelling and it would be the task of the algorithm to reconstruct the sequence on that basis). After annealing, the position of the probes is recorded with respect to each other and the markers. In some embodiments the DNA probes can be denatured from the target DNA, before another set is added (or after several sets are added) but in the present example, the BainsProbes are not removed after hybridisation. Instead, after recording the positions of probe binding, the next pair of probes are added. This will need to be iterated 128 times to go through all the probe pairs. If each iteration is approximately 10 minutes for each addition, then the sequencing will be complete within 24 hours. This could be speeded up further if more than 2 oligonucleotides are added at a time, for example 80 oligonucleotides added at a time would allow whole genome sequencing in about an hour; each of the 80 would not need to hybridise to every copy that is captured within a microarray spot, for example if there is 2000 50 kb molecules captured in one spot, then each molecule need only be labelled with say, 8 probes. This can aid in one sequence preventing the binding of another by forming overlap with another.

Molecular beacons can be used as probes: here there is no fluorescence when the oligonucleotide is scanning the molecule, only signal when it forms a stable enough duplex to unwind the stem and release the fluorophore from quenching. Two types of molecular beacons can be used, one based on FRET and the other based on electron transfer (Alto-Tec, Heidelberg). It is likely that as sequence reconstruction in this case will utilise the draft sequence of the genome.

Sequencing Strategy Example F

Sequencing of spatially addressably captured genomic DNA is done by iterative probing with 8 mer oligonucleotides. Each 8mer contains 6 unique bases and two degenerate positions, in this example, the central two bases are degenerate. There is 4096 different probes identified by their 6 unique positions but each of these carry 16 different sequences due to the degenerate positions (these will be referred to as BainsProbes after Bains and Smith Journal of theoretical biology 135: 303-307 1988). The 4096 BainsProbes are split into 16 pools of 256 BainsProbes (this is an arbitrary choice and they could be split into 4 pools of 1024 if the number of arrays are limiting) with each pool containing sequences approximately matched for Tm. Each pool is added to a separate secondary array (capture probes to which the genomic sample array has been spatially addressably captured and combed).

Each of one the 256 BainsProbes in each pool is hybridised to a secondary array. To reduce time and the affects of attrition on the secondary array, multiple BainsProbes are annealed at one time. In this example two are labelled at one time and preferentially, these are differentially labelled, in this example each of the 2 are labelled with either Cy3 or Cy5 dye or a red fluorescent or green fluorescent Fluorosphere (a more complex coding can be devised or alternatively there would be no labelling and it would be the task of the algorithm to reconstruct the sequence on that basis). After annealing, the position of the probes is recorded with respect to each other and the markers. In some embodiments the DNA probes can be denatured from the target DNA, before another set is added (or after several sets are added) but in the present example, the BainsProbes are not removed after hybridisation. Instead, after recording the positions of probe binding, the next pair of probes are added. This will need to be iterated 128 times to go through all the probe pairs. If each iteration is approximately 10 minutes for each addition, then the sequencing will be complete within 24 hours. This could be speeded up further if more than 2 oligonucleotides are added at a time, for example 80 oligonucleotides added at a time would allow whole genome sequencing in about an hour; each of the 80 would not need to hybridise to every copy that is captured within a microarray spot, for example there may be 2000 50 kb molecules captured in one spot, and each individual molecule copy need only be labelled with say, 8 probes. This can aid in one sequence preventing the binding of another by forming overlap over a complementary region.

Molecular beacons can be used as probes: here there is no fluorescence when the oligonucleotide is scanning the molecule, only signal when it forms a stable enough duplex to unwind the stem and release the fluorophore from quenching. Two types of molecular beacons can be used, one based on FRET and the other based on electron transfer (Alto-Tec, Heidelberg). It is likely that as sequence reconstruction in this case will utilise the draft sequence of the genome.

Sequencing Strategy Example G

Sequencing of spatially addressably captured genomic DNA is done by iterative probing with 13 mer oligonucleotides (this length can form stable duplex at room temperature). Each 13mer contains 6 unique bases and 7 degenerate positions, for example, 8 bases at the 5' end are degenerate (will be called stabiliser probes). Although we have the stability of a 13 mer we will only have the sequence information of a 6mer. There will be 4096 different probes identified by their 6 unique positions but each of these will carry ca. 16,384 different sequences due to the degenerate positions. In this example the concentration of oligonucleotide will be 100 to 1000 fold higher than in example A. The 4096 Stabiliser Probes will be split into 8 pools of 512 (this is an arbitrary choice and they could be split into 4 pools of 256) with each pool containing sequences approximately matched for Tm. Each pool will be added to a separate secondary array (capture probes to which the genomic sample array has been spatially addressably captured and combed).

Each of one the 128 BainsProbes in each pool will be hybridised to a secondary array. To reduce time and the affects of attrition on the secondary array, multiple BainsProbes are annealed at one time. In this example two will be labelled at one time and preferentially, these will be differentially labelled, for example each of the 2 could be labelled with Cy3 or Cy5 dyes or a red fluorescent or green fluorescent Fluorosphere (a more complex coding could be devised or alternatively there would be no labelling and it would be the task of the algorithm to reconstruct the sequence on that basis). After annealing, the position of the probes is recorded with respect to each other and the markers. In some embodiments the DNA probes can be denatured from the target DNA, before another set is added (or after several sets are added) but in the present example, the BainsProbes are not removed after hybridisation. Instead, after recording the positions of probe binding, the next pair of probes are added. This will need to be iterated 128 times to go through all the probe pairs. If each iteration is approximately 10 minutes for each addition, then the sequencing will be complete within 24 hours. This could be speeded up further if more than 2 oligonucleotides are added at a time, for example 80 oligonucleotides added at a time would allow whole genome sequencing in about an hour; each of the 80 would not need to hybridise to every copy that is captured within a microarray spot, for example if there is 2000 50 kb molecules captured in one spot, then each molecule need only be labelled with say, 8 probes. This can aid in one sequence preventing the binding of another by forming overlap with another.

Molecular beacons can be used as probes: here there is no fluorescence when the oligonucleotide is scanning the molecule, only signal when it forms a stable enough duplex to unwind the stem and release the fluorophore from quenching. Two types of molecular beacons can be used, one based on FRET and the other based on electron transfer (Alto-Tec, Heidelberg). It is likely that as sequence reconstruction in this case will utilise the draft sequence of the genome.

The above examples are all done with 6 mer probes, however the strategies can be implemented with oligonucleotides shorter than 6 nt, in which case there will be fewer cycles but more stabilising chemistries such a LNA will be used. Alternatively oligonucleotides longer than 6 nt can be used in which case there will be more cycles.

These three strategies serve as examples but methods from any of these can be adapted from one to the other and there are several other specific means which are apparent from the methods and protocols described in this invention. For example, each probe can be ligated to a random library of ligation molecules, this would serve to stabilise the interactions and eliminate mismatches.

Getting Additional Experimental Validating Sequence Information

To get further information about sequence, during preparation the DNA sample can be internally labelled with combinations of base labelling fluors as suggested in the random primer labelling section above. In addition where the target DNA of the secondary array is double stranded, optical mapping in which gaps are created at the site of restriction digest can provide sequence and positional information.

The Experimental Apparatus

The edges of the area surrounding the array are raised so that addition and removal of fluids can take place (e.g a microtitre set-up; low intrinsic fluorescence glass bottomed plates area available, e.g. from Whatman Polyfiltronics or custom made glass). Alternatively, the array substrate is sealed to a reaction cell (e.g. Teflon or Teflon coated which makes a good seal with glass) with inlet and outlet ports. Where information from single dye molecules is required, the microscopy set up will be TIRF, preferably with pulsed lasers and time gated detection, with full gamut of measures taken to minimise fluorescence background. Where the probes are labelled with fluorspheres then epi-fluorescence microscopy and excitation with a 100 W mercury lamp can be used. Where the analysis is with AFM, then nanoparticles of different sizes can be used for labelling, analysis will be with tapping mode in Air and a liquid cell will be used for flowing in reagents and washing the array.

Experimental Procedures

Spatially Addressable Capture Arrays

Make arrays by spotting, from microtitre plates to slide, normal terminally aminated phosphodiester oligonucleotides (Eurogentec, Belgium) are spotted as described above. These oligonucleotides may also incorporated a digoxygenin molecule or other label.

Make arrays as above but employ oligonucleotides in which one more base is an LNA base (Proligo). 0.2 uM scale synthesis is sufficient to print thousands of arrays, alternatively for a large number of elements the arrays are more economic to make by combinatorial synthesis)

Make arrays by spotting PNA oligonucleotides (Oswel, UK or Boston Probes, USA)

Target Preparation.

Remove Cot 1 fraction as described and/or add Cot 1 DNA to the DNA to reaction mix Not 1 Digestion Digest genome with Not1 restriction enzyme (NEB) as recommended by supplier.

Separate by affinity capture with a biotinylated probe (preferably LNA on a magnetic bead (as recommended by supplier/described elsewhere in the document) that is complementary to the overhang generated by the Not1 enzyme Alternatively digestion with DNAse 1

Alternatively target preparation can be by the Random Primer labelling protocol given above with the reaction optimised to give long fragments;

If single stranded DNA is to be captured then measures need to be taken to make single stranded DNA e.g by cloning the genomic library of fragments into single stranded M13 vector (see Maniatis) or by other means described above.

Spatially Addressable Target Capture (Secondary Array)

Hybridise target to array (ASP method as described for lambda DNA above). Use as much target DNA as can be tolerated in the reaction mix for example, at least 10 ug of restriction digested DNA or if whole genome amplification by random primei labelling has been done then the amount of DNA obtained after amplification of as little as 500 ng of starting DNA, can be used Optionally in addition, the captured target is ligated to array (for this it would be desirable to dephosphorylate the Not1 digested DNA (as described above) to prevent self-ligation prior to hybridisation to array and the oligonucleotide on the arrays must have a free 5' phosphorylated end). (Tth DNA ligase, 1× Buffer (supplied by Abgene at 65 degrees C.) as described above.

Optionally instead of ligation, the captured target is chemically attached to the surface after hybridisation Preparation and Marker Labelling of Secondary Array The digoxygenin can be added to the array oligonucleotides during their synthesis. Once the target has hybridised an signal amplification reaction can be performed on the digoxygenin so that the point of array capture can be identified Block slide with milk protein supernatant in PBS/Tween 20 (10" at room temperature) and wash with PBS/Tween $1^{st}$ Antibody layer Add Mouse Anti-Digoxygenin Antibody (Roche) diluted 1/250 in milk protein+PBS for. Leave 30" at RT in the dark then do PBS/Tween washes $2^{nd}$ Antibody layer Add Goat Anti-Mouse Alexa Fluor 488/520 (Molecular Probes) 1/50 dilution in milk proein+PBS. Leave 30" at 37 C in dark. Do PBS/tween wash followed by a PBS wash. Dry slide (for example with gentle forced air)

Add Fluorescently labelled LNA oligonucleotides complementary to at least one end of DNA (1-100 pmols) at room temperature, and optionally ligate (Tth DNA ligase, 1× Buffer (supplied by Abgene between room temperature and 65 degrees C.).

Stain the target Genomic DNA with YOYO-1 (Molecular Probes) in a 1 in 1000 or 1 in 2000 dilution (other DNA labels might be used depending on labelling of oligonucleotide probes and markers)

Take image with CCD camera

Making the DNA Accessible to Probing
  Denaturing the DNA in situ
    Denature DNA by alkali flow or
    Alternatively heat the DNA to 70 C in 70% Formamide for 2 minutes and dehydrate by series of ethanol washes (70, 90 and 100%)
  Probe double stranded DNA by strand invasion e.g. Use of LNA or PNA
  Probe double stranded DNA by RecA mediated binding
  Preparation of RecA-Target DNA Complex. Nucleoprotein filaments were first formed by incubating with 1 L of 68.2 M RecA (2.58 g/L) and 3 L of 1.74 M probe DNA (20 ng/L) at 37 C in a buffer consisting of 25 mM Tris-acetate (pH 7.5) and 1 mM magnesium acetate. After 1 min, 1 L of 10 mM ATPS and 1 L of 17.6 M oligo(dT) (80 ng/L) were added to bring the final volume to 10 L, and the reaction proceeded at 37 C for 10 min. Linearised double-stranded DNA targets (80 ng) were added, the buffer was adjusted to 25 mM Tris-acetate (pH 7.5), 4 mM magnesium acetate, 10 mM dithiotbreitol, and 2.7 L of BSA (0.1 mg/mL), and incubation was continued at 37 C for 30 min. The final target reaction volume was 27 L. To visualize RecA-DNA complexes by AFM, the samples were purified by incubating with 200 L of Strata Clean resin (Stratagene) for 30 min and centrifuging at 3500 rpm, immediately adjusting the magnesium acetate to a final concentration of 4 mM. Also, to identify the sequence-specific site protection of target DNA by nucleoprotein filaments, 15 units of EcoRI enzyme, 5 L of 80 mM magnesium acetate, and 5 L of 250 mM potassium acetate were added and the reaction was continued at 37 C for 1 h (50 L reaction volume).
  Use target in single stranded form as described above
Annealing of Oligonucleotide Sets and Detection
  The DNA array is placed on a temperature control device such as a thermocycler fitted with a flat block (microscopy will then be from above)
  Hybridisation can be done in 3.5M Tetramethyl ammonium Chloride that reduce the effects of base composition (see section D above for a list of other possible buffers) in which case all annealing will be done at one or two temperatures. Hybridisation of short oligonucleotides with 4-6 SSC
  Add first set of oligonucleotide probes at a concentration between 1 nM-1 uM depending oligonucleotide length and chemistry
  Concentrations can be adjusted so that some but not all sample molecules give signal (for example, optimised so that 1 in 12 oligos give a signal with a particular oligonucleotide sequence).
  This is done at a temperature that is optimal for the Tm. For DNA oligonucleotides this may be between 0 and 10 degrees C. For LNA/PNA oligonucleotides a higher temperature can be used eg room temperature. If for example an enzymatic reaction is performed e.g. ligation to random 9mers then a higher reaction temperature e.g. 65 degrees C. with Tth DNA ligase, can be used.
  Use rolling circle amplification to amplify signal from each probe. In this example the probes are bipartite, with sequence complementary to target and circler oligo round which polymerisation extends with Sequenase enzyme and single stranded binding protein (SSB) essentially as described (Thong et al PNAS 98: 3940-3945)
Oligonucleotide Conjugation to Oligonucleotides or Microspheres
  Oligonucleotides can be coupled to microspheres (Luminex, Austin Tex.) or nanospheres by a one step carbodiimide coupling method. Each coupling reaction contains 10.1 uM of amino-substituted oligonucleotide and 1×108 microspheres/ml in 0.1 MES. PH 4.5. EDC is added at 0.5 mg/ml and reaction is incubated for 30 minutes st room temperature followed by a second EDC addition and incubation. The coupled microspheres are washed and stored at 4 degrees C. in the same buffer.
  Dendrimers are coupled to oligonucleotide-microspheres in [tetramethylammonium chloride (TMA) buffer: 0.01% SDS, 50 mM Tris, 3.5 M TMA, 0.002 M EDTA or 2-6× sodium citrate (SSC) buffer: 0.9 M NaCl, 0.03 M trisodium citrate. —(2×SSC gives more specificity of binding at 40 degrees C. Dendrimers are made essentially as described.
  Denaturing Oligonucleotides
  Oligonucleotides can be denatured under gently agitation by one or more of the following treatments
    *High Stringency buffer e.g. 0.1×SSC or
    High Stringency buffer e.g. 0.1×SSC followed by water or Tris EDTA or
    Alkali buffer, 100 mM Sodium Carbonate/Hydrogen carbonate, room temperature
    *And/or Heat to 37
    And/or Heat to 37 to 70 degrees C.
  Harshness of treatment that can be tolerated is determined by the number of cycles that need to be performed.
  It is not essential to remove all probes. But it is important to image which probes remain binding after treatment.
  Less harsh treatments labelled with asterisk above are preferred.
Sequence Reconstruction, Re-Mining and Validation
  A first pass at reconstructing the sequence is attempted. This will identify regions with gaps and low confidence.
  As the draft human genome sequence is known, any gaps can be filled in by probing with specific oligonucleotides, the gapped/low confidence region on a further array and this process can be re-iterated (i.e. see if additional information allows reconstruction, if not add further probes to same array or separate array and repeat).
  Sequence reconstruction can be performed on a network of desktop computers, e.g. IBM compatible Personal computer, Apple personal computer, or Sun Microsystem computer. Such networks can be very large
  In some instances sequence reconstruction is on a supercomputer
  The results will be presented in a graphical, interactive format.
  Low confidence regions that are persistent will be indicated as such on a macro, chromosome by chromosome report of the regions sequenced. The confidence assigned to each base will be available, which is not the case in present methods.
  Avoiding Mismatch Errors
  Conditions will be stringent enough to prevent a 5mer mismatch from hybridising. Furthermore, markers can be used to label mismatches or methods can be used to destroy mismatches, for example, the mismatch repair system of *Escherichia coli*, provides proteins, MutL, Muth and MutS which singly or in combination can be used to detect the site of a mismatch; T4 endonuclease IV can also do this. In addition treatment by tetraethylammoniura chloride/potassium permanganate, followed by hydroxylamine can cleave the site of mismatch and this will be seen as a contraction in the DNA. It is likely that mismatches will only occur when a 6mer is stabilised by flanking contiguous stacking oligonucleotides. This effect can be minimized by making oligonucleotides in which one end is phosphorylated (disrupts intimate coaxial stacking) or by adding a bulky group at the end.
  For complete de novo sequencing, for example of organisms where no reference sequence is available, the experimental procedure is exactly the same but the task of the algorithm is greater. Supercomputers may be needed for sequence reconstruction depending on the quality of data that is obtained.

The data is deconvoluted for ordering along the molecule and data about 'order and approximate distance from other probes is taken into account. A list with orders is then present to a \sequencing by hybridisation algorithm. In one example of the reconstruction strategy the algorithm then splits the regions of the genome into a series of overlapping segments and computes the sequencing from the hybridisation data from each area, matching to the draft genome sequence where available assigning probabilistic scores. The data is presented with a colour chart indicating regions of high certainty and regions of lower certainty. The regions of high certainty can be used in genetic studies.

The results are also cross-validated by Sanger sequencing technologies and with this comparison a heuristic or knowledge based system will be built up over time, enabling more accurate sequence. The aim would be to get confidences higher than error rates for common enzymes, e.g. 99.9% confidence. Ultimately the sequencing may be run in parallel with other whole genome sequencing technologies to further increase confidence.

With this method it is possible that unless specific measures are taken algorithms could be confounded by heterozygocity over the regions. Therefore it will be preferable to use biallelic probes to isolate haplotype tags which seed a region of linkage disequilibrium. This information about the haplotype structure of the genome will soon become available through international efforts.

Example 15

Two-Colour Gene Expression Analysis

RNA is extracted by methods known in the art e.g by using the TriZol kit.

Preparing Single Molecule Arrays for Gene Expression Analysis

Single molecule arrays of two types can be prepared for gene expression analysis. The first is oligonucleotide arrays, which are either synthesized in situ or are pre-synthesized and spotted. The second is by spotting of cDNAs or PCR product. The former can be spotted essentially as described in example X. For the latter the optimal concentration to spot the oligonucleotides to get single molecule detection with a method of choice would need to be determined empirically, as already described. Following this cDNA arrays will be spotted essentially as described onto for example, aminosilane arrays using 50% DMSO as spotting buffer.

Preparing Fluorescently Labelled cDNA (Probe) by Brown/DeLisi Protocol or an Adaptation Thereof:

For single molecule counting based on analysis of a single dye molecule, the cDNA must be primer labelled where the primer carries a single dye molecule or alternatively carries a single biotin molecule or is aminated for attachment to single beads.

In a modification, the cDNAs are labelled with incorporation of ddNTPs so that short fragments are created.

1. To anneal primer, mix 2 ug of mRNA or 50-100 μg total RNA with 4 ug of a regular or anchored oligo-dT primer in a total volume of 15.4 ul:

|  | Cy3 | Cy5 |  |
| --- | --- | --- | --- |
| mRNA (1 γ/λ) | x λ | Y λ | (2 μg of each if mRNA, 50-100 μg if total RNA) (Anchored: 5'-TTT TTT TTT TTT TTT TTT TTV N-3') This primer may be labelled at the 5' end with a dye |
| Oligo-dT (4 γ/λ) | 1 λ | 1 λ | molecule e.g Cy3 or Cy5. This can be specified when the oligonucleotide is ordered from e.g.0swel, Southampton, UK) |
| ddH₂O (DEPC) | to 15.4 λ | to 15.4 λ |  |
| Total volume: | 15.4 λ | 15.4 λ |  |

2. Heat to 65° C. for 10 min and cool on ice.
3. Add 14.6 μL of reaction mixture each to Cy3 and Cy5 reactions:

| Reaction mixture | λ | ... Unlabeled dNTPs | Vol. | Final conc. |
| --- | --- | --- | --- | --- |
| 5X first-strand buffer* | 6.0 | dATP (100 mM) | 25 uL | 25 mM |
| 0.1M DTT | 3.0 | DCTP (100 mM) | 25 uL | 25 mM |
| Unlabeled dNTPs | 0.6 | DGTP (100 mM) | 25 uL | 25 mM |
| Cy3 or Cy5 | 3.0 | DTTP (100 mM) | 10 uL | 10 mM |
| (1 mM, Amersham)** |  | ddH2O | 15 uL |  |
| Superscript II | 2.0 |  |  |  |
| (200 U/uL, Gibco BRL) |  |  |  |  |
| Total volume: | 14.6 λ | Total volume: | 100 uL |  |

*5X first-strand buffer: 250 mM Tris-HCL (pH 8.3), 375 mM KCl, 15 mM MgCl2)
**Fluorescent nucleotides are omitted when a labelled primer is included or when labelling is through a labelled ligation primer (as described below)

4. Incubate at 42° C. for 1 hr.
5. Add 1 A. SSII (RT booster) to each sample. Incubate for an additional 0.5-1 hrs.
6. Degrade RNA and stop reaction by addition 15 μl of 0.1N NaOH, 2 mM EDTA and incubate at 65-70° C. for 10 min. If starting with total RNA, degrade for 30 min instead of 10 min.
7. Neutralize by addition of 15 μl of 0.1N HCl.
8. Add 380 μl of TE (10 mM Tris, 1 mM EDTA) to a Microcon YM-30 column (Millipore). Next add the 60 μl of Cy5 probe and the 60 μl of Cy3 probe to the same microcon. (Note: If re-purification of cy dye flow-through is desired, do not combine probes until Wash 2.)
9. WASH 1: Spin column for 7-8 min. at 14,000×g.
10. WASH 2: Remove flow-through and add 450 ul TE and spin for 7-8 min at 14,000×g. It is a good idea to save the flow trough for each set of reactions in a separate microcentrifuge tube in case Microcon membrane ruptures.
11. WASH 3: Remove flow-through and add 450 ul 1×TE, 20 μg of Cot1 human DNA (20 μg/μl, Gibco-BRL), 20 μg polyA RNA (10 μg/μl, Sigma, #P9403) and 20 μg tRNA (10 μg/μl, Gibco-BRL, #15401-011). Spin 7-10 min. at 14,000×g. Look for concentration of the probe in the microcon. The probe usually has a purple color at this point. Concentrate to a volume of less than or equal to the 28 ul. These low volumes are attained after the centre of the membrane is dry and the probe forms a ring of liquid at the edges of the membrane. Make sure not to dry the membrane completely!
12. Invert the microcon into a clean tube and spin briefly at 14,000 RPM to recover the probe.
Using a 22×60 mm coverslip use a total volume of 35 ul composed of 28 ul Probe and TE, 5.95 ul 120×SSC, 1.05 ul 10% SDS
*20×SSC: 3.0 M NaCl, 300 mM NaCitrate (pH 7.0)

13. Adjust the probe volume to 28 ul column above.
14. For final probe preparation add 4.257λ 20×SSC and 0.75λ 10% SDS. When adding the SDS, be sure to wipe the pipette tip with clean, gloved fingers to rid of excess SDS. Avoid introducing bubbles and never vortex after adding SDS.
15. Denature probe by heating for 2 min at 100° C., and spin at 14,000 RPM for 15-20 min.
16. Place the entire probe volume on the array under the appropriately sized glass cover slip.
17. Hybridize at 65° C. for 14 to 18 hours in a custom slide chamber with humidity maintained by a small reservoir of 3×SSC (spot around 3-6λ 3×SSC at each corner of the slide, as far away from the array as possible).

II. Washing and Scanning Arrays:
1. Ready washes in 250 ml chambers to 200 ml volume as indicated in the table below. Avoid adding excess SDS. The Wash 1A chamber and the Wash 2 chambers should each have a slide rack ready. All washes are done at room temperature.
2.

| Wash | Description     | Vol (ml) | SSC         | SDS (10%) |
|------|-----------------|----------|-------------|-----------|
| 1A   | 2x SSC, 0.03% SDS | 200    | 200 ml 2x   | 0.6 ml    |
| 1B   | 2x SSC          | 200      | 200 ml 2x   | —         |
| 2    | 1x SSC          | 200      | 200 ml 1x   | —         |
| 3    | 0.2x SSC        | 200      | 200 ml 0.2x | —         |

3. Blot dry chamber exterior with towels and aspirate any remaining liquid from the water bath.
4. Unscrew chamber; aspirate the holes to remove last traces of water bath liquid.
5. Place arrays, singly, in rack, inside Wash I chamber (maximum 4 arrays at a time). Allow cover slip to fall, or carefully use forceps to aid cover slip removal if it remains stuck to the array. DO NOT AGITATE until cover slip is safely removed. Then agitate for 2 min.
6. Remove array by forceps, rinse in a Wash II chamber without a rack, and transfer to the Wash II chamber with the rack. This step minimizes transfer of SDS from Wash I to Wash II.
7. Wash arrays by submersion and agitation for 2 min in Wash II chamber, then for 2 min in Wash III (transfer the entire slide rack this time).
8. Spin dry by centrifugation in a slide rack in a Beckman GS-6 tabletop centrifuge at 600 RPM for 2 min
9. Analyse arrays immediately on a single molecule sensitive detector such as the Light station (Atto-tec).

Instead of performing step 1 in the above protocol with labelled target cDNA, because the requirement of the assay of this invention is a single dye molecule, a target labelling procedure can be omitted. Thence, unlabelled cDNA or Poly A mRNA or total RNA can be hybridised directly. This is then followed by hybridisation of either:
1. A random library of n-mers (e.g 8-10 m mers) which are labelled 5' phosphorylated and 3' labelled are ligated to arrayed sequence specific oligonucleotide probes (e.g to as can be made by Febit or Xeotron, or can be spotted), templated by the target mRNA
2. A library of sequence specific probes which are labelled as above are ligated to oligonucleotides in an n-mer array, templated by the target mRNA Where Total RNA is used blocking sequences are used to mop up ribosomal RNAs, small nuclear RNAs and transfer RNAs.

In the above process, several dye molecules are incorporated into each single cDNA molecule. If the density of the array is low enough signals from a single species can be distinguished by their spatial co-localization and that they are a single colour. The single molecules will form a Poisson distribution so there will be some molecules that cannot be resolved but these will be minimal if the spacing is far enough apart. In an alternative method the oligo(T) primer s end labelled. This can be labelled with a single dye molecule, multilabelled with dendrimers or labelled with a Fluorospher (Molecular Probes).

The results of the assay are based on the ratio of the number of molecules (or colocalized sets of molecules) counted for each of the populations.

Single Molecules can be counted on low density arrays when using small number of cells (~1000) and when using normal amounts (e.g $10^6$). Alternatively arrays, can be single molecule arrays by functionalisation. In this case, small amounts of sample material 100-1000 cells must be used to achieve the single molecule functional array which can be used to count single molecules.

Example 16

Making Chemical Arrays and Use for Ligand-Protein Binding Assay

Aminosilane (APTES) slides from Asperbio (Estonia) made on low fluorescence glass (Knittel Glaser, Germany) are derivatized (Gavin MacBeath, Angela N. Koehler, and Stuart L. Schreiber J. Am. Chem. Soc., 121 (34), 7967-7968, 1999) to give surfaces that are densely functionalized with maleimide groups. To achieve this, one face of each slide is treated with 20 mM N-succinimidyl 3-maleimido propionate (Aldrich Chemical Co., Milwaukee, Wis.) in 50 mM sodium bicarbonate buffer, pH 8.5, for three hours. (This solution was prepared by dissolving the N-succinimidyl 3-maleimido propionate in DMF and then diluting 10-fold with buffer). After incubation, the slides were washed several times with milliQ water, dried by centrifugation, and stored at room temperature under vacuum until further use. A dilution series of the small compounds is arrayed and upon binding of cy3-labelled streptavidin or a 20 run Streptavidin coated Fluosphere to the array, the optimal dilution for detecting single molecules is established. Where Streptavidin is labeled with a single cy3 dye, the single step photobleaching characteristics of the dye are sufficient to indicate single molecules.

Preparation of Single Molecule Chemical Arrays

Each chemical compound in the library to be tested is synthesized with a common thiol functional group that enables covalent attachment to the slide surface. The compounds are spotted, in DMF, onto defined locations on the derivatized slides. Following printing, the slides are incubated at room temperature for 12 h and then immersed in a solution of 2-mercaptoethanol/DMF (1:99) to block remaining maleimide functionalities. 1 nL to defined locations on a series of maleimide-derivatized glass microscope slides 1 nL to defined locations on a series of maleimide-derivatized glass microscope slides. The slides were subsequently washed for 1 h each with DMF, THF, and iPrOH, followed by a 1 h aqueous wash with MBST (50 mM MES, 100 mM NaCl, 0.1% Tween20®, pH 6.0). Slides are rinsed with double-distilled water, dried by centrifugation.

Preparation of Protein Solutions

See below for preparation of protein solutions. These are then

Example 17

Antigen: Antibody

The following is adapted from the procedure of Haab and Brown

Preparation of Single Molecule Protein Arrays

Antibody/antigen pairs provided by BD Transduction Laboratories (Cincinnati, Ohio), Research Genetics (Huntsville, Ala.), and Sigma Chemical. Antibodies are chosen which are in glycerol-free, phosphate-buffered saline (PBS) solution (137 mM NaCl, 2.7 mM KCl, 4.3 mM $Na_2HPO_4$, 1.4 mM $KH_2PO_4$, pH 7.4). Antibody and antigen solutions are prepared at a concentration chosen from range from 0.0025-0.0075 mg/ml in 384-well plates, using approximately 4 µl per well (a wider range can be first tested depending on method to be used for analysis and the spotter that is to be used. The protein solutions in an ordered array onto poly-L-lysine coated microscope slides at a 375 µm spacing using 16 steel tips or the capillary tips of the Amersham Generation III spotter. The coated slides are purchased from CEL Associates (Houston, Tex.) or are prepared as follows. Briefly, glass microscope, slides are cleaned in 2.5 M NaOH for 2 h, rinsed thoroughly in ultra-pure $H_2O$, soaked for 1 hour in a 3% poly-L-lysine solution in PBS, rinsed in ultra-pure H2O, spun dry, and further dried for 1 h at 80° C. in a vacuum oven. The resulting microarrays are sealed in a slide box and stored at 4° C. The arrays are rinsed briefly in a 3% non-fat milk/PBS/0.1% Tween-20 solution to remove unbound protein. They are transferred immediately to a 3% non-fat milk/PBS/0.02% sodium azide blocking solution and allowed to sit overnight at 4° C. (The milk solution is first spun for 10 min at 10,000×g to remove particulate matter). Excess milk is removed in three room temperature PBS washes of 1 min each, and the arrays are kept in the final wash until application of the probe solution (see below).

Preparation of Protein Solutions

Protein solutions and NHS-ester activated Cy3 and Cy5 solutions (Amersham PA23001 and PA25001) are prepared in a 0.1 M pH 8.0 sodium carbonate buffer. The protein and dye solutions are mixed together so that the final protein concentration is 0.2-2 mg/ml and the final dye concentration was 100-300 p.M. Normally approximately 15 lig protein is labeled per array. The reactions are allowed to sit in the dark for 45 min and then quenched by the addition of a tenth volume 1 M pH 8 Tris base (a 500-fold molar excess of quencher). The reaction solutions are brought to 0.5 ml with PBS and then loaded into microconcentrator spin columns (Amicon Microcon 10) with a 10,000 Da molecular weight cutoff. After centrifugation to reduce the volume to approximately 10 1.11 (approximately 20 min), a 3% non-fat milk blocking solution is added to each Cy5-labeled solution such that 25 pi milk is added for each array to be generated from the mix. (The milk had been first spun down as above.) The volume is again brought to 0.5 ml with PBS and the sample again centrifuged to ~10 pl. The Cy3-labeled reference mix is divided equally among the Cy5-labeled mixes, and PBS is added to each to achieve 25 p.l for each array. Finally, the mixes are filtered with a 0.45 pm spin filter (Millipore) by centrifugation at 10,000×g for 2 min.

Each microarray is removed individually from the PBS wash, and excess liquid is shaken off. Without allowing the array to dry, 25 gl dye-labeled protein solution is applied to the surface in the area containing the array and a 24×30 mm cover slip is placed over the solution. The arrays are sealed in a chamber with an under-layer of PBS to provide humidification, after which they are left at 4° C. for 2 h. The arrays are dipped briefly in PBS to remove the protein solution and cover slip, and are then allowed to rock gently in PBS/0.1% Tween-20 solution for 20 min. The arrays are then washed twice in PBS for 5-10 min each and twice in H2O for 5-10 min each. All washes are at room temperature. After spinning to dryness in a centrifuge equipped with plate carriers (Beckman) or by removing moisture by forced air the single molecule protein arrays are ready for analysis.

Detection and Analysis

The arrays are analysed on a microscope or array scanner modified to enable single molecule detection and single molecule counting is used for quantization. The relative numbers of protein molecules in two separate dye-labeled pools is determined by comparing the number of fluorescent signals in the Cy3- and Cy5-specific channels in the data.

Example 18

Image Processing, Single Molecule Counting and Error Management

The above can be done using algorithms of any of the type in the detailed description of the invention. In addition below is an example of how to do single molecule counting using simple commercial software.

The objective is to use image analysis to count and determine the confidence in putative signals from single molecules within a microarray spot. The image processing package SigmaScanPro is used to automate single molecule counting and measurement. The procedure described here, or modifications of It, can be used for simple single molecule signal counting or more complex analyses of single molecule information, multicolour analysis and error management.

The microarray spot image is captured using a low light CCD camera, the I-PentaMAX GenIII or Gen IV (Roper Scientific) and an off-the-shelf frame grabber board. The single molecules are excited by laser in a TIRF configuration. Using a 100× objective and spots of approximately 200 microns in diameter.

The image is spatially calibrated using the Image, Calibrate, Distance and Area menu option. A 2-Point Resealing calibration is performed using micron units. Single molecule areas will then be reported in square microns.

Increasing the contrast between single molecules and the surrounding region will help identify the single molecules by thresholding. Image contrast is improved by performing a Histogram Stretch from the Image, Intensity menu. This procedure measures the grey levels in the image. The user then "stretches" the range of grey levels with significant magnitude over the entire 255 level intensity range. In this case moving the Old Start line with the mouse to an intensity of 64 will eliminate the effect of the insignificant dark gray levels and improve the contrast.

The single molecules can be identified by thresholding the intensity level to fill in the darkest objects. This is done by selecting Threshold, Intensity Threshold from the Image menu.

Under certain spotting conditions (e.g. 1.5M Betaine 3×SSC onto enhanced Aminosilane slides as well as in 50% DMSO buffer under certain conditions) the spot has a thin but discernibly bright ring round the edge. This can be used to define the area to be processed. This ring can be removed from contributing to the data by using image overlay layer math to intersect the single molecule signals with an overlay plane consisting of the interior of the ring. The overlay is created by filling light pixels in the interior of the spot and selecting out the ring by thresholding. Set the Level to be 180 and the option to select objects that are lighter than this level. Select the Fill Measurement mode (paint bucket icon) and left click in the interior of the plate to fill it. Set the source overlay to red in the Measurements, Settings, Overlays dialog. There are "holes" in the red overlay plane that are not filled since they contain bright pixels from the single molecules. To fill them select Image, Overlay Filters and select the Fill Holes option. Let both the source and destination overlays be red. The red circular overlay plane contains the green bacterial colonies.

The overlay math feature is used to identify the intersection of the red and green overlay planes. From the Image menu select Overlay Math and specify red and green to be the source layers and blue to be the destination layer. Then AND the two layers to obtain the intersection.

The blue pixels overlay the single molecule that can now be counted. Select the blue overlay plane as the source overlay from the Overlays tab in the Measurement Settings dialog. Select Perimeter, Area, Shape Factor, Compactness and Number of Pixels from the Measurements tab in the Measurements Settings dialog. Then measure the single molecule signals by using Measure Objects from the Measurements menu. The single molecule signals can be arbitrarily numbered and the corresponding measured quantities placed into an Excel (Microsoft) spreadsheet A macro is written to perform this for each spot in the array.

The microarray slide is translated relative to the CCD by a TST series X-Y translation stage (Newport) with images taken approximately every 100 micron spacings.

The example given here is for end-point analysis. However, for enhanced error discrimination real time analysis may be desirable, in this case a wider field images can be taken of the whole array by the CCD camera under lower magnification and enhanced by image processing. However, in most cases, a time window after the start of the reaction will have been determined within which the image should be acquired to gate out errors, which may occur early (non specific absorption) and late (mismatch interactions) in the process.

Adobe Photoshop software contains a number of image processing facilities which can be used and more advanced plug-ins are available. The Image Processing Toolkit is available which Plug-in to Photoshops, MicroGrafx Picture Publisher, NIH Image and other programs is available from Quantitative Image Analysis.

Example 19

Derivatization of Glass with Polyethylenimine (PEI)

For AFM analysis the array needs to be spotted onto a derivatised surface that is highly flat. AFM analysis requires a surface flatness of –1-2 nm or preferably below this. Glass slides, preferably polished can be derivatised with Polyethylenimine which by contrast to reagents such as APTES gives a relatively flat surface coating that is appropriate to AFM analysis. A glass slide is washed with 0.1 N acetic acid, then rinsed with water until the water rinsed from the slide has a pH equal to the pH of the water being used to rinse the slide. The slide is then allowed to dry. To a 95:5 ethanol:water solution is added a sufficient quantity of a 50% w/w solution of trimethoxysilylpropyl-polyethylenimine (600 MW) in 2- to achieve a 2% w/w final concentration. After stirring this 2% solution for five minutes, the glass slide is dipped into the solution, gently agitated for 2 minutes, and then removed. The glass slide is dipped into ethanol in order wash away excess sialylating agent. The glass slide is then air dried. Aminated oligonucleotides are spotted in a 1 M sodium borate pH 8.3 based buffer or 50% DMSO. Mica which can be atomically flat can be coated with PEI in a similar way.

Genomic DNA Labelling Protocol

Developed for microarray-based comparative genomic hybridization.

Genomic DNA can be labelled with a simple random-priming protocol based on Gibco/BRL's Bioprime DNA Labeling kit, though nick translation protocols work too. For example, the BioPrime labelling kit (Gibco/BRL) is a convenient and inexpensive source of random octamers, reaction buffer, and high concentration klenow, though other sources of random primers and high concentration klenow work as well.

1. Add 2 ug DNA of the sample to be labeled to an eppindorf tube.

Note: For high complexity DNAs (e g. human genomic DNA), the labelling reaction works more efficiently if the fragment size of the DNA is first reduced. This may be accomplished by restriction enzyme digestion (usually Dpn.11, though other 4-cutters work as well). After digestion, the DNA should be cleaned up by phenol/chloroform extraction/EtOH precipitation (Qiagen PCR purification kit also works well).

2. Add ddH2O or TE 8.0 to bring the total volume to 21 ul. Then add 20 ul of 2.5× random primer/reaction buffer mix. Boil 5 min, then place on ice.

2.5× Random Primer/Reaction Buffer Mix:
125 mM Tris 6.8
12.5 mM MgCl2
25 mM 2-mercaptoethanol
750 ug/ml random octamers 3. On ice, add 5 ul 10×dNTP mix.
10×dNTP Mix:
1.2 mM each dATP, dGTP, and dTTP
0.6 mM dCTP
10 mM Tris 8.0, 1 mM EDTA 4. Add 3 ul Cy5-dCTP or Cy3-dCTP (Amersham, 1 mM stocks)

Note: Cy-dCTP and Cy-dUTP work equally well. If using Cy-dUTP, adjust 10×dNTP mix accordingly.

5. Add 1 ul Klenow Fragment.

Note: High concentration klenow (40-50 units/up, available through NEB or Gibco/BRL (as part of the BioPrime labelling kit), produces better labelling.

6. Incubate 37 degrees C. for 1 to 2 hours, then stop reaction by adding 5 ul 0.5 M EDTA pH8.0

7. As with RNA probes, the DNA probe may be purified using a microcon 30 filter (Amicon/Millipore):
Add 450 ul TE 7.4 to the stopped labelling reaction.
Lay onto microcon 30 filter. Spin—10 min at 8000 g (10,000 rpm in microcentrifuge).
Invert and spin 1 min 8000 g to recover purified probe to new tube (~20-40 ul volume).

8. For two-color array hybridizations, combine purified probes (Cy5 and Cy3 labeled probes) in new eppindorf tube. Then add:
30-50 ug human Cot-I DNA (Gibco/BRL; 1 mg/ml stock; blocks hybridization to repetitive DNAs if present on array).
100 ug yeast tRNA (Gibco/13RL; make a 5 mg/ml stock; blocks non-specific DNA hybridization).
20 ug poly(dA)-poly(dT) (Sigma catalog No. P9764; make a 5 mg/ml stock; blocks hybridization to polyA tails of cDNA array elements).

450 ul TE 7.4

Concentrate with a microcon 30 filter as above (8000 g, —15 min, then check volume every 1 min until appropriate). Collect probe mixture in a volume of 12 ul or less.

9. Adjust volume of probe mixture to 12 ul with ddH2O. Then add 2.55 ul 20×SSC (for a final conc. of 3.4×) and 0.45 ul 10% SDS (for a final conc. of 0.3%).

Note: The final volume of hybridization is 15 ul. This volume is appropriate for hybridization under a 22 mm2 coverslip. Volumes should be adjusted upwards accordingly for larger arrays/coverslips.

10. Denature hybridization mixture (100° C., 15 min), incubate for 30 minutes at 37° C. (Cot-1 preannealing step), then hybridize to the array.

11. Hybridize microarray at 65° C. overnight (16-20 hrs). Note, see Human Array Hybridization protocol for details on hybridization.

12. Wash arrays as with mRNA labelling protocol and scan: First wash: 2×SSC, 0.03% SDS, 5 min 65° C.

Second wash: 1×SSC, 5 min RT 5 Third wash: 0.2×SSC, 5 min RT

Note: the first washing step should be performed at 65° C.; this appears to significantly increase the specific to non-specific hybridization signal.

Example 20

Making Spatially Addressable Arrays by AFM Deposition

A spatially addressable array of single molecules by picking up by AFM and deposition, at low cone is made, for example, by making a patterned array of loosely bound molecules, pulling a single molecule of this array and taking and deposition at a specific position on the substrate, of known coordinates. This coordinate can be addressed by light microscopy in single molecule fluorescence or by MM. Ideally the AFM stage will not be on piezo to minimize drift.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology, single molecule detection or combinatorial chemistry or related fields are intended to be within the scope of the following claims.

The invention claimed is:

1. A method of producing a molecular array comprising:
   (i) preselecting a plurality of oligonucleotides to be immobilised;
   (ii) labeling at least a portion of the plurality of oligonucleotides with one or more labels, thereby producing labeled oligonucleotides;
   (iii) immobilising at least a portion of the labeled oligonucleotides on a solid support at a density to allow each of said at least a portion of the labeled oligonucleotides on the solid support to be individually resolved, thereby forming two or more separate and discrete elements, at least two elements of said two or more elements being spatially addressable, each of said at least two elements comprising a plurality of labeled immobilised oligonucleotides from said at least a portion of the labeled oligonucleotides,
   wherein sequence identities of said at least a portion of the plurality of labeled immobilised oligonucleotides in each of said at least two elements is specified by a location of each of said at least two elements in which the oligonucleotides are contained; and
   (iv) analysing whether at least a portion of the labeled immobilised oligonucleotides of said at least two elements is individually optically resolvable from another portion of the labeled immobilised oligonucleotides, whereby said at least a portion of the labeled immobilised oligonucleotides on each of said at least two elements is individually optically resolvable from the another portion of the labeled immobilised oligonucleotides.

2. The method according to claim 1, wherein the one or more labels can be detected by optical methods.

3. The method according to claim 2, wherein the one or more labels is selected from the group consisting of a single optically active dye and fluorescent molecule, and a plurality of optically active dyes and fluorescent molecules.

4. The method according to claim 1, wherein the oligonucleotides are cDNA and/or genomic DNA.

5. The method according to claim 1, wherein the immobilising step comprises applying the labeled oligonucleotides to the solid support by a method selected from the group consisting of printing, electronic addressing, in situ light-directed synthesis, ink jet synthesis, physical masking, and spotting.

6. The method according to claim 1, wherein the plurality of oligonucleotides are identical oligonucleotides.

7. The method according to claim 1, wherein the plurality of oligonucleotides include functional molecules with different identities.

8. The method according to claim 1, wherein the immobilising step comprises centrifuging the labeled oligonucleotides on the solid support.

9. The method according to claim 1, wherein the solid support comprises a material selected from the group consisting of glass, quartz, silicon wafers, mica, ceramics organic polymers, plastics, polystyrene and polymethacrylate.

10. The method according to claim 1, wherein the labeled immobilised oligonucleotides are separated by a distance of approximately at least 250 nm.

11. The method according to claim 1, wherein the labeled immobilised oligonucleotides are separated by a distance of approximately at least 800 nm.

12. The method according to claim 1, wherein the labeled immobilised oligonucleotides are separated by a distance from 250 to 800 nm.

13. The method according to claim 1, wherein one of the at least two elements is adjacent to another element.

14. The method according to claim 1, wherein each of the at least two elements is from 1 $\mu$m to 300 $\mu$m apart.

15. The method according to claim 1, wherein each of the at least two elements has a dimension from 150 $\mu$m to 300 $\mu$m.

16. The method according to claim 1, wherein each of the at least two elements has a dimension larger than 500 $\mu$m.

17. The method according to claim 1, wherein the oligonucleotides have a length from 13 to 25 nucleotides.

18. The method according to claim 1, wherein the oligonucleotides have a length longer than 25 nucleotides.

19. The method according to claim 1, wherein the at least two elements are separated by a raised region or an etched trench.

20. The method according to claim 1, wherein the one or more labels are fluorescent labels.

21. The method according to claim 1, further comprising counting the number of the labeled immobilised oligonucleotides in each element of the at least two elements.

22. The method according to claim 21, wherein the labeled immobilised oligonucleotides within each element of the at least two elements are counted for one or more diagnostic purposes.

23. The method according to claim 1, wherein the labeling is performed by hybridising a labeled probe to only a portion of the plurality of oligonucleotides.

24. The method of claim 23, wherein the labeled probe is a labeled oligonucleotide.

25. The method according to claim 1, wherein the one or more labels are two or more different labels.

26. The method according to claim 1, wherein the solid support is a microtiter plate comprising raised region separating the two or more separate and discrete elements.

27. The method according to claim 1, wherein said at least a portion of the labeled immobilised oligonucleotides comprises circularized DNA.

28. The method according to claim 1, wherein at least a portion of the plurality of oligonucleotides is amplified by rolling circle amplification.

29. The method according to claim 1, wherein
   said plurality of labeled immobilized oligonucleotides comprise first immobilising means selected from the group consisting of (i) biotins, (ii) sulfhydryl (SH) groups, (iii) amine groups, (iv) phenylboronic acid (PBA) groups, and (v) acrydite groups, and
   said solid support comprises second immobilising means selected from the group consisting of (i) avidin, strepatavidin, or neutravidin, (ii) SH groups, (iii) activated carboxylate or aldehyde groups, (iv) salicylhydroxamic acid (SHA) groups, and (v)thiol surface, silane surface, or the surface containing acrylamide monomers.

30. A method of performing an assay comprising: producing the molecular array according to the method of claim 1, and performing the assay comprising counting a total number of at least a part of the plurality of labeled immobilised oligonucleotides of said at least two elements.

* * * * *